(12) United States Patent
Fahnestock

(10) Patent No.: US 6,268,169 B1
(45) Date of Patent: *Jul. 31, 2001

(54) RECOMBINANTLY PRODUCED SPIDER SILK

(75) Inventor: Stephen R. Fahnestock, Wilmington, DE (US)

(73) Assignee: E. I. du Pont de Nemours and Company, Wilmington, DE (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/556,978

(22) PCT Filed: Jun. 15, 1994

(86) PCT No.: PCT/US94/06689

§ 371 Date: Dec. 11, 1995

§ 102(e) Date: Dec. 11, 1995

(87) PCT Pub. No.: WO94/29450

PCT Pub. Date: Dec. 22, 1994

Related U.S. Application Data

(63) Continuation-in-part of application No. 08/077,600, filed on Jun. 15, 1993, now abandoned.

(51) Int. Cl.[7] ............................ C12N 1/21; C12N 1/15; C12N 15/11; C12N 15/63
(52) U.S. Cl. ............ 435/69.1; 435/243; 435/252.31; 435/252.33; 435/252.35; 435/254.2; 435/254.23; 435/254.3; 435/320.1; 530/300; 530/353; 536/23.1; 536/23.4
(58) Field of Search ................. 435/69.1, 69.7, 435/91.5, 91.52, 172.1, 252.3, 252.31, 252.33, 252.35, 254.21, 254.11, 254.3, 255.5, 320.1, 325, 839, 849; 530/324, 353, 412; 536/23.4, 23.5, 24.1

(56) References Cited

U.S. PATENT DOCUMENTS 5,171,505  12/1992  Lock ..................... 264/202
5,243,038 * 9/1993  Ferrari et al. ........... 536/23.1
5,245,012 * 9/1993  Lombari et al. ........ 530/353

FOREIGN PATENT DOCUMENTS 0 206 783    12/1986  (EP).
0 230 702     8/1987  (EP).
0 452 /925   10/1991  (EP).
WO 91/16351  10/1991  (WO).

OTHER PUBLICATIONS

Kempe, T. et al, *Gene*, 39, 239–245 (1985).

Hinman, M.B. et al, *J. of Biol. Chem.*, 267(27), 19320–19324 (1992).

Lombardi, S.J. et al, *Acta Zool Fennica*, 190, 243–248 (1990).

Lewis, R.V., *Acc. Chem. Res.*, 25, 392–398 (1992).

Beckwitt et al. Sequence conservation in the C–terminal region of spider silk proteins (spidroin) from *Nephila clavipes* (Tetragnathidae) and *Araneus bicentenarius* (Araneidae). The Journal of Biological Chemistry. vol. 269, No. 9, pp. 6661–6663, Mar. 4, 1994.*

Prince et al. Construction, cloning, and expression of synthetic genes encoding spider dragline protein. Biochemistry. vol. 34, No. 34, pp. 10879–10885, Aug. 29, 1995.*

Robson et al. Characterization of lamprin, an unusual matrix protein from lamprey cartilage. The Journal of Biological Chemistry. vol. 268, No. 2, pp. 1440–1447, Jan. 15, 1993.*

Xu et al. Structure of a protein superfiber: spider dragline silk. Proceedings of the National Academy of Sciences, USA. vol. 87, No. 18, pp. 7120–7124, Sep. 1990.*

* cited by examiner

Primary Examiner—Christine J. Saoud

(57) ABSTRACT

The invention relates to novel spider silk protein analogs derived from the amino acid consensus sequence of repeating units found in the natural spider dragline of *Nephila clavipes*. More specifically, synthetic spider dragline has been produced from *E. coli* and *Bacillus subtilis* recombinant expression systems wherein expressions from *E. coli* is at levels greater than 1 mg full-length polypeptide per gram of cell mass.

16 Claims, 28 Drawing Sheets

FIG. 1

```
 1                                     ...    QG A GAAAAAA-GG
 2   A GQG GYG GLG GQG  -   ---  ---   ---  -  ----------
 3   A GQG GYG GLG GQG  A   ---  ---   GQG  A  GAAAAAAAGG
 4   A GQG GYG GLG SQG  A   GRG  ---   GQG  A  GAAAAAA-GG
 5   A GQG GYG GLG SQG  A   GRG  GLG   GQG  A  GAAAAAAAGG
 6   A GQG GYG GLG NQG  A   GRG  ---   GQG  -  --AAAAAGG
 7   A GQG GYG GLG SQG  A   GRG  GLG   GQG  A  GAAAAAA-GG
 8   A GQG GYG GLG GQG  -   ---  ---   ---  -  ----------
 9   A GQG GYG GLG SQG  A   GRG  GLG   GQG  A  GAAAAAAAGG
10   A GQG --- GLG GQG  A   ---  ---   GQG  A  GASAAAA-GG
11   A GQG GYG GLG SQG  A   GRG  ---   GEG  A  GAAAAAA-GG
12   A GQG GYG GLG GQG  -   ---  ---   ---  -  ----------
13   A GQG GYG GLG SQG  A   GRG  GLG   GQG  A  GAAAA---GG
14   A GQG --- GLG GQG  A   ---  ---   GQG  A  GAAAAAA-GG
15   A GQG GYG GLG SQG  A   GRG  GLG   GQG  A  GAVAAAAAGG
16   A GQG GYG GLG SQG  A   GRG  ---   GQG  A  GAAAAAA-GG
17   A GQR GYG GLG NQG  A   GRG  GLG   GQG  A  GAAAAAAAGG
18   A GQG GYG GLG NQG  A   GRG  ---   GQG  -  --AAAA-GG
19   A GQG GYG GLG SQG  A   GRG  ---   GQG  A  GAAAAAA-VG
20   A GQE --- GIR GQG  -   ---  ---   ---  -  ----------
21   A GQG GYG GLG SQG  S   GRG  GLG   GQG  A  GAAAAAA-GG
22   A GQG --- GLG GQG  A   ---  ---   GQG  A  GAAAAAA-GG
23   V RQG GYG GLG SQG  A   GRG  ---   GQG  A  GAAAAAA-GG
24   A GQG GYG GLG GQG  V   GRG  GLG   GQG  A  GAAAA---GG
25   A GQG GYG GVG S--  -   ---  ---   --G  A  SAASAAAA--
```

SEQ. NO. 19

FIG. 2A

"MONOMER":

```
                     G    AGRG---GQGAGAAAAAA-GG   SEQ.NO. 20
AGQGGYGGLGSQG    AGRGGLGGQGAGAAAAAAGG
AGQGG---LGSQG    A------GQGAGAAAAA-GG
AGQGGYGGLGSQG    --------------------
AGQGGYGGLGSQ
```

FIG. 2B

"POLYMER":

```
-                    G    AGRG---GQGAGAAAAA-GG   SEQ.NO. 21
AGQGGYGGLGSQG    AGRGGLGGQGAGAAAAAAGG
AGQGG---LGSQG    A------GQGAGAAAAA-GG
AGQGGYGGLGSQG    --------------------
AGQGGYGGLGSQG    AGRG---GQGAGAAAAA-GG
AGQGGYGGLGSQG    AGRGGLGGQGAGAAAAAAGG
AGQGG---LGSQG    A------GQGAGAAAAA-GG
AGQGGYGGLGSQG    --------------------
AGQGGYGGLGSQG    AGRG---GQGAGAAAAA-GG
AGQGGYGGLGSQG    AGRGGLGGQGAGAAAAAAGG
AGQGG---LGSQG    A------GQGAGAAAAA-GG
AGQGGYGGLGSQG    --------------------
AGQGGYGGLGSQG    AGRG---GQGAGAAAAA-GG
AGQGGYGGLGSQG    AGRGGLGGQGAGAAAAAAGG
AGQGG---LGSQG    A------GQGAGAAAAA-GG
AGQGGYGGLGSQG    --------------------
AGQGGYGGLGSQG    AGRG---GQGAGAAAAA-GG
AGQGGYGGLGSQG    AGRGGLGGQGAGAAAAAAGG
AGQGG---LGSQG    A------GQGAGAAAAA-GG
AGQGGYGGLGSQG    --------------------
AGQGGYGGLGSQG    AGRG---GQGAGAAAAA-GG
AGQGGYGGLGSQG    AGRGGLGGQGAGAAAAAAGG
AGQGG---LGSQG    A------GQGAGAAAAA-GG
AGQGGYGGLGSQG    --------------------
AGQGGYGGLGSQ
```

FIG.3A

"MONOMER":

```
                   G ------------------- SEQ.NO. 22
AGQGGYGGLGSQG  AGRGGLGGQGAGAAAAAAGG
AGQGG---LGSQG  A------GQGAGAAAAA-GG
AGQGGYGGLGSQG  AGRG---GQGAGAAAAA-GG
AGQGGYGGLGSQ
```

FIG.3B

"POLYMER":

```
                   G ------------------- SEQ.NO. 23
AGQGGYGGLGSQG  AGRGGLGGQGAGAAAAAAGG
AGQGG---LGSQG  A------GQGAGAAAAA-GG
AGQGGYGGLGSQG  AGRG---GQGAGAAAAA-GG
AGQGGYGGLGSQG  --------------------
AGQGGYGGLGSQG  AGRGGLGGQGAGAAAAAAGG
AGQGG---LGSQG  A------GQGAGAAAAA-GG
AGQGGYGGLGSQG  AGRG---GQGAGAAAAA-GG
AGQGGYGGLGSQG  --------------------
AGQGGYGGLGSQG  AGRGGLGGQGAGAAAAAAGG
AGQGG---LGSQG  A------GQGAGAAAAA-GG
AGQGGYGGLGSQG  AGRG---GQGAGAAAAA-GG
AGQGGYGGLGSQG  --------------------
AGQGGYGGLGSQG  AGRGGLGGQGAGAAAAAAGG
AGQGG---LGSQG  A------GQGAGAAAAA-GG
AGQGGYGGLGSQG  AGRG---GQGAGAAAAA-GG
AGQGGYGGLGSQG  --------------------
AGQGGYGGLGSQG  AGRGGLGGQGAGAAAAAAGG
AGQGG---LGSQG  A------GQGAGAAAAA-GG
AGQGGYGGLGSQG  AGRG---GQGAGAAAAA-GG
AGQGGYGGLGSQG  --------------------
AGQGGYGGLGSQG  AGRGGLGGQGAGAAAAAAGG
AGQGG---LGSQG  A------GQGAGAAAAA-GG
AGQGGYGGLGSQG  AGRG---GQGAGAAAAA-GG
AGQGGYGGLGSQ
```

FIG. 4A

Oligonucleotide L

GGGCCGGACGTGGTTGGTCTTGGCCTGGCCGGCCAGCTGGTGGTGCTGCAGGGGTCTTGGCTCACAAG SEQ. NO. 24
TTCCCCGGCTGCACCACCGGAACCAGTCCGGACGACGGGACCAGTCCCGCCAGAACCGAGTG         SEQ. NO. 25
▶ GlyAlaGlyArgGlyGlyLeuGlyGlnGlyAlaAlaAlaAlaAlaAlaGlyGlyAlaGlyGlnGlyLeuGlySerGln SEQ. NO. 26

FIG. 4B

Oligonucleotide M1

GGGCCGGTCAAGGCCGCTGGTGCTGCCAGCAGCTGCCGCTGGCCAGGCCAAGGTGGATATGTGGCTTAGGTCACAAG SEQ. NO. 27
TTCCCCGGCCAGTCCGGCGACCACGACGGTCGTCGACGGCGACCGGTCCGGTTCCACCTATACCACGAATCCCAGTG SEQ. NO. 28
▶ GlyAlaGlyGlnGlyAlaAlaAlaAlaAlaAlaGlyGlyAlaGlyGlnGlyTyrGlyLeuGlySerGln SEQ. NO. 29

FIG. 4C

Oligonucleotide M2

GGGCCGGTCGAGGTGGACAAGGTGCAGGTGACAGCCGCTGCTGCGCGGGCCGCCAGTGCAAGTGGCTCAAGTGGGGTATGGGGTCAAGTGGGTTTAGGTTCACAAG SEQ. NO. 30
TTCCCCGGCCAGCTCCACCTGTTCCACGTCCACTGTCGGCGACGACGCGCCCGGCGGTCACGTTCCAGTCACCATACCCCAAATCCAAGTG                  SEQ. NO. 31
▶ GlyAlaGlyArgGlyGlyLeuGlyGlnGlyAlaAlaAlaAlaAlaAlaGlyGlyAlaGlyGlnGlyTyrGlyLeuGlySerGln SEQ. NO. 32

FIG. 4D

Oligonucleotide S

GGGCCGGGCAAGGTGGTTACGGCGGTCTCGGATCACAAG SEQ. NO. 33
TTCCCCGGGCCGTTCCACCAATGCCGCCAGAGCCTAGTG SEQ. NO. 34
▶ GlyAlaGlyGlnGlyGlyTyrGlyLeuGlySerGln SEQ. NO. 35

```
    BamHI                                           SEQ. NO. 39
... GGA TCC CAT CAC CAT CAC CAT CAC TCT AGA TCC GGC TGC TAA
... Gly Ser His His His His His His Ser Arg Ser Gly Cys END
                                                 SEQ. NO. 40
```

FIG. 7A

Oligonucleotide A

```
              SmaI                                                              PvuII
2    GATCTCCCGGGCCATCCGGCCCAGGTTCTGGGCAGCGGGCAGCAGGGGCCCAGGGCAGCAGCTGG                    SEQ. NO. 41
              AGGGCCCGGTAGGCCGGGTCCAAGACCCGTCGCCCGTCGTCCCGGGTCCCGTCGTCGACCCTAG               SEQ. NO. 42
1▶ SerProGlyProSerGlyProGlySerAlaAlaAlaAlaAlaAlaGlyProGlyGlnGlnLeu                       SEQ. NO. 43
```

FIG. 7B

Oligonucleotide B

```
     SmaI                                                                       PvuII
GATCTCCCGGGCCGGGGCGGGGTTACGGTCTCCGGTCAGCAAGGCCCAGGTGGCTACGGCCCAGCCAACAGCTGG              SEQ. NO. 44
     AGGGCCCGGCCCCGCCCCAATGCCAGAGGCCAGTCGTTCCGGGTCCACCGATGCCGGTCCGGTTGTCGACCCTAG         SEQ. NO. 45
▶ SerProGlyProGlyGlyGlyValProValSerGlnGlnGlyProGlyGlyTyrGlyProGlyGlnGlnLeu              SEQ. NO. 46
```

FIG. 7C

Oligonucleotide C

```
     SmaI                                                                       SnaBI
GATCTCCCGGGCCATCTGTCGCTGCTGCTGCTGCGGCTAGCGCTGCCGCAGTCCAGGCGGTCCAGGTCCGTACGTAG           SEQ. NO. 47
     AGGGCCCGGTAGACAGCGACGACGACGACGCCGATCGCGACGGCGTCAGGTCCGCCAGGTCCAGGCATGCATCCTAG      SEQ. NO. 48
▶ SerProGlyProSerGlySerAlaAlaAlaAlaAlaAlaAlaAlaAlaGlyProGlyGlyTyrVal                    SEQ. NO. 49
```

FIG. 7D

Oligonucleotide D

```
        SmaI                                  PvuII
GATCTCCCGGGCCGGGCCAACAAGTCCGGGCGGCTATGGTCCAGGTCAACAGCTGG        SEQ.NO. 50
    AGGGCCCGGTTGTTCCAGGCCCGCCGATACCAGGTCCAGTTGTCGACCCTAG        SEQ.NO. 51
  ▶ SerProGlyGlnGlnGlyProGlyTyrGlyProGlyGlnGlnLeu                SEQ.NO. 52
```

FIG. 7E

Oligonucleotide E

```
        SmaI                                                                SnaBI
GATCTCCCGGGCCGAGCGGTTCCGCAGCAGCAGCGGCTGCGGCGCAGCGGGTCCAGTTGGTTACGTAG        SEQ.NO. 53
    AGGGCCCGGCTCGCCAAGGCGTCGTCGTCGCCGACGCCGCGTCGCCCAGGTCCACCAATGCATCCTAG    SEQ.NO. 54
  ▶ SerProGlyProSerGlyProGlySerAlaAlaAlaAlaAlaAlaAlaGlyProGlyGlyTyrVal      SEQ.NO. 55
```

FIG. 7F

Oligonucleotide F

```
        SmaI                                                          PvuII
GATCTCCCGGGCCCAGGCCAGGCCAGCAGGTCCGGGTTGGCTATGGCCCAGGTCCGGTGGTTACGTCCAGTTCCGGTTACGGTCCAGTCAGCAGCTGG      SEQ.NO. 56
    AGGGCCCGGTCCGGTCGTCCAGGCCCACCGGTCCGGTCGTTCCAGGCCCACCAATGCCAGGTCCAGGCCACCAATGCAGCTCGAGCTGACCCTAG    SEQ.NO. 57
  ▶ SerProGlyGlnGlnGlyProGlyTyrGlyProGlyGlnGlnGlyProGlyTyrGlyProGlyGlnGlnLeu                             SEQ.NO. 58
```

FIG.8

SEQ.NO. 59

```
                ...PGGY GPGQQ GPGGY GPGQQ GP--SGPGS AAAAAAAAAA
GPGGY GPGQQ GPGGY GPGQQ GPGRY GPGQQ GP--SGPGS AAAAAA----
-----. GSGQQ GPGGY GPRQQ GPGGY GQGQQ GP--SGPGS AAAASAAASA ESGQQ
GPGGY GPGQQ GPGGY GPGQQ GPGGY GPGQQ GP--SGPGS AAAAAAAAS-
----- GPGQQ GPGGY GPGQQ GPGGY GPGQQ GP--SGPGS AAAAAAAAS-
----- GPGQQ GPGGY GPGQQ GPGGY GPGQQ GL--SGPGS AAAAAAA---
----- ----- ----- GPGQQ GPGGY GPGQQ GP--SGPGS AAAAAAAA-
----- ----- GPGGY GPGQQ GPGGY GPGQQ GP--SGAGS AAAAAAA---
----- GPGQQ GLGGY GPGQQ GPGGY GPGQQ GPGGYGPGS ASAAAAA--
----- ----- ----- GPGQQ GPGGY GPGQQ GP--SGPGS ASAAAAAAA
----- ----- GPGGY GPGQQ GPGGY APGQQ GP--SGPGS ASAAAAAAA
----- ----- GPGGY GPGQQ GPGGY APGQQ GP--SGPGS AAAAAASA-
----- ----- ----- ----- GPGGY GPAQQ GP--SGPGI AASAASA---
----- ----- ----- ----- GPGGY GPAQQ GPAGYGPGS AVAASA----
----- ----- ----- ----- ----- ---GA GSAGYGPGS QASAAAS---
```

FIG.9A

"MONOMER": 119 aa

SEQ.NO. 60

```
                                            IGP--SGPGS AAAAAA----
----- GPGQQIGPGGY GPGQQ GPGGY GPGQQIGP--SGPGS AAAAAAAA--
----- ----- GPGGYIGPGQQ GPGGY GPGQQIGP--SGPGS AAAAAAAAA-
GPGGYIGPGQQ GPGGY GPGQQ GPGGY GPGQQI
```

FIG.9B

"POLYMER":

SEQ.NO. 61

```
                                            IGP--SGPGS AAAAAA----
----- GPGQQIGPGGY GPGQQ GPGGY GPGQQIGP--SGPGS AAAAAAAA--
----- ----- GPGGYIGPGQQ GPGGY GPGQQIGP--SGPGS AAAAAAAAA-
GPGGYIGPGQQ GPGGY GPGQQ GPGGY GPGQQIGP--SGPGS AAAAAA----
----- GPGQQIGPGGY GPGQQ GPGGY GPGQQIGP--SGPGS AAAAAAAA--
----- ----- GPGGYIGPGQQ GPGGY GPGQQIGP--SGPGS AAAAAAAAA-
GPGGYIGPGQQ GPGGY GPGQQ GPGGY GPGQQIGP--SGPGS AAAAAA----
----- GPGQQIGPGGY GPGQQ GPGGY GPGQQIGP--SGPGS AAAAAAAA--
----- ----- GPGGYIGPGQQ GPGGY GPGQQIGP--SGPGS AAAAAAAAA-
GPGGYIGPGQQ GPGGY GPGQQ GPGGY GPGQQIGP--SGPGS AAAAAA----
----- GPGQQIGPGGY GPGQQ GPGGY GPGQQIGP--SGPGS AAAAAAAA--
----- ----- GPGGYIGPGQQ GPGGY GPGQQIGP--SGPGS AAAAAAAAA-
GPGGYIGPGQQ GPGGY GPGQQ GPGGY GPGQQIGP--SGPGS AAAAAA----
----- GPGQQIGPGGY GPGQQ GPGGY GPGQQIGP--SGPGS AAAAAAAA--
----- ----- GPGGYIGPGQQ GPGGY GPGQQIGP--SGPGS AAAAAAAAA-
GPGGYIGPGQQ GPGGY GPGQQ GPGGY GPGQQI
```

FIG.10A

"MONOMER"

```
            S Q G   - - - - - - - - - - - - - - - - - - - - - - - SEQ.NO. 62
A G Q G G Y G G L G S Q G   A G R G G L G G Q G A G A A A A A A G G
A G Q G G - - - L G S Q G   A - - - - - - G Q G A G A A A A A - G G
A G Q G G Y G G L G S Q G   A G R G - - - G Q G A G A A A A A - G G
A G Q G G Y G G L G
```

FIG.10B

"POLYMER":

```
            S Q G   - - - - - - - - - - - - - - - - - - - - - - - SEQ.NO. 63
A G Q G G Y G G L G S Q G   A G R G G L G G Q G A G A A A A A A G G
A G Q G G - - - L G S Q G   A - - - - - - G Q G A G A A A A A - G G
A G Q G G Y G G L G S Q G   A G R G - - - G Q G A G A A A A A - G G
A G Q G G Y G G L G S Q G   - - - - - - - - - - - - - - - - - - -
A G Q G G Y G G L G S Q G   A G R G G L G G Q G A G A A A A A A G G
A G Q G G - - - L G S Q G   A - - - - - - G Q G A G A A A A A - G G
A G Q G G Y G G L G S Q G   A G R G - - - G Q G A G A A A A A - G G
A G Q G G Y G G L G S Q G   - - - - - - - - - - - - - - - - - - -
A G Q G G Y G G L G S Q G   A G R G G L G G Q G A G A A A A A A G G
A G Q G G - - - L G S Q G   A - - - - - - G Q G A G A A A A A - G G
A G Q G G Y G G L G S Q G   A G R G - - - G Q G A G A A A A A - G G
A G Q G G Y G G L G S Q G   - - - - - - - - - - - - - - - - - - -
A G Q G G Y G G L G S Q G   A G R G G L G G Q G A G A A A A A A G G
A G Q G G - - - L G S Q G   A - - - - - - G Q G A G A A A A A - G G
A G Q G G Y G G L G S Q G   A G R G - - - G Q G A G A A A A A - G G
A G Q G G Y G G L G S Q G   - - - - - - - - - - - - - - - - - - -
A G Q G G Y G G L G S Q G   A G R G G L G G Q G A G A A A A A A G G
A G Q G G - - - L G S Q G   A - - - - - - G Q G A G A A A A A - G G
A G Q G G Y G G L G S Q G   A G R G - - - G Q G A G A A A A A - G G
A G Q G G Y G G L G S Q G   - - - - - - - - - - - - - - - - - - -
A G Q G G Y G G L G S Q G   A G R G G L G G Q G A G A A A A A A G G
A G Q G G - - - L G S Q G   A - - - - - - G Q G A G A A A A A - G G
A G Q G G Y G G L G S Q G   A G R G - - - G Q G A G A A A A A - G G
A G Q G G Y G G L G
```

FIG. 11A

Oligonucleotide 1

```
GATCTCAGGGTCTGCTGGCCAGGGTGGCTATGGTGGCCTGG        SEQ. NO. 64
          AGTCCCACGACCGGTCCCACCGATACCACCGGACCCTAG  SEQ. NO. 65
        ▸ SerGlnGlyAlaGlyGlnGlyAlaGlyTyrGlyGlyLeuGly SEQ. NO. 66
```

FIG. 11B

Oligonucleotide 2

```
GATCTCAAGGCGCTGGTGCGCTGGTGGCCTGGGTGGCCAGGTGCTGCTGGGGTGCTGCTGGTGCTGGTGCAGGTGGTCTGG        SEQ. NO. 67
          AGTTCCGCGACCAGCGACCACCGGACCCACCGGTCCACGACGACCACACCACACGACCACGTCCACCAGACCCTAG        SEQ. NO. 68
        ▸ SerGlnGlyAlaGlyArgGlyGlyLeuGlyGlyLeuGlyGlnGlyAlaGlyAlaAlaAlaAlaAlaAlaGlyAlaGlyGlnGlyAlaGlyAlaAlaGlyGlyGlyLeuGly SEQ. NO. 69
```

FIG. 11C

Oligonucleotide 3

```
GATCTCAGGGCGCAGGTCAGGTGTGCTGGTGGGGCGCAGCTGGTGGGCGGAGCTGGGGGTCAAGGTGGCTACGCGGTTAG        SEQ. NO. 70
          AGTCCCGCGTCCAGTTCCACGACGCCACCCGCGTCGACCACCCGCGATCCGCCAGTTCCACGATGCGCCAATCCTAG        SEQ. NO. 71
        ▸ SerGlnGlyAlaGlyGlnGlyAlaGlyAlaAlaAlaAlaAlaAlaGlyAlaGlyGlnGlyAlaGlyTyrGlyGlyLeuGly SEQ. NO. 72
```

FIG. 11D

Oligonucleotide 4

```
GATCTCAAGGTGCAGGTGCGGTGCTGGTGTGTCAGGGTCGGTGTGTCAGCAGCGGGCAGCAGCGGCGCTGCCAAGGTGGTTACGGTGGTCTTG        SEQ. NO. 73
          AGTTCCACGCGCCACGCCACGACCACAGTCCCAGCCACACAGTCGTCGCCCGTCGTCGCCGCGACGGTTCCACCAATGCCACCAGAACCTAG  SEQ. NO. 74
        ▸ SerGlnGlyAlaGlyArgGlyGlyLeuGlyAlaGlyAlaAlaAlaAlaAlaAlaGlyAlaGlyGlnGlyAlaGlyTyrGlyGlyLeuGly SEQ. NO. 75
```

FIG. 13A

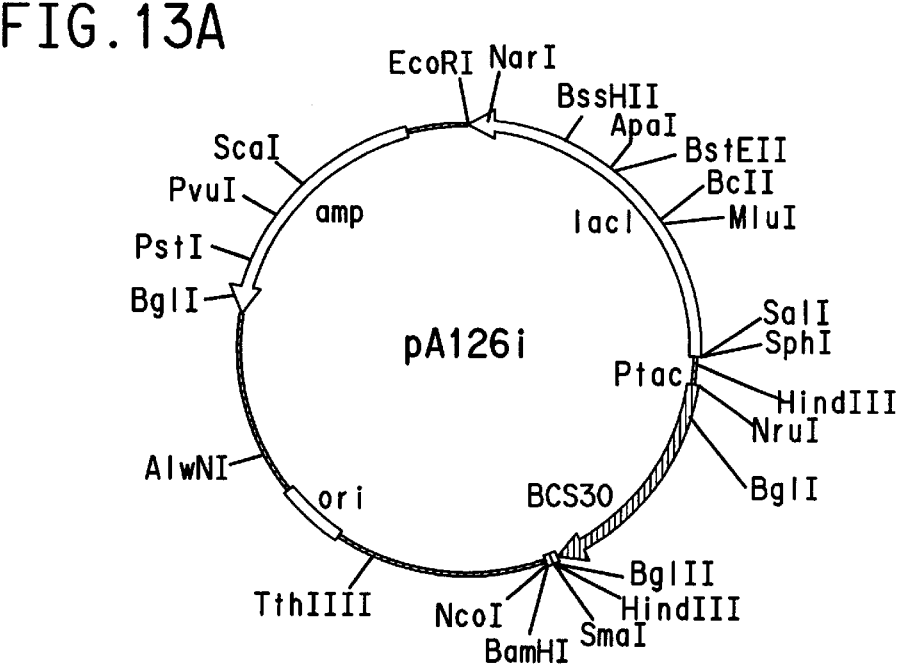

FIG. 13B

```
         EcoRI                                    SEQ. NO. 78
4909  GAATTCCGGGGGATTATGCGTTAAGCATAAAGTGTAAAGCCTGGGGTGCCTA
4961  ATGAGTGAGCTAACTCACATTAATTGCGTTGCGCTCACTGCCCGCTTTCCAG
5013  TCGGGAAACCTGTCGTGCCAGCTGCATTAATGAATCGGCCAACGCGCGGGGA
                      Bbel
                      NarI
5065  GAGGCGGTTTGCGTATTGGGCGCCAGGGTGGTTTTTCTTTTCACCAGTGAGA
5117  CGGGCAACAGCTGATTGCCCTTCACCGCCTGGCCCTGAGAGAGTTGCAGCAA
5169  GCGGTCCACGCTGGTTTGCCCCAGCAGGCGAAAATCCTGTTTGATGGTGGTT
5221  GACGGCGGGATATAACATGAGCTGTCTTCGGTATCGTCGTATCCCACTACCG
                                                 BssHII
5273  AGATATCCGCACCAACGCGCAGCCCGGACTCGGTAATGGCGCGCATTGCGCC
5325  CAGCGCCATCTGATCGTTGGCAACCAGCATCGCAGTGGGAACGATGCCCTCA
5377  TTCAGCATTTGCATGGTTTGTTGAAAACCGGACATGGCACTCCAGTCGCCTT
5429  CCCGTTCCGCTATCGGCTGAATTTGATTGCGAGTGAGATATTTATGCCAGCC
                                                     ApaI
5481  AGCCAGACGCAGACGCGCCGAGACAGAACTTAATGGGCCCGCTAACAGCGCG
             BstEII
5533  ATTTGCTGGTGACCCAATGCGACCAGATGCTCCACGCCCAGTCGCGTACCGT
5585  CTTCATGGGAGAAAATAATACTGTTGATGGGTGTCTGGTCAGAGACATCAAG
5637  AAATAACGCCGGAACATTAGTGCAGGCAGCTTCCACAGCAATGGCATCCTGG
                                  BclI              MluI
5689  TCATCCAGCGGATAGTTAATGATCAGCCCACTGACGCGTTGCGCGAGAAGAT
5741  TGTGCACCGCCGCTTTACAGGCTTCGACGCCGCTTCGTTCTACCATCGACAC
5793  CACCACGCTGGCACCCAGTTGATCGGCGCGAGATTTAATCGCCGCGACAATT
5845  TGCGACGGCGCGTGCAGGGCCAGACTGGAGGTGGCAACGCCAATCAGCAACG
```

FIG. 13C

```
5897 ACTGTTTGCCCGCCAGTTGTTGTGCCACGCGGTTGGGAATGTAATTCAGCTC
5949 CGCCATCGCCGCTTCCACTTTTTCCCGCGTTTTCGCAGAAACGTGGCTGGCC
6001 TGGTTCACCACGCGGGAAACGGTCTGATAAGAGACACCGGCATACTCTGCGA
6053 CATCGTATAACGTTACTGGTTTCACATTCACCACCCTGAATTGACTCTCTTC
6105 CGGGCGCTATCATGCCATACCGCGAAAGGTTTTGCGCCATTCGATGGTGTCA
6157 ACCTTGCAGAGCTGCGCCTTTATTATTATCCGCCGGGAGAAAATATTCCGTG
                                      SalI       SphI
6209 GATCTAACGGGATGCGTTATGTTGAAGTGAGACCGGTCGACGCATGCCAGGA
                                              HindIII
6261 CAACTTCTGGTCCGGTAACGTGCTGAGCCCGGCCAAGCTTACTCCCCATCCC
6313 CCTGTTGACAATTAATCATCGGCTCGTATAATGTGTGGAATTGTGAGCGGAT
6365 AACAATTTCACACAGGAAACAGGATCACTAAGGAGGTTTAAATATGGCTACT
          NruI
6417 GTTATAGATCCGTCTGTCGCGACGGCCGTTTCGTCGAATGGCTCGGTTGCCA
6469 ATATCAATGCGATCAAGTCGGGCGCTCTGGAGTCCGGCTTTACGCAGTCAGA
        BglI
6521 CGTTGCCTATTGGGCCTATAACGGCACCGGCCTTTATGATGGCAAGGGCAAG
6573 GTGGAAGATTTGCGCCTTCTGGCGACGCTTTACCCGGAAACGATCCATATCG
6625 TTGCGCGTAAGGATGCAAACATCAAATCGGTCGCAGACCTGAAAGGCAAGCG
6677 CGTTTCGCTGGATGAGCCGGGTTCTGGCACCATCGTCGATGCGCGTATCGTT
6729 CTTGAAGCCTACGGCCTCACGGAAGACGATATCAAGGCTGAACACCTGAAGC
6781 CGGGACCGGCAGGCGAGAGGCTGAAAGATGGTGCGCTGGACGCCTATTTCTT
6833 TGTGGGCGGCTATCCGACGGGCGCAATCTCGGAACTGGCCATCTCAACGGT
6885 ATTTCGCTCGTTCCGATCTCCGGGCCGGAAGCGGACAAGATTCTGGAGAAAT
6937 ATTCCTTCTTCTCGAAGGATGTGGTTCCTGCCGGAGCCTATAAGGACGTGGC
6989 GGAAACACCGACCCTTGCCGTTGCCGCACAGTGGGTGACGAGCGCCAAGCAG
7041 CCGGACGACCTCATCTATAACATCACCAAGGCTGGTTCTCCGAAACCGGGTG
        BglII    HindIII    SmaI   BamHI            NcoI
7093 CTGGTAGATCTAAGCTTCCCGGGGATCCTAGCTAGCTAGCCATGGCATCACA
7145 GTATCGTGATGACAGAGGCAGGGAGTGGGACAAAATTGAAATCAAATAATGA
7197 TTTTATTTTGACTGATAGTGACCTGTTCGTTGCAACAAATTGATAAGCAATG
7249 CTTTTTATAATGCCAACTTAGTATAAAAAGCTGAACGAGAAACGTAAAAT
7301 GATATAAATATCAATATATTAAATTAGATTTTGCATAAAAACAGACTACAT
7353 AATACTGTAAAACACAACATATGCAGTCACTATGAATCAACTACTTAGATGG
7405 TATTAGTGACCTGTAACAGAGCATTAGCGCAAGGTGATTTTTGTCTTCTTGC
7457 GCTAATTTTTTGTCATCAAACCTGTCGCACTCCAGAGAAGCACAAAGCCTCG
7509 CAATCCAGTGCAAAGCTCTGCCTCGCGCGTTTCGGTGATGACGGTGAAAACC
7561 TCTGACACATGCAGCTCCCGGAGACGGTCACAGCTTGTCTGTAAGCGGATGC
7613 CGGGAGCAGACAAGCCCGTCAGGGCGCGTCAGCGGGTGTTGGCGGGTGTCGG
       TthIII
7665 GGCGCAGCCATGACCCAGTCACGTAGCGATAGCGGAGTGTATACTGGCTTAA
7717 CTATGCGGCATCAGAGCAGATTGTACTGAGAGTGCACCATATGCGGTGTGAA
7769 ATACCGCACAGATGCGTAAGGAGAAAATACCGCATCAGGCGCTCTTCCGCTT
7821 CCTCGCTCACTGACTCGCTGCGCTCGGTCGTTCGGCTGCGGCGAGCGGTATC
7873 AGCTCACTCAAAGGCGGTAATACGGTTATCCACAGAATCAGGGGATAACGCA
7925 GGAAAGAACATGTGAGCAAAAGGCCAGCAAAAGGCCAGGAACCGTAAAAAGG
7977 CCGCGTTGCTGGCGTTTTTCCATAGGCTCCGCCCCCTGACGAGCATCACAA
8029 AAATCGACGCTCAAGTCAGAGGTGGCGAAACCCGACAGGACTATAAAGATAC
8081 CAGGCGTTTCCCCCTGGAAGCTCCCTCGTGCGCTCTCCTGTTCCGACCCTGC
```

FIG. 13D

```
8133 CGCTTACCGGATACCTGTCCGCCTTTCTCCCTTCGGGAAGCGTGGCGCTTTC
8185 TCATAGCTCACGCTGTAGGTATCTCAGTTCGGTGTAGGTCGTTCGCTCCAAG
8237 CTGGGCTGTGTGCACGAACCCCCGTTCAGCCCGACCGCTGCGCCTTATCCG
8289 GTAACTATCGTCTTGAGTCCAACCCGGTAAGACACGACTTATCGCCACTGGC
         AlwNI
8341 AGCAGCCACTGGTAACAGGATTAGCAGAGCGAGGTATGTAGGCGGTGCTACA
8393 GAGTTCTTGAAGTGGTGGCCTAACTACGGCTACACTAGAAGGACAGTATTTG
8445 GTATCTGCGCTCTGCTGAAGCCAGTTACCTTCGGAAAAAGAGTTGGTAGCTC
8497 TTGATCCGGCAAACAAACCACCGCTGGTAGCGGTGGTTTTTTGTTTGCAAG
8549 CAGCAGATTACGCGCAGAAAAAAGGATCTCAAGAAGATCCTTTGATCTTTT
8601 CTACGGGGTCTGACGCTCAGTGGAACGAAAACTCACGTTAAGGGATTTTGGT
8653 CATGAGATTATCAAAAGGATCTTCACCTAGATCCTTTTAAATTAAAAATGA
8705 AGTTTTAAATCAATCTAAAGTATATATGAGTAAACTTGGTCTGACAGTTACC
8757 AATGCTTAATCAGTGAGGCACCTATCTCAGCGATCTGTCTATTTCGTTCATC
8809 CATAGTTGCCTGACTCCCCGTCGTGTAGATAACTACGATACGGGAGGGCTTA
8861 CCATCTGGCCCCAGTGCTGCAATGATACCGCGAGACCCACGCTCACCGGCTC
         BglI
8913 CAGATTTATCAGCAATAAACCAGCCAGCCGGAAGGGCCGAGCGCAGAAGTGG
8965 TCCTGCAACTTTATCCGCCTCCATCCAGTCTATTAATTGTTGCCGGGAAGCT
                                                         PstI
9017 AGAGTAAGTAGTTCGCCAGTTAATAGTTTGCGCAACGTTGTTGCCATTGCTG
9069 CAGGCATCGTGGTGTCACGCTCGTCGTTTGGTATGGCTTCATTCAGCTCCGG
9121 TTCCCAACGATCAAGGCGAGTTACATGATCCCCCATGTTGTGCAAAAAGCG
         PvuI
9173 GTTAGCTCCTTCGGTCCTCCGATCGTTGTCAGAAGTAAGTTGGCCGCAGTGT
9225 TATCACTCATGGTTATGGCAGCACTGCATAATTCTCTTACTGTCATGCCATC
             ScaI
9277 CGTAAGATGCTTTTCTGTGACTGGTGAGTACTCAACCAAGTCATTCTGAGAA
9329 TAGTGTATGCGGCGACCGAGTTGCTCTTGCCCGGCGTCAACACGGGATAATA
9381 CCGCGCCACATAGCAGAACTTTAAAAGTGCTCATCATTGGAAAACGTTCTTC
9433 GGGGCGAAAACTCTCAAGGATCTTACCGCTGTTGAGATCCAGTTCGATGTAA
9485 CCCACTCGTGCACCCAACTGATCTTCAGCATCTTTTACTTTCACCAGCGTTT
9537 CTGGGTGAGCAAAAACAGGAAGGCAAAATGCCGCAAAAAGGGAATAAGGGC
9589 GACACGGAAATGTTGAATACTCATACTCTTCCTTTTCAATATTATTGAAGC
9641 ATTTATCAGGGTTATTGTCTCATGAGCGGATACATATTTGAATGTATTTAGA
9693 AAAATAAACAAATAGGGGTTCCGCGCACATTTCCCCGAAAAGTGCCACCTGA
9745 CGTCTAAGAAACCATTATTATCATGACATTAACCTATAAAAATAGGCGTATC
9797 ACGAGGCCCTTTCGTCTTCAA
```

FIG. 14A

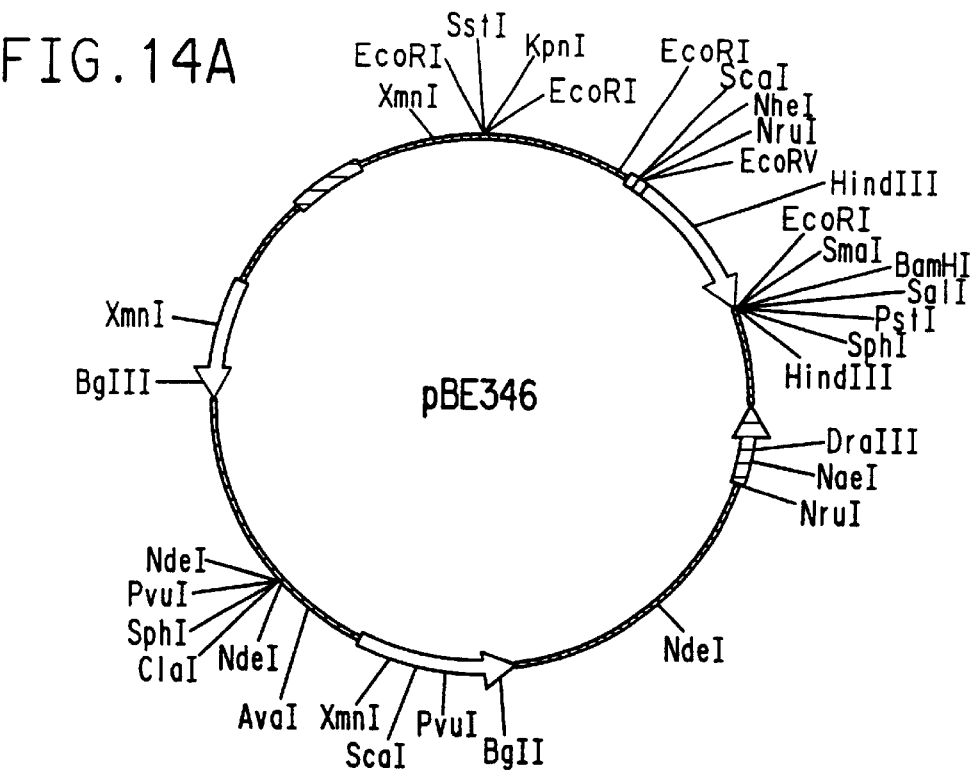

FIG. 14B

SEQ. NO. 79

```
        SstI      KpnI         EcoRI
  1 AATTCGAGCTCGGTACCCATCGAATTCCTTCAGGAAAAGAACGATGGCTGTC
 53 TTATTAGCGGTTGCAGGCACATTTATTTTGGTCACACACGGGAATGTCGGCA
105 GCCTGTCTATATCCGGTCTGGCTGTTTTTGGGGCATCAGCTCGGCATTTGC
157 GCTGGCGTTTTACACCCTCCAGCCGCATCGGCTTTTGAAGAAATGGGGCTCC
209 GCCATTATTGTCGGATGGGGCATGCTGATGCGGAGCCGTTCTCAGCCTGATT
261 CAGCCGCCTTGGAAGTTTGAAGGCCAATGGTCGTTGTCCGCATATGCCGCGA
313 TCGTGTTTATCATCATTTCGGAACGCTCATCGCTTTTATTGCTATTTGGA
365 AAGCCTGAAATATCTGAGTGCCTCTGAAACCAGCCTCCTCGCCTGTGCAGAG
417 CCGCTGTCAGCAGCTTTTTAGCGGTGATCTGGCTGCATGTTCCCTTCGGAA
469 TATCAGAATGGCTGGGTACTTTACTGATTTAGCCACCATCGCTTATTATCT
521 ATCAAGAAAAAATAACCTCTCTTTTTTAGAGAGGTTTTTCCCTAGGCCTGA
573 AGCACCCTTTAGTCTCAATTACCCATAAATTAAAAGGCCTTTTTTCGTTTA
625 CTATCATTCAAAAGAGGAAAATAGACCAGTTGTCAATAGAATCAGAGTCTAA
677 TAGAATGAGGTCGAAAAGTAAATCACGCAGGATTGTTACTGATAAAGCAGGC
729 AAGACCTAAAATGTGTTAAGGGCAAAGTGTATTCTTTGGCGTCATCCCTTAC
                                                EcoRI
781 ATATTTTGGGTCTTTTTTTCTGTAACAAACCTGCCATCCATGAATTCGGGAG
```

FIG. 14C

```
 833 GATCGAAACGGCAGATCGCAAAAACAGTACATACAGAAGGAGACATGAACAT
                                      ScaI
 885 GAACATCAAAAAAATTGTAAAACAAGCCACAGTACTGACTTTTACGACTGCA
     NheI                         NruI           EcoRV
 937 CTGCTAGCAGGAGGAGCGACTCAAGCCTTCGCGAAAGAAGATATCGATCAAC
 989 GCAATGGTTTTATCCAAAGCCTTAAAGATGATCCAAGCCAAAGTGCTAACGT
1041 TTTAGGTGAAGCTCAAAAACTTAATGACTCTCAAGCTCCAAAAGCTGATGCG
1093 CAACAAATAACTTCAACAAAGATCAACAAAGCGCCTTCTATGAAATCTTGA
1145 ACATGCCTAACTTAAACGAAGCGCAACGTAACGGCTTCATTCAAAGTCTTAA
1197 AGACGACCCAAGCCAAAGCACTAACGTTTTAGGTGAAGCTAAAAAATTAAAC
1249 GAATCTCAAGCACCGAAAGCTGATAACAATTTCAACAAAGAACAACAAAATG
1301 CTTTCTATGAAATCTTGAATATGCCTAACTTAAACGAAGAACAACGCAATGG
     HindIII
1353 TTTCATCCAAAGCTTAAAAGATGACCCAAGCCAAAGTGCTAACCTATTGTCA
1405 GAAGCTAAAAAGTTAAATGAATCTCAAGCACCGAAAGCGGATAACAAATTCA
1457 ACAAAGAACAACAAAATGCTTTCTATGAAATCTTACATTTACCTAACTTAAA
1509 CGAAGAACAACGCAATGGTTTCATCCAAAGCCTAAAAGATGACCCAAGCCAA
1561 AGCGCTAACCTTTTAGCAGAAGCTAAAAAGCTAAATGATGCTCAAGCACCAA
1613 AAGCTGACAACAAATTCAACAAAGAACAACAAAATGCTTTCTATGAAATTTT
1665 ACATTTACCTAACTTAACTGAAGAACAACGTAACGGCTTCATCCAAAGCCTT
          EcoRI  SmaI   BamHI  SalI   PstI    SphI    HindIII
1717 AAAGACGATCCGGGGAATTCCCGGGGATCCGTCGACCTGCAGGCATGCAAGC
1769 TTACTCCCCATCCCCTCCAGTAATGACCTCAGAACTCCATCTGGATTTGTTC
1821 AGAACGCTCGGTTGCCGCCGGGCGTTTTTTATTGGTGAGAATCGCAGCAACT
1873 TGTCGCGCCAATCGAGCCATGTCGTCGTCAACGACCCCCCATTCAAGAACAG
1925 CAAGCAGCATTGAGAACTTTGGAATCCAGTCCCTCTTCCACCTGCTGAGGGC
1977 AATAAGGGCTGCACGCGCACTTTTATCCGCCTCTGCTGCGCTCCGCCACCGT
2029 AGTTAAATTTATGGTTGGTTATGAAATGCTGGCAGAGACCCAGCGAGACCTG
2081 ACCGCAGAACAGGCAGCAGAGCGTTTGCGCGCAGTCAGCGATACCCCGGTTG
2133 ATAATCAGAAAAGCCCCAAAAACAGGAAGATTGTATAAGCAAATATTTAAAT
2185 TGTAAACGTTAATATTTGTTAAAATTCGCGTTAAATTTTGTTAAATCAGC
2237 TCATTTTTTAACCAATAGGCCGAAATCGGCAAAATCCCTTATAAATCAAAAG
2289 AATAGCCCGAGATAGGGTTGAGTGTTGTTCCAGTTTGGAACAAGAGTCCACT
2341 ATTAAAGAACGTGGACTCCAACGTCAAAGGGCGAAAAACCGTCTATCAGGGC
     DraIII
2393 GATGGCCCACTACGTGAACCATCACCCAAATCAAGTTTTTTGGGGTCGAGGT
2445 GCCGTAAAGCACTAAATCGGAACCCTAAAGGGAGCCCCGATTTAGAGCTTG
     NaeI
2497 ACGGGGAAAGCCGGCGAACGTGGCGAGAAAGGAAGGGAAGAAAGCGAAAGGA
2549 GCGGGCGCTAGGGCGCGAGCAAGTGTAGCGGTCACGCGCGCGTAACCACCAC
                                                    NruI
2601 ACCCGCCGCGCTTAATGCGCCGCTACAGGGCGCGTATCCATTTTCGCGAATC
2653 CGGAGTGTAAGAAATGAGTCTGAAAGAAAAAACACAATCTCTGTTTGCCAAC
2705 GCATTTGGCTACCCTGCCACTCACACCATTCAGGTGCGTCATATACTGACTG
2757 AAAACGCCCGCACCGTTGAAGCTGCCAGCGCGCTGGAGCAAGGCGACCTGAA
2809 ACGTATGGGCGAGTTGATGGCGGAGTCTCATGCCTCTATGCGCGATGATTTC
2861 GAAATCACCGTGCCGCAAATTGACACTCTGGTAGAAATCGTCAAAGCTGTGA
2913 TTGGCGACAAAGGTGGCGTACGCATGACCGGCGGCGGATTTGGCGGCTGTAT
2965 CGTCGCGCGTATCCCGGAAGAGCTGGTGCCTGCCGCACAGCAAGCTGTCGCT
3017 GAACAATATGAAGCAAAAACAGGTATTAAAGAGACTTTTTACGTTTGTAAAC
```

FIG. 14D

```
3069 CATCACAAGGAGCAGGACAGTGCTGAACGAAACTCCCGCACTGGCACCCGAT
3121 GGCAGCCGTACCGACTGTTCTGCCTCGCGCGTTTCGGTGATGACGGTGAAAA
3173 CCTCTGACACATGCAGCTCCCGGAGACGGTCACAGCTTGTCTGTAAGCGGAT
3225 GCCGGGAGCAGACAAGCCCGTCAGGGCGCGTCAGCGGGTGTTGGCGGGTGTC
3277 GGGGCGCAGCCATGACCCAGTCACGTAGCGATAGCGGAGTGTATACTGGCTT
                                                    Ndel
3329 AACTATGCGGCATCAGAGCAGATTGTACTGAGAGTGCACCATATGCGGTGTG
3381 AAATACCGCACAGATGCGTAAGGAGAAAATACCGCATCAGGCGCTCTTCCGC
3433 TTCCTCGCTCACTGACTCGCTGCGCTCGGTCGTTCGGCTGCGGCGAGCGGTA
3485 TCAGCTCACTCAAAGGCGGTAATACGGTTATCCACAGAATCAGGGGATAACG
3537 CAGGAAAGAACATGTGAGCAAAAGGCCAGCAAAAGGCCAGGAACCGTAAAAA
3589 GGCCGCGTTGCTGGCGTTTTTCCATAGGCTCCGCCCCCTGACGAGCATCAC
3641 AAAAATCGACGCTCAAGTCAGAGGTGGCGAAACCCGACAGGACTATAAAGAT
3693 ACCAGGCGTTTCCCCCTGGAAGCTCCCTCGTGCGCTCTCCTGTTCCGACCCT
3745 GCCGCTTACCGGATACCTGTCCGCCTTTCTCCCTTCGGGAAGCGTGGCGCTT
3797 TCTCATAGCTCACGCTGTAGGTATCTCAGTTCGGTGTAGGTCGTTCGCTCCA
3849 AGCTGGGCTGTGTGCACGAACCCCCCGTTCAGCCCGACCGCTGCGCCTTATC
3901 CGGTAACTATCGTCTTGAGTCCAACCCGGTAAGACACGACTTATCGCCACTG
3953 GCAGCAGCCACTGGTAACAGGATTAGCAGAGCGAGGTATGTAGGCGGTGCTA
4005 CAGAGTTCTTGAAGTGGTGGCCTAACTACGGCTACACTAGAAGGACAGTATT
4057 TGGTATCTGCGCTCTGCTGAAGCCAGTTACCTTCGGAAAAAGAGTTGGTAGC
4109 TCTTGATCCGGCAAACAAACCACCGCTGGTAGCGGTGGTTTTTTTGTTTGCA
4161 AGCAGCAGATTACGCGCAGAAAAAAAGGATCTCAAGAAGATCCTTTGATCTT
4213 TTCTACGGGGTCTGACGCTCAGTGGAACGAAAACTCACGTTAAGGGATTTTG
4265 GTCATGAGATTATCAAAAGGATCTTCACCTAGATCCTTTTAAATTAAAAAT
4317 GAAGTTTTAAATCAATCTAAAGTATATATGAGTAAACTTGGTCTGACAGTTA
4369 CCAATGCTTAATCAGTGAGGCACCTATCTCAGCGATCTGTCTATTTCGTTCA
4421 TCCATAGTTGCCTGACTCCCCGTCGTGTAGATAACTACGATACGGGAGGGCT
4473 TACCATCTGGCCCCAGTGCTGCAATGATACCGCGAGACCCACGCTCACCGGC
                                                    BglII
4525 TCCAGATTTATCAGCAATAAACCAGCCAGCCGGAAGGGCCGAGCGCAGAAGT
4577 GGTCCTGCAACTTTATCCGCCTCCATCCAGTCTATTAATTGTTGCCGGGAAG
4629 CTAGAGTAAGTAGTTCGCCAGTTAATAGTTTGCGCAACGTTGTTGCCATTGC
4681 TACAGGCATCGTGGTGTCACGCTCGTCGTTTGGTATGGCTTCATTCAGCTCC
4733 GGTTCCCAACGATCAAGGCGAGTTACATGATCCCCCATGTTGTGCAAAAAAG
                                                    PvuI
4785 CGGTTAGCTCCTTCGGTCCTCCGATCGTTGTCAGAAGTAAGTTGGCCGCAGT
4837 GTTATCACTCATGGTTATGGCAGCACTGCATAATTCTCTTACTGTCATGCCA
                                                    ScaI
4889 TCCGTAAGATGCTTTTCTGTGACTGGTGAGTACTCAACCAAGTCATTCTGAG
4941 AATAGTGTATGCGGCGACCGAGTTGCTCTTGCCCGGCGTCAACACGGGATAA
                                                    XmnI
4993 TACCGCGCCACATAGCAGAACTTTAAAAGTGCTCATCATTGGAAAACGTTCT
5045 TCGGGGCGAAAACTCTCAAGGATCTTACCGCTGTTGAGATCCAGTTCGATGT
5097 AACCCACTCGTGCACCCAACTGATCTTCAGCATCTTTTACTTTCACCAGCGT
5149 TTCTGGGTGAGCAAAAACAGGAAGGCAAAATGCCGCAAAAAAGGGAATAAGG
5201 GCGACACGGAAATGTTGAATACTCATACTCTTCCTTTTTCAATATTATTGAA
5253 GCATTTATCAGGGTTATTGTCTCATGAGCGGATACATATTTGAATGTATTTA
```

FIG. 14E

```
5305 GAAAAATAAACAAATAGGGGTTCCGCGCACATTTCCCCGAAAAGTGCCACCT
5357 GACGTCTAAGAAACCATTATTATCATGACATTAACCTATAAAAATAGGCGTA
                    AvaI
5409 TCACGAGGCCCTTTCGTCTTCAAGCCCGAGGTAACAAAAAAACAACAGCATA
5461 AATAACCCCGCTCTTACACATTCCAGCCCTGAAAAAGGGCATCAAATTAAAC
5513 CACACCTATGGTGTATGCATTTATTTGCATACATTCAATCAATTGTTATCTA
              NdeI                                                        ClaI
5565 AGGAAATACTTACATATGGTTCGTGCAAACAAACGCAACGAGGCTCTACGAA
         SphI   PvuII                                                    NdeI
5617 TCGATGCATGCAGCTGATTTCACTTTTTGCATTCTACAAACTGCATAACTCA
5669 TATGTAAATCGCTCCTTTTAGGTGGCACAAATGTGAGGCATTTTCGCTCTT
5721 TCCGGCAACCACTTCCAAGTAAAGTATAACACACTATACTTTATATTCATAA
5773 AGTGTGTGCTCTGCGAGGCTGTCGGCAGTGCCGACCAAAACCATAAAACCTT
5825 TAAGACCTTTCTTTTTTTACGAGAAAAAGAAACAAAAAAACCTGCCCTCT
5877 GCCACCTCAGCAAAGGGGGGTTTTGCTCTCGTGCTCGTTAAAAATCAGCAA
5929 GGGACAGGTAGTATTTTTGAGAAGATCACTCAAAAAATCTCCACCTTTAAA
5981 CCCTTGCCAATTTTTATTTTGTCCGTTTTGTCTAGCTTACCGAAAGCCAGAC
6033 TCAGCAAGAATAAAATTTTTATTGTCTTTCGGTTTTCTAGTGTAACGGACAA
6085 AACCACTCAAAATAAAAAGATACAAGAGAGGTCTCTCGTATCTTTTATTCA
6137 GCAATCGCGCCCGATTGCTGAACAGATTAATAATAGATTTAGCTTTTTATT
6189 TGTTGAAAAAGCTAATCAAATTGTTGTCGGGATCAATTACTGCAAAGTCTC
6241 GTTCATCCCACCACTGATCTTTTAATGATGTATTGGGGTGCAAAATGCCCAA
6293 AGGCTTAATATGTTGATATAATTCATCAATTCCTCTACTTCAATGCGGCAA
6345 CTAGCAGTACCAGCAATAAACGACTCCGCACCTGTACAAACCGGTGAATCAT
6397 TACTACGAGAGCGCCAGCCTTCATCACTTGCCTCCCATAGATGAATCCGAAC
6449 CTCATTACACATTAGAACTGCGAATCCATCTTCATGGTGAACCAAAGTGAAA
6501 CCTAGTTTATCGCAATAAAAACCTATACTCTTTTAATATCCCGACTGGCA
6553 ATGCCGGGATAGACTGTAACATTCTCACGCATAAAATCCCCTTTCATTTTCT
6605 AATGTAAATCTATTACCTTATTATTAATTCAATTCGCTCATAATTAATCCTT
6657 TTTCTTATTACGCAAAATGGCCCGATTTAAGCACACCCTTTATTCCGTTAAT
6709 GCGCCATGACAGCCATGATAATTACTAATACTAGGAGAAGTTAATAAATACG
6761 TAACCAACATGATTAACAATTATTAGAGGTCATCGTTCAAAATGGTATGCGT
6813 TTTGACACATCCACTATATATCCGTGTCGTTCTGTCCACTCCTGAATCCCAT
6865 TCCAGAAATTCTAGCGATTCCAGAAGTTTCTCAGAGTCGGAAAGTTGACC
                                                              BglII
6917 AGACATTACGAACTGGCACAGATGGTCATAACCTGAAGGAAGATCTGATTGC
6969 TTAACTGCTTCAGTTAAGACCGAAGCGCTCGTCGTATAACAGATGCGATGAT
7021 GCAGACCAATCAACATGGCACCTGCCATTGCTACCTGTACAGTCAAGGATGG
7073 TAGAAATGTTGTCGGTCCTTGCACACGAATATTACGCCATTTGCCTGCATAT
7125 TCAAACAGCTCTTCTACGATAAGGGCACAAATCGCATCGTGGAACGTTTGGG
7177 CTTCTACCGATTTAGCAGTTTGATACACTTTCTCTAAGTATCCACCTGAATC
7229 ATAAATCGGCAAATAGAGAAAATTGACCATGTGTAAGCGGCCAATCTGAT
                    XmnI
7281 TCCACCTGAGATGCATAATCTAGTAGAATCTCTTCGCTATCAAAATTCACTT
7333 CCACCTTCCACTCACCGGTTGTCCATTCATGGCTGAACTCTGCTTCCTCTGT
7385 TGACATGACACACATCATCTCAATATCCGAATAGGGCCCATCAGTCTGACGA
7437 CCAAGAGAGCCATAAACACCAATAGCCTTAACATCATCCCCATATTTATCCA
7489 ATATTCGTTCCTTAATTTCATGAACAATCTTCATTCTTTCTTCTAGTCAT
7541 TATTATTGGTCCATTCACTATTCTCATTCCCTTTTCAGATAATTTAGATTT
```

FIG.14F

```
7593 GCTTTTCTAAATAAGAATATTTGGAGAGCACCGTTCTTATTCAGCTATTAAT
7645 AACTCGTCTTCCTAAGCATCCTTCAATCCTTTTAATAACAATTATAGCATCT
7697 AATCTTCAACAAACTGGCCCGTTTGTTGAACTACTCTTTAATAAAATAATTT
7749 TTCCGTTCCCAATTCCACATTGCAATAATAGAAAATCCATCTTCATCGGCTT
7801 TTTCGTCATCATCTGTATGAATCAAATCGCCTTCTTCTGTGTCATCAAGGTT
7853 TAATTTTTTATGTATTTCTTTTAACAAACCACCATAGGAGATTAACCTTTTA
7905 CGGTGTAAACCTTCCTCCAAATCAGACAAACGTTTCAAATTCTTTTCTTCAT
7957 CATCGGTCATAAAATCCGTATCCTTTACAGGATATTTGCAGTTTCGTCAAT
8009 TGCCGATTGTATATCCGATTTATATTTATTTTTCGGTCGAATCATTTGAACT
8061 TTTACATTTGGATCATAGTCTAATTTCATTGCCTTTTTCCAAAATTGAATCC
8113 ATTGTTTTTGATTCACGTAGTTTTCTGTATTCTTAAAATAAGTTGGTTCCAC
8165 ACATACCAATACATGCATGTGCTGATTATAAGAATTATCTTTATTATTTATT
8217 GTCACTTCCGTTGCACGCATAAAACCAACAAGATTTTTATTAATTTTTTTAT
8269 ATTGCATCATTCGGCGAAATCCTTGAGCCATATCTGACAAACTCTTATTTAA
8321 TTCTTCGCCATCATAAACATTTTAACTGTTAATGTGAGAAACAACCAACGA
8373 ACTGTTGGCTTTTGTTTAATAACTTCAGCAACAACCTTTTGTGACTGAATGC
8425 CATGTTTCATTGCTCTCCTCCAGTTGCACATTGGACAAAGCCTGGATTTACA
8477 AAACCACACTCGATACAACTTTCTTTCGCCTGTTTCACGATTTTGTTTATAC
8529 TCTAATATTTCAGCACAATCTTTTACTCTTTCAGCCTTTTTAAATTCAAGAA
8581 TATGCAGAAGTTCAAAGTAATCAACATTAGCGATTTTCTTTTCTCTCCATGG
8633 TCTCACTTTTCCACTTTTTGTCTTGTCCACTAAAACCCTTGATTTTTCATCT
8685 GAATAAATGCTACTATTAGGACACATAATATTAAAAGAAACCCCATCTATT
8737 TAGTTATTTGTTTAGTCACTTATAACTTTAACAGATGGGGTTTTTCTGTGCA
8789 ACCAATTTTAAGGGTTTTCAATACTTTAAAACACATACATACCAACACTTCA
8841 ACGCACCTTTCAGCAACTAAAATAAAAATGACGTTATTTCTATATGTATCAA
                Xmnl
8893 GATAAGAAGAACAAGTTCAAACCATCAAAAAAGACACCTTTTCAGGTGC
8945 TTTTTTTATTTATAAACTCATTCCCTGATCTCGACTTCGTTCTTTTTTTAC
8997 CTCTCGGTTATGAGTTAGTTCAAATTCGTTCTTTTTAGGTTCTAAATCGTGT
9049 TTTCTTGGAATTGTGCTGTTTATCCTTTACCTTGTCTACAAACCCCTTAA
9101 AAACGTTTTAAAGGCTTTTAAGCCGTCTGTACGTTCCTTAAGG
```

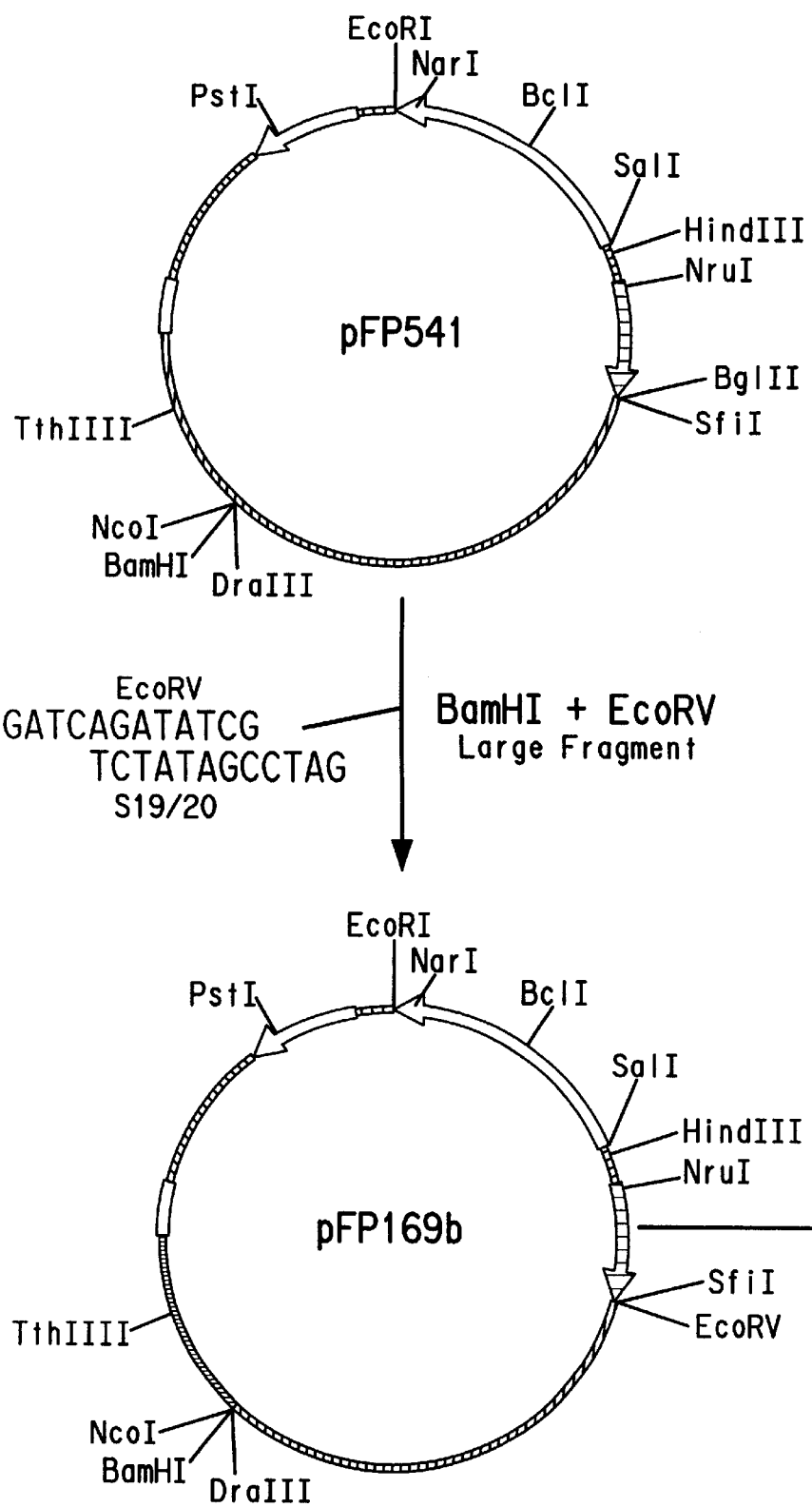

FIG. 16A

Oligonucleotide P1

```
GATCTCAAGGAGCCGGTCAAGGTGGTTACGGAGGTCTG            SEQ.NO. 84
     AGTTCCTCGGCCAGTTCCACCAATGCCTCCAGACCCTAG      SEQ.NO. 85
▶ SerGlnGlyAlaGlyGlnGlyGlyGlyLeuGly              SEQ.NO. 86
```

FIG. 16B

Oligonucleotide P2

```
GATCTCAAGGTGCTGGACGTGGTGGTCTTGGTGGTCAGGTGCCGGTGCCGCCCGCTGCCGGTGCTGGACAAGGTGGTTGG          SEQ.NO. 87
     AGTTCCACGACCTGCACCACCAGAACCACCAGTCCACGGCCACGGCGGGCGACGGCCACGACCTGTTCCACCAAACCCTAG    SEQ.NO. 88
▶ SerGlnGlyAlaGlyAlaGlyGlnGlyGlyGlyLeuGlyGlyAlaGlyAlaGlyAlaAlaAlaAlaAlaGlyGlyAlaGlyGlnGlyGlyGlyLeuGly  SEQ.NO. 89
```

FIG. 16C

Oligonucleotide P3

```
GATCTCAGGGAGCTGGTCAGGTGCCGGTGCTGCCGGAGGTGCCGGTCAGGTGGATACGGTGGACTTG              SEQ.NO. 90
     AGTCCCTCGACCAGTCCACGGCCACGACGGCCTCCACGGCCAGTCCACCTATGCCACCTGAACCTAG          SEQ.NO. 91
▶ SerGlnGlyAlaGlyGlnGlyAlaGlyAlaGlyAlaAlaAlaAlaAlaAlaGlyGlyAlaGlyGlnGlyGlyTyrGlyGlyLeuGly        SEQ.NO. 92
```

FIG. 16D

Oligonucleotide P4

```
GATCTCAGGGTGCTGTAGAGGTGGACAAGGTTGCCGGTGCTGGAGAGGTTACGGTGGTCTTG              SEQ.NO. 93
     AGTCCCACGACCATCTCCACCTGTTCCAACGGCCACGACCTCTCCAATGCCACCAGAACCTAG          SEQ.NO. 94
▶ SerGlnGlyAlaGlyArgGlyAlaGlyAlaGlyAlaAlaAlaAlaAlaGlyGlyAlaGlyGlnGlyGlyTyrGlyGlyLeuGly        SEQ.NO. 95
```

FIG. 17
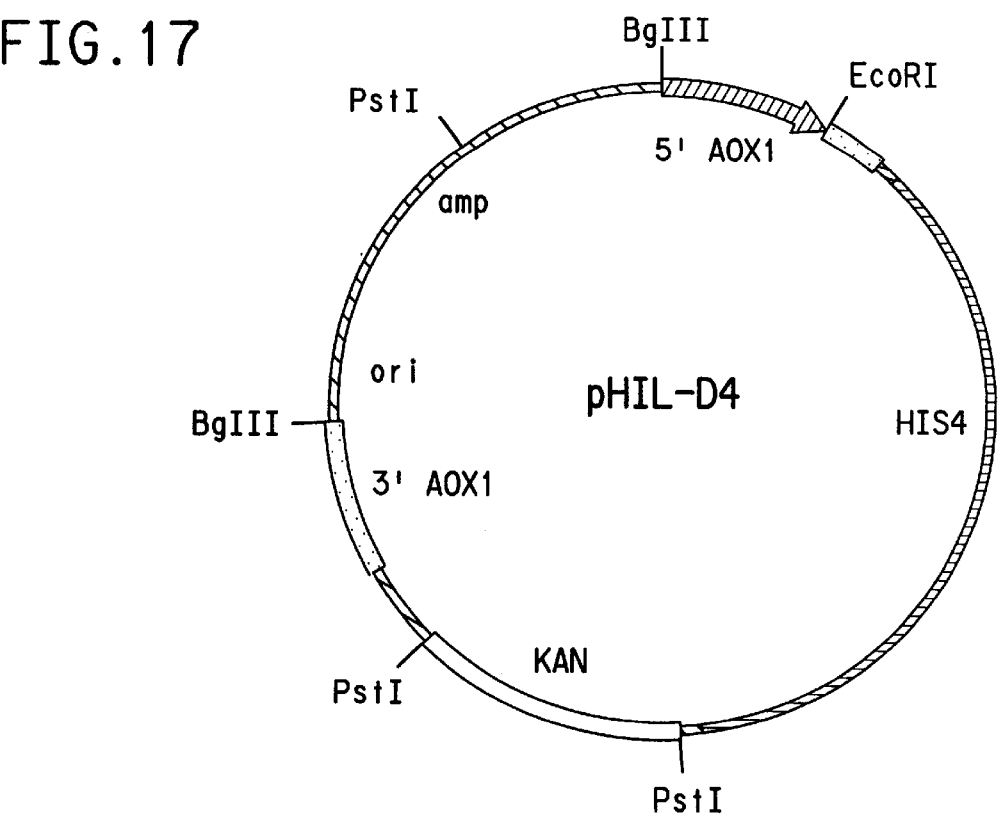
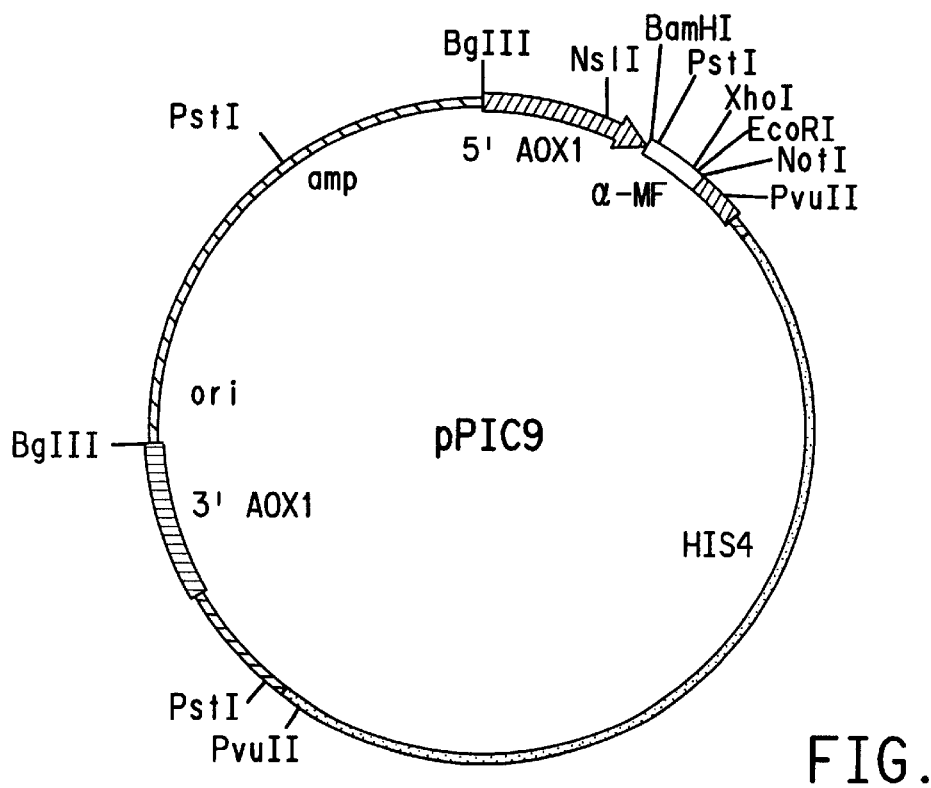
FIG. 18

FIG. 19

```
        NsiI
 750  ATGCATTGTCTCCACATTGTATGCTTCCAAGATTCTGGTGGGAATACTGCTGATA

805  GCCTAACGTTCATGATCAAAATTTAACTGTTCTAACCCCTACTTGACAGCAATAT

860  ATAAACAGAAGGAAGCTGCCCTGTCTTAAACCTTTTTTTTATCATCATTATTAG

915  CTTACTTTCATAATTGCGACTGGTTCCAATTGACAAGCTTTTGATTTTAACGACT

970  TTTAACGACAACTTGAGAAGATCAAAAAACAACTAATTATTCGAAACGATGAGAT
                                                   1▶ MetArgP
1025  TTCCTTCAATTTTTACTGCAGTTTTATTCGCAGCATCCTCCGCATTAGCTGCTCC
   3▶ heProSerIlePheThrAlaValLeuPheAlaAlaSerSerAlaLeuAlaAlaPr

1080  AGTCAACACTACAACAGAAGATGAAACGGCACAAATTCCGGCTGAAGCTGTCATC
  21▶ oValAsnThrThrThrGluAspGluThrAlaGlnIleProAlaGluAlaValIle

1135  GGTTACTCAGATTTAGAAGGGGATTTCGATGTTGCTGTTTTGCCATTTTCCAACA
  40▶ GlyTyrSerAspLeuGluGlyAspPheAspValAlaValLeuProPheSerAsnS

1190  GCACAAATAACGGGTTATTGTTTATAAATACTACTATTGCCAGCATTGCTGCTAA
  58▶ erThrAsnAsnGlyLeuLeuPheIleAsnThrThrIleAlaSerIleAlaAlaLy

EcoRI
1245  AGAAGAAGGGGTATCTCTCGAGAAAAGAGAGGCTGAAGCTTACGTAGAATTCCCT
  76▶ sGluGluGlyValSerLeuGluLysArgGluAlaGluAlaTyrValGluPhe  SEQ.NO. 97
        NotI
1300  AGGGCGGCCGCGAATTAATTCGCCTTAGACATGACTGT  SEQ.NO. 96
```

RECOMBINANTLY PRODUCED SPIDER SILK

This application is filed under 35 USC 371 as the national stage of International Application PCT/US94/06689 Jun. 15, 1994, a continuation-in-part of U.S. application Ser. No. 08/077,600, filed Jun. 15, 1993, now abandoned, and claims priority under 35 USC 120 as a continuation-in-part to U.S. application Ser. No. 08/077,600, filed Jun. 15, 1993, now abandoned.

FIELD OF THE INVENTION

The invention relates to novel spider silk protein analogs derived from the amino acid consensus sequence of repeating units found in the natural spider dragline of *Nephila clavipes*. More specifically, synthetic spider dragline has been produced from *E. coli* and *Bacillus subtilis* recombinant expression systems wherein expression from *E. coli* is at levels greater than 1 mg full-length polypeptide per gram of cell mass.

BACKGROUND

Ever increasing demands for materials and fabrics that are both light-weight and flexible without compromising strength and durability has created a need for new fibers possessing higher tolerances for such properties as elasticity, denier, tensile strength and modulus. The search for a better fiber has led to the investigation of fibers produced in nature, some of which possess remarkable qualities. The virtues of natural silk produced by *Bombyx mori* (silk worm) have been well known for years but it is only recently that other naturally produced silks have been examined.

Spider silks have been demonstrated to have several desirable characteristics. The orb-web-spinning spiders can produce silk from six different types of glands. Each of the six fibers has different mechanical properties. However, they all have several features in common. They are (i) composed predominantly or completely of protein; (ii) undergo a transition from a soluble to an insoluble form that is virtually irreversible; (iii) composed of amino acids dominated by alanine, serine, and glycine and have substantial quantities of other amino acids, such as glutamine, tyrosine, leucine, and valine. The spider dragline silk fiber has been proposed to consist of pseudocrystaline regions of antiparallel, β-sheet structure interspersed with elastic amorphous segments.

The spider silks range from those displaying a tensile strength greater than steel (7.8 vs 3.4 G/denier) and those with an elasticity greater than wool, to others characterized by energy-to-break limits that are greater than KEVLAR® ($1 \times 10^5$ vs $3 \times 10^4$ JKG-1). Given these characteristics spider silk could be used as a light-weight, high strength fiber for various textile applications.

Considerable difficulty has been encountered in attempting to solubilize and purify natural spider silk while retaining the molecular-weight integrity of the fiber. The silk fibers are insoluble except in very harsh agents such as LiSCN, LiClO4, or 88% (vol/vol) formic acid. Once dissolved, the protein precipitates if dialyzed or if diluted with typical buffers. Another disadvantage of spider silk protein is that only small amounts are available from cultivated spiders, making commercially useful quantities of silk protein unattainable at a reasonable cost. Additionally, multiple forms of spider silks are produced simultaneously by any given spider. The resulting mixture has less application than a single isolated silk because the different spider-silk proteins have different properties and, due to solubilization problems, are not easily separated by methods based on their physical characteristics. Hence the prospect of producing commercial quantities of spider silk from natural sources is not a practical one and there remains a need for an alternate mode of production. The technology of recombinant genetics provides one such mode.

By the use of recombinant DNA technology it is now possible to transfer DNA between different organisms for the purposes of expressing desired proteins in commercially useful quantities. Such transfer usually involves joining appropriate fragments of DNA to a vector molecule, which is then introduced into a recipient organism by transformation. Transformants are selected by a known marker on the vector, or by a genetic or biochemical screen to identify the cloned fragment. Vectors contain sequences that enable autonomous replication within the host cell, or allow integration into a chromosome in the host.

If the cloned DNA sequence encodes a protein, a series of events must occur to obtain synthesis of this foreign protein in an active form in the host cell. Promoter sequences must be present to allow transcription of the gene by RNA polymerase, and a ribosome binding site and initiation codon must be present in the transcribed mRNA for translation by ribosomes. These transcriptional and translational recognition sequences are usually optimized for effective binding by the host RNA polymerase and ribosomes, and by the judicious choice of vectors, it is often possible to obtain effective expression of many foreign genes in a host cell.

While many of the problems of efficient transcription and translation have been generally recognized and for the most part, overcome, the synthesis of fiber-forming foreign polypeptides containing high numbers of repeating units poses unique problems. Genes encoding proteins of this type are prone to genetic instability due to the repeating nucleic acid sequences. Ideally, they encode proteins of high molecular weight, consisting of at least 800 amino acid residues, and generally with restricted amino acid compositions. While *E. coli* produces endogenous proteins in excess of 1000 residues, production of long proteins of restricted amino acid composition appears to place an unbalanced strain on the biosynthetic system, resulting in the production of truncated products, probably due to abortive translation.

In spite of the above mentioned difficulties, recombinant expression of fiber forming proteins is known in the art. Chatellard et al., *Gene*, 81, 267, (1989) teach the cloning and expression of the trimeric fiber protein of human adenovirus type 2 from *E. coli*. The gene expression system relied upon bacteriophage T7 RNA polymerase and optimal gene expression was obtained at 30° C. where the foreign protein attained levels of 1% of total host protein.

Goldberg et al., *Gene*, 80, 305, (1989) disclose the cloning and expression in *E. coli* of a synthetic gene encoding a collagen analog (poly (Gly-Pro-Pro)). The largest DNA insert was on the order of 450 base pairs and it was suggested that large segments of highly-repeated DNA may be unstable in *E. coli*.

Ferrari et al. (WO 8803533) disclose methods and compositions for the production of polypeptides having repetitive oligomeric units such as those found in silk-like proteins and elastin-like proteins by the expression of synthetic structural genes. The DNA sequences of Ferrari encode peptides containing an oligopeptide repeating unit which contains at least 3 different amino acids and a total of 4–30 amino acids, there being at least 2 repeating units in the peptide and at least 2 identical amino acids in each repeating unit.

Cappello et al. (WO 9005177) teach the production of a proteinaceous polymer from transformed prokaryotic hosts comprising strands of repeating units which can be assembled into aligned strands and DNA sequences encoding the same. The repeating units are derived from natural polymers such as fibroin, elastin, keratin or collagen.

The cloning and expression of silk-like proteins is also known. Ohshima et al., *Proc. Natl. Acad. Sci. U.S.A.*, 74, 5363, (1977) reported the cloning of the silk fibroin gene complete with flanking sequences of *Bombyx mori* into *E. coli*. Petty-Saphon et al. (EP 230702) disclose the recombinant production of silk fibroin and silk sericin from a variety of hosts including *E. coli*, *Saccharomyces cerevisiae*, *Pseudomonas sp Rhodopseudomonas sp*, *Bacilus sp*, and *Streptomyces sp*. In the preferred embodiments the expression of silk proteins derived from *Bombyx mori* is discussed.

Progress has also been made in the the cloning and expression of spider silk proteins. Xu et al., *Proc. Natl. Acad. Sci. U.S.A.*, 87, 7120, (1990) report the determination of the sequence for a portion of the repetitive sequence of a dragline silk protein, Spidroin 1, from the spider *Nephila clavipes*, based on a partial cDNA clone. The repeating unit is a maximum of 34 amino acids long and is not rigidly conserved. The repeat unit is composed of two different segments: (i) a 10 amino acid segment dominated by a polyalanine sequence of 5–7 residues; (ii) a 24 amino acid segment that is conserved in sequence but has deletions of multiples of 3 amino acids in many of the repeats. The latter sequence consists predominantly of GlyXaaGly motifs, with Xaa being alanine, tyrosine, leucine, or glutamine. The codon usage for this DNA is highly selective, avoiding the use of cytosine or guanine in the third position.

Hinman and Lewis, *J. Biol. Chem.* 267, 19320 (1992) report the sequence of a partial cDNA clone encoding a portion of the repeating sequence of a second fibroin protein, Spidroin 2, from dragline silk of *Nephila clavipes*. The repeating unit of Spidroin 2 is a maximum of 51 amino acids long and is also not rigidly conserved. The frequency of codon usage of the Spidroin 2 cDNA is very similar to Spidroin 1.

Lewis et al. (EP 452925) disclose the expression of spider silk proteins including protein fragments and variants, of *Nephila clavipes* from transformed *E. coli*. Two distinct proteins were independently identified and cloned and were distinguished as silk protein 1 ((Spidroin 1) and silk protein 2 (Spidroin 2).

Lombardi et al. (WO 9116351) teach the production of recombinant spider silk protein comprising an amorphous domain or subunit and a crystalline domain or subunit where the domain or subunit refers to a portion of the protein containing a repeating amino acid sequence that provides a particular mechanostructural property.

The above mentioned expression systems are useful for the production of recombinant silks and silk variants, however all rely on the specific cloned gene of a silk producing organism. One detrimental effect of such systems is that codon usage is not optimized for the production of foreign proteins in a recombinant host. It is well known in the art that expression of a foreign gene is more efficient if codons not favored by the organism in which expression is desired are avoided. Foreign genes cloned into recombinant hosts often rely on a codon usage not typically found in the host. This often results in poor yields of foreign protein.

There remains a need therefore for a method to produce a spider silk protein in commercially useful quantities. It is the object of the present invention to meet such need by providing novel DNA sequences encoding variants of consensus sequences derived from spider silk proteins capable of being expressed in a foreign host having the ability to produce synthetic proteins in commercially useful amounts of 1% to 30% of total host protein.

SUMMARY OF THE INVENTION

The present invention provides novel synthetic spider dragline variant proteins produced by a process comprising the steps of:designing a DNA monomer sequence of between about 50 bp and 1000 bp which codes for an polypeptide monomer consisting of a variant of a consensus sequence derived from the fiber forming regions of spider dragline protein; assembling the DNA monomer; polymerizing the DNA monomer to form a synthetic gene encoding a full length silk variant protein; transforming a suitable host cell with a vector containing the synthetic gene; expressing the DNA polymer whereby the protein encoded by the DNA polymer is produced at levels greater than 1 mg full-length protein per gram of cell mass and; recovering the protein in a useful form.

The present invention provides novel plasmids containing DNA compositions encoding spider silk variant proteins and novel transformed host cells containing these plasmids which are capable of expressing the silk variant protein at levels greater than 1 mg full-length polypeptide per gram of cell mass.

Also included in the scope of the invention are transformed host cells capable of secreting full-length spider dragline protein analogs into the cell growth medium.

In a preferred embodiment, an artificial gene is constructed to encode an analog of a spider silk protein, one of the proteins of the dragline fiber of *Nephila clavipes*. Means are provided whereby such an artificial gene can be assembled and polymerized to encode a protein of approximately the same length as the natural protein. Further, means are provided whereby such an artificial gene can be expressed in a regulated fashion in a bacterial host, producing large quantities of its protein product. This protein product can be prepared in purified form suitable for forming into a fiber. While the subject of the current invention is a spider silk variant protein, it should be understood that the invention can be extended to encompass other highly repetitive fiber forming proteins or variant forms of such natural proteins.

The present invention provides methods for the production of commercially useful quantities of spider silk proteins in microorganisms, using recombinant DNA technology. Microbial methods of production of such proteins, would provide several advantages. For example microbial sources would provide the basis for production of fiber-forming proteins in large quantities at low enough cost for commercial applications. Microbial hosts would allow the application of recombinant DNA technology for the construction and production of variant forms of fiber-forming proteins, as well as novel proteins that could extend the utility of such fibers. Furthermore, microbial production would permit the rapid preparation of samples of variant proteins for testing. Such proteins would be free of other proteins found in the natural fiber, allowing the properties of the individual proteins to be studied separately.

BRIEF DESCRIPTION OF THE DRAWINGS, SEQUENCE LISTING AND BIOLOGICAL DEPOSITS

FIG. 1 illustrates the amino acid sequence (SEQ ID NO.:19) of natural spider dragline protein Spidroin 1 as disclosed by Xu et al., *Proc. Natl. Acad. Sci. U.S.A.*, 87, 7120, (1990).

FIG. 2A illustrates the amino acid sequence (SEQ ID NO:20) of the monomer of the spider silk DP-1A.9 analogue (SEQ ID NO:80).

FIG. 2B illustrates the amino acid sequence (SEQ ID NO:21) of the polymer of the spider silk DP-1A.9 analogue (SEQ ID NO:80).

FIG. 3A illustrates the amino acid sequence (SEQ ID NO:22) of the monomer of the spider silk DP-1B.9 analogue (SEQ ID NO:81).

FIG. 3B illustrates the amino acid sequence (SEQ ID NO:23) of the polymer of the spider silk DP-1B.9 analogue (SEQ ID NO:81).

FIG. 4A illustrates the synthetic oligonucleotide L (SEQ ID Nos. 24–26) used in the construction of the DNA monomer for DP-1 protein expression.

FIG. 4B illustrates the synthetic oligonucleotide M1 (SEQ ID Nos. 27–29) used in the construction of the DNA monomer for DP-1 protein expression.

FIG. 4C illustrates the synthetic oligonucleotide M2 (SEQ ID Nos. 30–32) used in the construction of the DNA monomer for DP-1 protein expression.

FIG. 4D illustrates the synthetic oligonucleotide S (SEQ ID Nos. 33–35) used in the construction of the DNA monomer for DP-1 protein expression.

FIG. 7A illustrates the double stranded synthetic oligonucleotide A (SEQ ID Nos. 41–43) used in the construction of the DNA monomer for DP-2 protein expression.

FIG. 7B illustrates the double stranded synthetic oligonucleotide B (SEQ ID Nos. 44–46) used in the construction of the DNA monomer for DP-2 protein expression.

FIG. 7C illustrates the double stranded synthetic oligonucleotide C (SEQ ID Nos. 47–49) used in the construction of the DNA monomer for DP-2 protein expression.

FIG. 7D illustrates the double stranded synthetic oligonucleotide D (SEQ ID Nos. 50–52) used in the construction of the DNA monomer for DP-2 protein expression.

FIG. 7E illustrates the double stranded synthetic oligonucleotide E (SEQ ID Nos. 53–55) used in the construction of the DNA monomer for DP-2 protein expression.

FIG. 7F illustrates the double stranded synthetic oligonucleotide F (SEQ ID Nos. 56–58) used in the construction of the DNA monomer for DP-2 protein expression.

FIG. 8 illustrates the amino acid sequence (SEQ ID NO.:59) of the natural spider silk protein Spidroin 2 as described by Lewis et al. (EP 452925).

FIG. 9A illustrates the amino acid sequence of the amino acid monomer (SEQ ID NO:60) of the spider dragline protein 2 analog DP-2A (SEQ ID NO.:83).

FIG. 9B illustrates the amino acid sequence of the amino acid polymer (SEQ ID NO:61) of the spider dragline protein 1 analog DP-2A (SEQ ID NO.:83).

FIG. 10A illustrates the amino acid sequence of the amino acid monomer (SEQ ID NO:62) of the spider dragline protein 1 analog DP-1B.16 (SEQ ID NO.:82).

FIG 10B illustrates the amino acid sequence of the amino acid polymer (SEQ ID NO:63) of the spider dragline protein 1 analog DP-1B.16 (SEQ ID NO.:82).

FIG. 11A illustrates the double stranded synthetic oligonucleotide 1 (SEQ ID Nos. 64–66) used to construct the synthetic genes encoding DP-1B.16 (SEQ ID NO:82).

FIG. 11B illustrates the double stranded synthetic oligonucleotide 2 (SEQ ID Nos. 67–69) used to construct the synthetic genes encoding DP-1B.16 (SEQ ID NO:82).

FIG. 11C illustrates the double stranded synthetic oligonucleotide 3 (SEQ ID Nos. 70–72) used to construct the synthetic genes encoding DP-1B.16 (SEQ ID NO:82).

FIG. 11D illustrates the double stranded synthetic oligonucleotide 4 (SEQ ID Nos. 63–75) used to construct the synthetic genes encoding DP-1B.16 (SEQ ID NO:82).

FIG. 13A is a plasmid map of plasmid pA126i. FIG. 13B illustrates the full sequence of plasmid pA126i (SEQ ID NO:78).

FIG. 13C is a continuation from FIG. 13B of the full sequence of plasmid pA126i (SEQ ID NO:78).

FIG. 13D is a continuation from 13C of the full sequence of plasmid pA126i (SEQ ID NO:78).

FIG. 14A is a plasmid map of pBE346.

FIG. 14B illustrates the complete DNA sequence (SEQ ID NO:79) of the plasmid pBE346.

FIG. 14C is a continuation from FIG. 14B of the complete DNA sequence (SEQ ID NO:79) of the plasmid pBE346.

FIG. 14D is a continuation from FIG. 14C of the complete DNA sequence (SEQ ID NO:79) of the plasmid pBE346.

FIG. 14E is a continuation from FIG. 14D of the complete DNA sequence (SEQ ID NO:79) of the plasmid pBE346.

FIG. 14F is a continuation from FIG. 14E of the complete DNA sequence (SEQ ID NO:79) of the plasmid pBE346.

FIG. 15A illustrates the construction of plasmid pFP169b from plasmid pFP541.

FIG. 16A illustrates the synthetic double stranded oligonucleotide P1 (SEQ ID Nos:84–86) used to construct the synthetic genes encoding DP-1B.33.

FIG. 16B illustrates the synthetic double stranded oligonucleotide P2 (SEQ ID Nos:87–89) used to construct the synthetic genes encoding DP-1B.33.

FIG. 16C illustrates the synthetic double stranded oligonucleotide P3 (SEQ ID Nos:90–92) used to construct the synthetic genes encoding DP-1B.33.

FIG. 16D illustrates the synthetic double stranded oligonucleotide P4 (SEQ ID Nos:93–95) used to construct the synthetic genes encoding DP-1B.33.

FIG. 17 is a plasmid map of plasmid pHIL-D4, used to construct vectors for intracellular protein expression in *Pichia pastoris*.

FIG. 18 is a plasmid map of plasmid pPIC9, used to construct vectors for extracellular protein production in *P. pastoris*.

FIG. 19 illustrates the DNA sequence of a portion of plasmid pFO734, an intermediate in the construction of vectors for extracellular protein production in *P. pastoris*.

Figure 5:
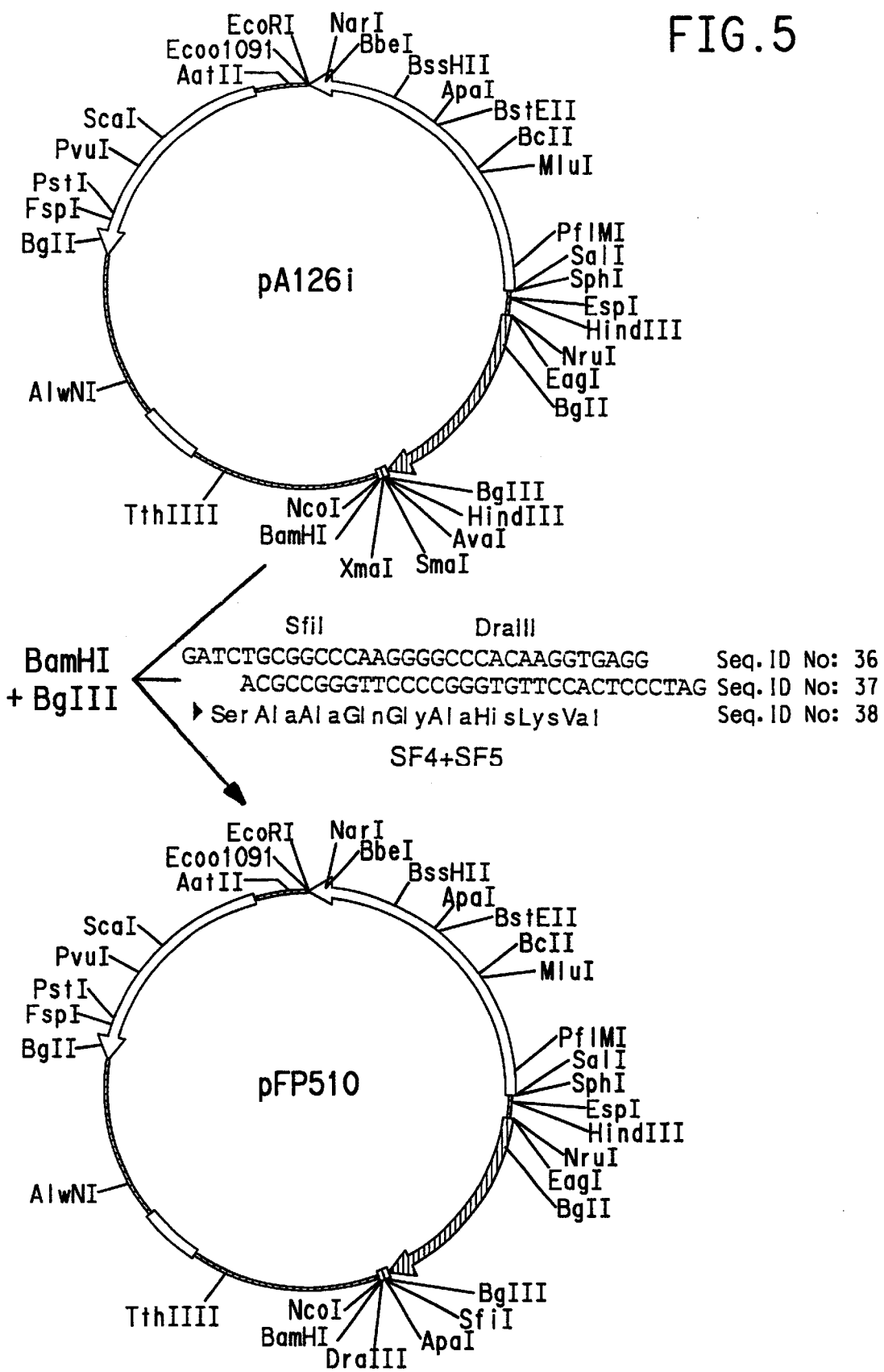
FIG. 5 is a plasmid map illustrating the construction of plasmid pFP510 from pA126i. Plasmid pFP510 is used to construct plasmids for the assembly and polymerization of DNA monomers and genes encoding DP-1A analogs.

Applicants have provided sequence listings 1–107 in conformity with "Rules for the standard representation of nucleotide and amino acid sequence in patent applications" (Annexes I and II to the Decision of the President of the EPO, published in Supplement No. 2 to OJ EPO 12/1992).

Applicants have made the following biological deposits under the terms of the Budapest Treaty.

| Deposit or Identification Reference | ATCC Designation | Deposit Date |
|---|---|---|
| Escherichia coli, FP 3227 | 69326 | 15 June 1993 |
| Escherichia coli, FP 2193 | 69327 | 15 June 1993 |
| Escherichia coli, FP 3350 | 69328 | 15 June 1993 |

As used herein, the designation "ATCC" refers to the American Type Culture Collection depository located in Manassas, Va. at 10801 University Blvd., Manassas, Va. 20110-2209, U.S.A. The "ATCC No." is the accession number to cultures on deposit at the ATCC.

DETAILED DESCRIPTION OF THE INVENTION

The following definitions are used herein and should be referred to for interpretation of the claims and the specification.

As used herein, the terms "promoter" and "promoter region" refer to a sequence of DNA, usually upstream of (5' to) the protein coding sequence of a structural gene, which controls the expression of the coding region by providing the recognition for RNA polymerase and/or other factors required for transcription to start at the correct site. Promoter sequences are necessary but not always sufficient to drive the expression of the gene.

A "fragment" constitutes a fraction of the DNA sequence of the particular region.

"Nucleic acid" refers to a molecule which can be single stranded or double stranded, composed of monomers (nucleotides) containing a sugar, phosphate and either a purine or pyrimidine. In bacteria, lower eukaryotes, and in higher animals and plants, "deoxyribonucleic acid" (DNA) refers to the genetic material while "ribonucleic acid" (RNA) is involved in the translation of the information from DNA into proteins.

The terms "peptide", "polypeptide" and "protein" are used interchangeably.

"Regulation" and "regulate" refer to the modulation of gene expression controlled by DNA sequence elements located primarily, but not exclusively upstream of (5' to) the transcription start of a gene. Regulation may result in an all or none response to a stimulation, or it may result in variations in the level of gene expression.

The term "coding sequence" refers to that portion of a gene encoding a protein, polypeptide, or a portion thereof, and excluding the regulatory sequences which drive the initiation of transcription. The coding sequence may constitute an uninterrupted coding region or it may include one or more introns bounded by appropriate splice junctions. The coding sequence may be a composite of segments derived from different sources, naturally occurring or synthetic.

The term "construction" or "construct" refers to a plasmid, virus, autonomously replicating sequence, phage or nucleotide sequence, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein, "transformation" is the acquisition of new genes in a cell by the incorporation of nucleic acid.

The term, "operably linked" refers to the chemical fusion of two fragments of DNA in a proper orientation and reading frame to lead to the transcription of functional RNA.

The term "expression" as used herein is intended to mean the transcription and translation to gene product from a gene coding for the sequence of the gene product. In the expression, a DNA chain coding for the sequence of gene product is first transcribed to a complementary RNA which is often a messenger RNA and, then, the thus transcribed messenger RNA is translated into the above-mentioned gene product if the gene product is a protein.

The term "translation initiation signal" refers to a unit of three nucleotides (codon) in a nucleic acid that specifies the initiation of protein synthesis.

The term "signal peptide" refers to an amino terminal polypeptide preceding the secreted mature protein. The signal peptide is cleaved from and is therefore not present in the mature protein. Signal peptides have the function of directing and trans-locating secreted proteins across cell membranes. The signal peptide is also referred to as signal sequence.

The term "mature protein" refers to the final secreted protein product without any part of the signal peptide attached.

The term "plasmid" or "vector" as used herein refers to an extra-chromosomal element often carrying genes which are not part of the central metabolism of the cell, and usually in the form of circular double-stranded DNA molecules.

The term "restriction endonuclease" refers to an enzyme which catalyzes hydrolytic cleavage within a specific nucleotide sequence in double-stranded DNA.

The term "compatible restriction sites" refers to different restriction sites that when cleaved yield nucleotide ends that can be ligated without any additional modification.

The-term "suitable promoter" will refer to any eukaryotic or prokaryotic promoter capable of driving the expression of a synthetic spider silk variant gene.

The term "spider silk variant protein" will refer to a designed protein, the amino acid sequence of which is based on repetitive sequence motifs and variations thereof that are found in a known a natural spider silk.

The term "full length variant protein" will refer to any spider silk variant protein encoded by a synthetic gene which has been constructed by the assembly and polymerization of a DNA monomer.

The term "DNA monomer" will refer to a DNA fragment consisting of between 300 and 400 bp which encodes one or more repeating amino acid sequences of a spider silk variant protein. Examples of DNA monomers suitable for the present invention are illustrated in FIGS. 2, 3, 9 and 10.

The term "peptide monomer", "polypeptide monomer" or "amino acid monomer" will refer to the amino acid sequence encoded by a DNA monomer.

The term "commercial quantities" will refer to quantities of recombinantly produced desired proteins where at least 1% of the total protein produced by a microbial culture is the desired protein.

The term "desired protein" will refer to any protein considered a valuable product to be obtained from genetically engineered bacteria.

The term "DP-1 analog" will refer to any spider silk variant derived from the amino acid sequence of the natural Protein 1 (Spidroin 1) of *Nephila calvipes* as illustrated in FIG. 1.

The term "DP-2 analog" will refer to any spider silk variant derived from the amino acid sequence of the natural Protein 2 (Spidroin 2) of *Nephila calvipes* as illustrated in FIG. 8.

As used herein the following abbreviations will be used to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamine acid | Glu | E |
| Glutamine or glutamic acid | Glx | Z |
| Glycine | Gly | G |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The present invention also provides novel DNA sequences encoding spider silk protein variants that are suitable for expression of commercial quantities of silk protein in a recombinant host.

It will be appreciated that the advantages of such a protein and such a method are many. Spider silk, especially dragline silk, has a tensile strength of over, 200 ksi with an elasticity of nearly 35%, which makes it more difficult to break than either KEVLAR or steel. When spun into fibers, spider silk of the present invention may have application in the bulk clothing industries as well as being applicable for certain kinds of high strength uses such as rope, surgical sutures, flexible tie downs for certain electrical components and even as a biomaterial for implantation (e.g., artificial ligaments or aortic banding). Additionally these fibers may be mixed with various plastics and/or resins to prepare a fiber-reinforced plastic and/or resin product. Furthermore, since spider silk is stable up to 100° C., these fibers may be used to reinforce thermal injected plastics. These proteins may also be of value in the form of films or coatings. It will be appreciated by one of skill in the art that the properties of the silk fibers may be altered by altering the amino acid sequence of the protein.

The present invention provides a method for the production of analogs of natural spider silk proteins and variants using recombinant DNA technology. The method consists of (1) the design of analog protein sequences based on the amino acid sequence of the fiber forming regions of natural proteins; (2) the design of DNA sequences to encode such analog protein sequences, based on a DNA monomer of at least 50 bp with minimal internal repetitiveness, and making preferential use of codons matched to the preferences of a specific host organism; (3) assembly of the DNA monomer from cloned synthetic oligonucleotides; (4) polymerization of the DNA monomer to lengths of at least 800 bp, and preferably to lengths approximating the length of the gene encoding the natural protein; (5) inserting the polymerized artificial gene into an appropriate vector able to replicate in the host organism, in such a manner. that the gene is operably linked to expression signals whereby its expression can be regulated; (6) producing the protein in the above mentioned microbial host carrying such an expression vector; (7) purifying the protein from the biomass and preparing it in a form suitable for forming into fibers, films, or coatings.

The expression of the desired silk variant protein in *Escherichia coli* is preferred since this host reliably produces high levels of foreign protein and the art is replete with suitable transformation and expression vectors. However, it is not outside the scope of the invention to provide alternative hosts and particularly hosts that facilitate the secretion of the desired protein into the growth medium. Such alternative hosts may include but are not limited to *Bacillus subtilis, Saccharomyces cerevisiae, Schizosaccharomyces pombe, Pichia pastoris*, Aspergillus spp., Hansenula spp., and Streptomyces spp. The expression host preferred for the secretion of silk variant protein is *Bacillus subtilis*.

The present invention provides a variety of plasmids or vectors suitable for the cloning of portions of the DNA required for the assembly and expression of the silk variant protein gene in *E. coli*. Suitable vectors for construction contain a selectable marker and sequences allowing autonomous replication or chromosomal integration. Additionally, suitable vectors for expression contain sequences directing transcription and translation of the heterologous DNA fragment. These vectors comprise a region 5' of the heterologous DNA fragment which harbors transcriptional initiation controls, and optionally a region 3' of the DNA fragment which controls transcriptional termination. It is most preferred when both control regions are derived from genes homologous to *E. coli* although it is to be understood that such control regions need not be derived from the genes native to the specific species chosen as a production host. Suitable vectors can be derived, for example, from a bacteria, a virus (such as bacteriophage T7 or a M-13 derived phage), a cosmid, a yeast or a plant. Protocols for obtaining and using such vectors are known to those in the art. (Sambrook et al., Molecular Cloning: A Laboratory Manual—volumes 1,2,3 (Cold Spring Harbor Laboratory: Cold Spring Harbor, N.Y., 1989))

Examples of bacteria-derived vectors include plasmid vectors such as pBR322, pUC19, pSP64, pUR278 and pORF1. Illustrative of suitable viral vectors are those derived from phage, vaccinia, retrovirus, baculovirus, or a bovine papilloma virus. Examples of phage vectors include λ⁺, λEMBL3, 12001, λgt10, λgt11, Charon 4a, Charon 40, and λZAP/R. pXB3 and pSC11 are exemplary of vaccinia vectors (Chakrabarti et al., *Molec. Cell. Biol.* 5:3401–9 (1985) and Mackett et al., *J. Virol.* 49:857864 (1984). An example of a filamentous phage vector is an M13-derived vector like M13mp18, and M13mp19.

For the expression of spider silk variant proteins in *E. coli* bacteria-derived vectors are preferred where plasmids derived from pBR322 are most preferred.

Optionally it may be desired to produce the silk variant protein as a secretion product of a transformed host, such as B. subtilis. Secretion of desired proteins into the growth media has the advantage of simplified and less costly purification procedures. It is well known in the art that secretion signal sequences are often useful in facilitating the active transport of expressible proteins across cell membranes. The creation of a transformed Bacillus host capable of secretion may be accomplished by the incorporation of a DNA sequence that codes for a secretion signal functional in the Bacillus production host on the expression cassette, between the expression-controlling DNA and the DNA encoding the silk variant protein and in reading frame with the latter. Examples of vectors enabling the secretion of a number of different heterologous proteins by B. subtilis have been taught and are described in Nagarajan et al., U.S. Pat. No. 4,801,537; Stephens et al., U.S. Pat. No. 4,769,327; and Biotechnology Handbook 2, Bacillus, C. R. Harwood, Ed., Plenum Press, New York (1989).

Secretion vectors of this invention include a regulatable promoter sequence which controls transcription, a sequence for a ribosome binding site which controls translation, and a sequence for a signal peptide which enables translocation of the peptide through the bacterial membrane and the cleavage of the signal peptide from the mature protein. Suitable vectors will be those which are compatible with the bacterium employed. For example, for B. subtilis such suitable vectors include E. coli-B. subtilis shuttle vectors. They will have compatible regulatory sequences and origins of replication. They will be preferably multicopy and have a selective marker gene, for example, a gene coding for antibiotic resistance. An example of such a vector is pTZ18R phagemid, obtainable from Pharmacia, Piscataway, N.J. 08854 which confers resistance to ampicillin in E. coli. The DNA sequences encoding the promoter, ribosome binding site and signal peptide may be from any single gene which encodes a secreted product.

The DNA sequences encoding the promoter and ribosome binding site may also be from a different gene than that encoding the signal peptide. The DNA sequences encoding the promoter, ribosome binding site and signal peptide can be isolated by means well known to those in the art and illustrative examples are documented in the literature. See Biotechnology Handbook 2 Bacillus, C. R. Harwood, Ed., Plenum Press, New York, N.Y. (1989). The promoters in the DNA sequences may be either constitutive or inducible and thus permit the resulting secretion vectors to be differentially regulated.

Promoters which are useful to drive expression of heterologous DNA fragments in E. coli and Bacillus are numerous and familiar to those skilled in the art. Virtually any promoter capable of driving the gene encoding a silk variant protein is suitable for the present invention, where the T7 promoters are preferred in E. coli and promoters derived from the SacB gene are preferred in Bacillus.

Termination control regions may also be derived from various genes native to E. coli or Bacillus hosts, or optionally other bacterial hosts. It will be appreciated by one of skill in the art that a termination control region may be unnecessary.

For introducing a polynucleotide of the present invention into a bacterial cell, known procedures can be used according to the present invention such as by transformation, e.g., using calcium-permeabilized cells, electroporation, or by transfection using a recombinant phage virus. (Sambrook et al., Molecular Cloning: A Laboratory Manual—volumes 1,2,3 (Cold Spring Harbor Laboratory: Cold Spring Harbor, N.Y., 1989)). Other known procedures can also be employed to obtain a recombinant host cell that expresses a heterologous spider silk protein according to the present invention, as will be apparent to those skilled in the art.

Design of Spider Silk Variant Amino Acid Sequences:

The design of the spider silk variant proteins was based on consensus amino acid sequences derived from the fiber forming regions of the natural spider silk dragline proteins of *Nephila clavipes*. Natural spider dragline consists of two different proteins that are co-spun from the spider's major ampullate gland. The amino acid sequence of both dragline proteins has been disclosed by Xu et al., Proc. Natl, Acad. Sci. U.S.A., 87, 7120, (1990) and Hinman and Lewis, J. Biol. Chem. 267, 19320 (1992), and will be identified hereinafter as Dragline Protein 1 (DP-1) and Dragline Protein 2 (DP-2).

The amino acid sequence of a fragment of DP-1 is repetitive and rich in glycine and alanine, but is otherwise unlike any previously known amino acid sequence. The repetitive nature of the protein and the pattern of variation among the individual repeats are emphasized by rewriting the sequence as in FIG. 1. The "consensus" sequence of a single repeat, viewed in this way, is:

A GQG GYG GLG XQG A GRG GLG GQG A GAAAAAAAGG (SEQ ID NO:1)

where X may be S,G, or N.

Examination of FIG. 1 shows that individual repeats differ from the consensus according to a pattern which can be generalized as follows: (1) The poly-alanine sequence varies in length from zero to seven residues. (2) When the entire poly-alanine sequence is deleted, so also is the surrounding sequence encompassing AGRGGLGGQGAGA$_n$GG (SEQ ID NO:2). (3) Aside from the poly-alanine sequence, deletions generally encompass integral multiples of three consecutive residues. (4) Deletion of GYG is generally accompanied by deletion of GRG in the same repeat. (5) A repeat in which the entire poly-alanine sequence is deleted is generally preceded by a repeat containing six alanine residues.

Synthetic analogs of DP-1 were designed to mimic both the repeating consensus sequence of the natural protein and the pattern of variation among individual repeats. Two analogs of DP-1 were designed and designated DP-1A and DP-1B. DP-1A is composed of a tandemly repeated 101-amino acid sequence listed in FIG. 2A. The 101-amino acid "monomer" SEQ ID NO:20 comprises four repeats which differ according to the pattern (1)–(5) above. This 101-amino acid long peptide monomer SEQ ID NO:20 is repeated from 1 to 16 times in a series of analog proteins. DP-1B was designed by reordering the four repeats within the monomer of DP-1A. This monomer sequence, shown in FIG. 3A, exhibits all of the regularities of (1)–(5) above. In addition, it exhibits a regularity of the natural sequence which is not shared by DP-1A, namely that a repeat in which both GYG and GRG are deleted is generally preceded by a repeat lacking the entire poly-alanine sequence, with one intervening repeat. The sequence of DP-1B matches the natural sequence more closely over a more extended segment than does DP-1A.

The amino acid sequence of a fragment of DP-2 is also repetitive and also rich in glycine and alanine, but is otherwise unlike any previously known amino acid sequence, and, aside from a region of consecutive alanine residues, different from DP-1. The repetitive nature of the protein and the pattern of variation among the individual repeats are emphasized by rewriting the sequence as in FIG. 8. The "consensus" sequence of a single repeat, viewed in this way, is:

[GPGGY GPGQQ]$_3$ GPSGPGS A$_{10}$ (SEQ ID NO:18)

Examination of FIG. 8 shows that individual repeats differ from the consensus according to a pattern which can be generalized as follows: (1) The poly-alanine-rich sequence varies in length from six to ten residues. (2) Aside from the poly-alanine sequence, individual repeats differ from the consensus repeat sequence by deletions of integral multiples of five consecutive residues consisting of one or both of the pentapeptide sequences GPGGY (SEQ ID NO:3) or GPGQQ (SEQ ID NO:4).

Synthetic analogs of DP-2 were designed to mimic both the repeating consensus sequence of the natural protein and the pattern of variation among individual repeats. The analog DP-2A SEQ ID NO:61 is composed of a tandemly repeated 119-amino acid sequence listed in FIG. 9A. The 119-amino acid "peptide monomer" comprises three repeats which differ according to the pattern (1)–(2) above. This 119-amino acid long peptide monomer is repeated from 1 to 16 times in a series of analog proteins.

Design of DNA encoding Spider Silk Variant Proteins:

DNA sequences encoding the designed analog amino acid sequences were devised according to the following criteria: (1) The DNA monomer was to be at least 300 bp in length; (2) within the monomer, repetitiveness of the sequence was minimized, with no repeated sequence longer than 17 bp and minimal repetitiveness of sequences longer than 10 bp; (3) where possible, codons were chosen from among the codons found preferentially in highly expressed genes of the intended host organism (*E. coli*) with preference for codons providing balanced A+T/G+C base ratios; and (4) predicted secondary structure of mRNA within the monomer was dominated by long-range interactions rather than shorter range base pairing. No attempt was made to minimize secondary structure of the mRNA.

Assembly of DP-1 and DP-2 Analog Genes:

Assembly of the synthetic dragline analog genes was accomplished by first assembling the appropriate DNA monomers followed by polymerization of these monomers to form the completed gene.

Synthetic DNA monomers, based on the consensus peptide monomers described above were assembled from four to six cloned double stranded synthetic oligonucleotides. Each oligonucleotide was designed to encode a different portion of the the peptide monomer. Briefly, the oligonucleotides were each cloned into separate suitable plasmid vectors containing an ampicillin resistance gene. A suitable *E. coli* host was transformed with the plasmids and screened for the presence of the correct vector by standard methods. After the oligonucleotides were cloned the DNA monomer was sequentially assembled. Vectors containing individual oligonucleotides were digested and the plasmid DNA was purified by gel electrophoresis. Purified plasmid DNA containing two different oligonucleotide sequences were then incubated under ligating conditions and the ligation products were used to transform a suitable *E. coli* host. These transformants comprised two of the oligonucleotide sequences linked in tandem. A similar procedure was followed for the creation of the full DNA monomer, comprising four to six of the oligonucleotides. Additional confirmation of the existence of the correct DNA insertions was obtained by direct DNA sequencing. The present invetion provides several DNA monomers useful for the production of DP-1A and DP-1B analogs. In general DNA monomers used to produce the the analog DP-1B.16 are preferred since this construct avoids codons rarely used by the *E. coli* production host.

The assembled DNA monomer was then polymerized by a method essentially as described by Kempe et al. (*Gene* 39, 239, (1985). This method consists of a series of successive doublings of the sequence of interest. Briefly, the DNA monomer containing the cloned oligonucleotides was digested with suitable restriction enzymes and incubated under annealing conditions followed by ligation to produce a series of constructs containing multiple repeats of the monomer. Ligation products were used to transform a suitable *E. coli* host and intact plasmids were selected on the basis of ampicillin resistance. Subsequent analysis of plasmid DNA by gel electrophoresis resulted in the identification of transformants containing plasmids with 2, 4, 8, and 16 tandem repeats of the DNA monomer. These protein products were analyzed by SDS polyacrylamide gel electrophoresis and detected and quantitated by immunochemical staining using a polyclonal antiserum raised in rabbits against a synthetic peptide analogous to a fragment of the natural protein.

Expression and Purification of Protein:

High level expression of the spider dragline protein analogs in *E. coli* was achieved by inserting the synthetic genes into plasmid vectors pFP202 and pFP204, which were derived from the well-known vector pET11a. In these vectors, the dragline protein-coding gene is inserted in such a manner as to be operably linked to a promoter derived from bacteriophage T7. This promoter is joined with sequences derived from the lac operator of *E. coli*, which confers regulation by lactose or analogs (IPTG). The *E. coli* host strain BL21(DE3) contains a lambda prophage which carries a gene encoding bacteriophage T7 RNA polymerase. This gene is controlled by a promoter which is also regulated by lactose or analogs. In addition to the phage T7 promoter, the vectors pFP202 and pFP204 provide sequences which encode a C-terminal tail containing six consecutive histidine resdues appended to the dragline protein-coding sequences. This tail provides a means of affinity purification of the protein under denaturing conditions through its adsorption to resins bearing immobilized Ni ions.

DP-1 analog protein was produced by *E. coli* at levels of approximately 5–20% of total protein. Of this, approximately 20–40% was recovered in purified form as full-length protein. DP-2 analog protein was produced at approximately 5% of total cell protein, of which approximately 30% was recovered in purified form as full-length protein.

The following examples are meant to illustrate the invention but should not be construed as limiting it in any way.

EXAMPLES

GENERAL METHODS

The position of the newly engineered restriction sites is indicated in the figures and any one skilled in the art can repeat these constructs with the available information.

The source of the genes and the various vectors described throughout this application are as follows.

The anti-DP-1 and anti-DP-2 antisera were prepared by Multiple Peptide Systems, San Diego, Calif.

Restriction enzyme digestions, phosphorylations, ligations, transformations and other suitable methods of genetic engineering employed herein are described in Sambrook et al., Molecular Cloning: A Laboratory Manual—volumes 1,2,3 (Cold Spring Harbor Laboratory: Cold Spring Harbor, N.Y., 1989), and in the instructions accompanying commercially available kits for genetic engineering.

Bacterial cultures and plasmids to carry out the present invention are available either commercially (from Novagen, Inc., Madison, Wis.) or from the *E. coli* Genetic Stock Center, Yale University, New Haven, Conn., the Bacillus Genetic Stock Center, Ohio State University, Columbus, Ohio, or the ATCC and, along with their sources, are identified in the text and examples which follow. Unless otherwise specified standard reagents and solutions used in the following examples were supplied by Sigma Chemical Co. (St. Louis, Mo.)

Isolation of restriction fragments from agarose gels used the GENECLEAN® procedure (Bio101, Inc., P.O. Box 2284, La Jolla, Calif.), and was performed as specified by the manufacturer.

Example 1

CONSTRUCTION OF THE SYNTHETIC GENES DP-1A.9 AND DP-1B.9 SEQ ID NO:81

Oligonucleotide Design and Cloning:

Synthetic genes encoding DP-1A.9 SEQ ID NO:80 and DP-1B.9 SEQ ID NO:81 were assembled from four double stranded synthetic oligonucleotides labled L (SEQ ID NOs.:24, 25, and 26), M1 (SEQ ID NOs.:27, 28, and 29), M2 (SEQ ID NOs.:30, 31, and 37), and S (SEQ ID NOs.:33, 34, and 35) whose sequences are shown in FIGS. 4A–4D. The oligonucleotides were provided by the manufacturer (Midland Certified Reagents, Midland, Tex.) in double stranded form with 5'-OH groups phosphorylated. Methods of oligonucleotide synthesis, purification, phosphorylation, and annealing to the double stranded form are well known to those skilled in the art.

The four double stranded oligonucleotides were separately cloned by inserting them into a plasmid vector pFP510 (FIG. 5). This vector was derived from the plasmid pA126i (see FIG. 13A), the complete nucleotide sequence of which is provided in SEQ ID NO.:78 and FIG. 13B. Details of the structure of pl126i are not important for the construction, aside from the following essential features: (a) a replication origin active in *E. coli*; (b) a selectable genetic marker, in this case a gene conferring resistance to the antibiotic ampicillin; (c) sites for restriction endonucleases BamHI and BglII with no essential sequences between them; and (d) a third restriction site (PstI), located within the selectable marker, which produces cohesive ends incompatible with those produced by BamHI and BglII. For the construction of pFP510, DNA of plasmid pA126i was digested with endonucleases BamHI and BglII, then recovered by adsorption to glass beads in the presence of NaI GENECLEAN® procedure (Bio101, Inc., P.O. Box 2284, La Jolla, Calif.). To approximately 0.1 pmole of the eluted plasmid DNA was added 10 pmoles of the double stranded, phosphorylated oligonucleotide SF4/5 (FIG. 5). The mixture was incubated under ligation conditions with T4 polynucleotide ligase for 19 h at 4° C. Ligated DNA was then digested with endonuclease XmaI to linearize any remaining parental pA126i and used to transform *E. coli* SK2267 (obtained from the *E. coli* Genetic Stock Center, Yale University, New Haven, Conn.) which had been made competent by calcium treatment as described by Sambrook et al., op. cit. Plasmid DNA isolated from ampicillin resistant transformants was characterized by digestion separately with endonucleases ApaI and BamHI, and a transformant containing the desired plasmid was identified and designated pFP510.

DNA of plasmid pFP510 was digested with endonucleases SfiI and DraIII and purified by the GENECLEAN® procedure (Bio101, Inc., P.O. Box 2284, La Jolla, Calif.). To approximately 0.1 pmole of the eluted plasmid DNA was added 10 pmoles of one of the double stranded, phosphorylated oligonucleotides L, M1, M2, or S (FIG. 4). The four plasmid-oligonucleotide mixtures were incubated under ligation conditions for 15 h at 4° C., then for 20 min at 23° C. and finally ligation was terminated by incubation for 3 min at 65° C. Aliquots of ligated DNA were used to transform *E. coli* SK2267 and ampicillin resistant transformants were selected. Clones containing oligonucleotides L, M1, and M2 shown in FIG. 4 were identified by screening plasmid DNA isolated from individual transformants with endonuclease AlwNI, a recognition site for which is present in the oligonucleotides. Clones containing oligonucleotide S were identified by screening plasmid DNA isolated from individual transformants with endonucleases BglI and DraIII. Plasmid DNA from putative clones was further characterized by digestion with endonucleases EcoRI, SfiI, and DraIII in order to establish that the oligonucleotide sequences were oriented correctly in the plasmid. The inserts were excised with endonucleases BamHI and BglII and analyzed by electrophoresis in 4% NuSieve agarose (FMC) to verify that the plasmid had acquired only a single copy of the oligonucleotide. Correct clones were identified and their plasmids were designated pFP521 (oligonucleotide L), pFP533 (oligonucleotide M1), pFP523 (oligonucleotide M2), and pFP524 (oligonucleotide S). DNA sequences of all four cloned oligonucleotides were verified by DNA sequencing.

DNA sequencing was carried out essentially according to procedures provided by the supplier (U.S. Biochemicals) with the Sequenase 2.0 kit for DNA sequencing with 7-deaza-GTP. Plasmid DNA was prepared using the Magic Minipreps kit (Promega). Template DNA was denatured by incubating 20 µl miniprep DNA in 40 µl (total volume) 0.2 M NaOH for 5 min at 23° C. The mixture was neutralized by adding 6 µl 2 M ammonium acetate (adjusted to pH 4.5 with acetic acid), and the DNA was precipitated by adding 0.15 mL ethanol, recovered by centrifugation, washed with cold 70% ethanol, and vacuum dried. Primers for sequencing were as follows:

SI1: 5'-ACGACCTCATCTAT (SEQ ID NO:5)
SI5: 5'-CTGCCTCTGTCATC (SEQ ID NO:6)
SI20: 5'-AATAGGCGTATCAC (SEQ ID NO:7)

Figure 12:
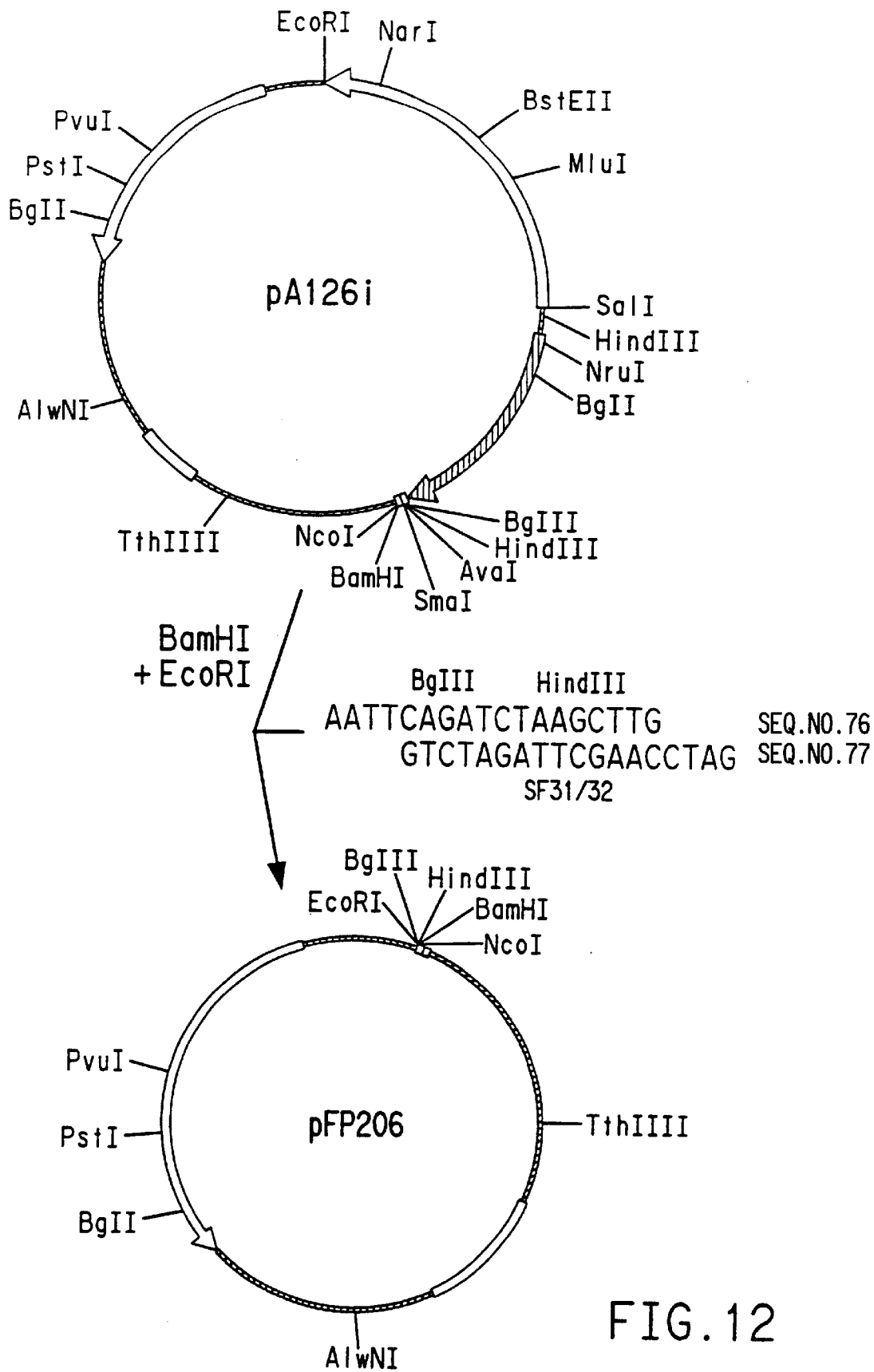
FIG. 12 is a plasmid map illustrating the construction of the plasmid pFP206 from pA126i. Plasmid pFP206 was used to construct plasmids used for the assembly and polymerization of the DNA monomer, and genes encoding DP-1B analogs.

Primers SI1 and SI5 anneal to sites on opposite strands in pA126i. SI5 primes synthesis into the sequences of interest from 31 bp beyond the BamHI site. SI1 primes synthesis on the opposite strand into the sequences of interest from 38 bp beyond the BglII site. For sequencing in the vector pFP206 (see below) the primer SI20, which anneals 25 bp beyond the BglII site, was substituted for SI1 (FIG. 12). Polyacrylamide gels for DNA sequencing were run at 52° C.

Assembly of the Gene:

For assembly of subsequence M2L, plasmid pFP523 (M2) was digested with endonucleases PstI and DraIII, and plasmid pFP521 (L) was digested with endonucleases PstI and SfiI. Digested plasmid DNA was fractionated by electrophoresis in a 1.2% agarose (low melting, BioRad) gel. Ethidium bromide-stained bands containing the oligonucleotide sequences, identified by their relative sizes, were excised, the excised bands combined, and the DNA recovered from melted agarose by the GENECLEAN® procedure (Bio101, Inc., P.O. Box 2284, La Jolla, Calif.). The eluted combined DNA fragments were incubated under ligation conditions and an aliquot was used to transform *E. coli* W3110 (available from the *E. coli* Genetic Stock Center, Yale University, New Haven, Conn.). Ampicillin resistant transformants were selected. Plasmid DNA was isolated from several transformants, digested with endonucleases BamHI and BglII, and analyzed by agarose gel electrophoresis. Plasmid containing insert of the expected size was identified and designated pFP525.

Assembly of subsequence M1S was accomplished in the same manner, starting with plasmids pFP533 (digested with PstI-and DraIII) and pFP524 (digested with PstI and SfiI). Plasmid containing the MIS subsequence was identified and designated pFP531.

For assembly of the DNA monomer (M2LM1S), plasmid pFP525 (M2L) was digested with endonucleases PstI and DraIII, and plasmid pFP531 (M1S) was digested with endonucleases PstI and SfiI. Digested plasmid DNA was fractionated by electrophoresis in a 1.2% low melting agarose gel. Ethidium bromide-stained bands containing the M2L and M1S sequences, respectively, identified by their relative sizes, were excised, the excised bands combined, and the DNA recovered from melted agarose by the GENECLEAN® procedure (Bio101, Inc., P.O. Box 2284, La Jolla, Calif.). The eluted combined DNA fragments were incubated under ligation conditions and an aliquot was used to transform E. coli W3110. Ampicillin resistant transformants were selected. Plasmid DNA was isolated from several transformants, digested with endonucleases BamHI and BglII, and analyzed by agarose gel electrophoresis. Plasmid containing insert of the expected size was identified and designated pFP534. The DNA inserts in plasmids pFP523, pFP521, pFP533, pFP524, pFP525, pFP531, and pFP534 were verified by direct DNA sequencing as previously described.

Polymerization of the Gene:

The synthetic gene was extended by sequential doubling, starting with the monomer sequence in pFP534. For doubling any insert sequence, an aliquot of plasmid DNA was digested with endonucleases PstI and DraIII, and a separate aliquot of the same plasmid was digested with endonucleases PstI and SfiI. Digests were fractionated by electrophoresis on low melting agarose, and ethidium bromide stained fragments containing insert sequences were identified by their relative sizes. In some cases, the two fragments were not adequately separated, so it was necessary to cut the non-insert-containing fragment with a third enzyme, usually MluI.

Each of the two insert sequence-containing fragments has one end generated by endonuclease PstI. Annealing of these compatible single stranded ends and ligation results in reconstitution of the gene that confers ampicillin resistance, part of which is carried on each fragment. The other end of each fragment displays a single stranded sequence generated by either DraIII or SfiI. These sequences are, by design, complementary, and annealing and ligation results in a head-to-tail coupling of two insert sequences, with concomitant loss of both sites at the junction. The principle of this method of insert sequence doubling was described by Kempe et al. (*Gene* 39, 239–245 (1985)).

The two insert-containing fragments, purified by electrophoresis and recovered by the GENECLEAN® procedure (Bio101, Inc., P.O. Box 2284, La Jolla, Calif.), were combined and incubated under ligation conditions. An aliquot was used to transform E. coli W3110. Ampicillin resistant transformants were selected. Plasmid DNA was isolated from several transformants, digested with endonucleases BamHI and BglII, and analyzed by agarose gel electrophoresis. Plasmid containing insert of the expected size was identified.

By this procedure a series of plasmids was constructed containing 2, 4, 8, and 16 tandem repeats of the DNA monomer sequence M2LM1S, encoding the series of DP-1A analogs. In addition, analogous methods were used to construct genes encoding the series of DP-1B analogs. For this purpose, subsequences SL (from pFP524 and pFP521) and M1M2 (from pFP533 and pFP523) were first constructed, then combined to form the monomer SLM1M2, which was polymerized as described. It should be apparent that similar methods can be used to assemble any combination of subsequences carried in the vector pFP510, or any other appropriate vector, provided that the subsequences are bounded by cleavage sites for restriction endonucleases that generate compatible ends (complementary single stranded ends or blunt ends). In addition to various monomer sequences, polymers of any number of repeats of the monomer sequence can be assembled in the same way, starting with plasmids containing inserts of different sizes.

Example 2

SYNTHETIC GENE DP-1B.16

A second set of genes encoding DP-1B, designated DP-1B.16 (SEQ ID NO.:82), were designed to reduce the number of codons which are rarely used in highly expressed E. coli genes, but at the same time encoding proteins of the same repeating sequence. The sequence of the DP-1B.16 peptide monomer is shown in FIG. 10A and in SEQ ID NO.:82.

Oligonucleotide Synthesis and Cloning:

Synthetic genes encoding DP-1B.16 (SEQ ID NO.:82) were assembled from four double stranded synthetic oligonucleotides whose sequences (SEQ ID NOs.:64, 65, 66; SEQ ID NOs.:67, 68, 69; SEQ ID NOs.:70, 71, 72; and SEQ ID NOs.:73, 74, 75) are shown in FIGS 11A–11D. The oligonucleotides were provided by the manufacturer (Midland Certified Reagents, Midland, Tex.) in single stranded form with 5'-OH groups not phosphorylated. For annealing to the double stranded form, complementary single stranded oligonucleotides (667 pmoles each) were mixed in 0.2 mL buffer containing 0.01 M Tris-HCl, 0.01 M MgCl2, 0.05 M NaCl, 0.001 M dithiothreitol, pH 7.9. The mixture was heated in boiling water for 1 minute, then allowed to cool slowly to 23° C. over approximately 3 h.

The four double stranded oligonucleotides were separately cloned by inserting them into a plasmid vector pFP206 (FIG. 12). This vector was derived from the plasmid pA126i as illustrated in FIG. 12. Briefly, DNA of plasmid pA126i was digested with endonucleases BamHI and EcoRI, and the two fragments were separated by electrophoresis in a 1.2% agarose (low melting, BioRad). The larger of the two fragments was excised from the ethidium bromide-stained gel and recovered by the GENECLEAN® procedure (Bio101, Inc., P.O. Box 2284, La Jolla, Calif.). To approximately 0.1 pmole of the eluted DNA fragment was added 10 pmoles of the double stranded, phosphorylated oligonucleotide SF31/32 (FIG. 12). The mixture was incubated under ligation conditions with T4 polynucleotide ligase for 8.5 h at 4° C. Ligated DNA was used to transform E. coli HB101, which had been made competent by calcium treatment. Plasmid DNA isolated from ampicillin resistant transformants was characterized by digestion separately with endonucleases HindIII, EcoRI, BglII, and BamHI, and a transformant containing the desired plasmid was identified and designated pFP206.

DNA of plasmid pFP206 was digested with endonucleases BamHI and BglII and purified by the GENECLEAN® procedure (Bio101, Inc., P.O. Box 2284, La Jolla, Calif.). To approximately 0.1 pmole of the eluted plasmid DNA was added 10 pmoles of one of the double stranded oligonucleotides 1 (SEQ ID NOs.:64, 65, 66) 2

(SEQ ID NOs.:67, 68, 69), 3 (SEQ ID NOs.:70, 71, 72), or 4 (SEQ ID NOs.:73, 74, 75). The four plasmid-oligonucleotide mixtures were incubated under ligation conditions for 15 h at 4° C., then ligation was terminated by incubation for 3 min at 70° C. Ligated DNA was then digested with endonuclease HindIII to linearize any remaining parental pFP206. Aliquots of ligated DNA were used to transform E. coli HB101 and ampicillin resistant transformants were selected. Clones containing oligonucleotides 1, 2, 3, or 4 were identified by screening plasmid DNA isolated from individual transformants with endonucleases BamHI and PstI. In plasmids with inserts in the desired orientation, the shorter of two BamHI-PstI fragments of pFP206 is lengthened by the length of the cloned oligonucleotide. Plasmid DNA from putative clones was further characterized by digestion with endonucleases BamHI and BglII and analysis by electrophoresis in 3% NuSieve agarose (FMC), 1% Agarose (Sigma Chemical Co.) to verify that the plasmid had acquired only a single copy of the oligonucleotide in the correct orientation. Correct clones were identified and their plasmids were designated pFP636 (oligonucleotide 1), pFP620 (oligonucleotide 2), pFP641 (oligonucleotide 3), and pFP631 (oligonucleotide 4). Sequences of all four cloned oligonucleotides were verified by DNA sequencing as described above.

Assembly of the Gene:

For assembly of subsequence 1,2, plasmid pFP636 (1) was digested with endonucleases PstI and BamHI, and plasmid pFP620 (2) was digested with endonucleases PstI and BglII. Digested plasmid DNA was fractionated by electrophoresis in a 1.2% agarose (low melting, BioRad) gel. Ethidium bromide-stained bands containing the oligonucleotide sequences, identified by their relative sizes, were excised, the excised bands combined, and the DNA recovered from melted agarose by the GENECLEAN® procedure (Bio101, Inc., P.O. Box 2284, La Jolla, Calif.). The eluted combined DNA fragments were incubated under ligation conditions and an aliquot was used to transform E. coli HB101. Ampicillin resistant transformants were selected. Plasmid DNA was isolated from several transformants, digested with endonucleases BamHI and BglII, and analyzed by agarose gel electrophoresis. Plasmid containing insert of the expected size was identified and designated pFP647.

Assembly of subsequence 3,4 was accomplished in the same manner, starting with plasmids pFP641 (digested with PstI and BamHI) and pFP631 (digested with PstI and BglII). Plasmid containing the 3,4 subsequence was identified and designated pFP649.

For assembly of the DNA monomer (1,2,3,4), plasmid pFP647 (1,2) was digested with endonucleases PstI and BamHI, and plasmid pFP640 (3,4) was digested with endonucleases PstI and BglII. Digested plasmid DNA was fractionated by electrophoresis in a 1.2% low melting agarose gel. Ethidium bromide-stained bands containing the 1,2 and 3,4 sequences, respectively, identified by their relative sizes, were excised, the excised bands combined, and the DNA recovered from melted agarose by the GENECLEAN® procedure (Bio101, Inc., P.O. Box 2284, La Jolla, Calif.). The eluted combined DNA fragments were incubated under ligation conditions and an aliquot was used to transform E. coli HB101. Ampicillin resistant transformants were selected. Plasmid DNA was isolated from several transformants, digested with endonucleases BamHI and BglII, and analyzed by agarose gel electrophoresis. Plasmid containing insert of the expected size was identified and designated pFP652. The DNA insert in plasmid pFP652 was verified by direct DNA sequencing as described above.

Polymerization of the Gene:

The synthetic gene was extended by sequential doubling, starting with the monomer sequence in pFP652. For doubling any insert sequence, an aliquot of plasmid DNA was digested with endonucleases PstI and BamHI, and a separate aliquot of the same plasmid was digested with endonucleases PstI and BglII. Digests were fractionated by electrophoresis on low melting agarose, and ethidium bromide stained fragments containing insert sequences were identified by their relative sizes. The two insert-containing fragments, purified by electrophoresis and recovered by the GENECLEAN® procedure (Bio101, Inc., P.O. Box 2284, La Jolla, Calif.), were combined and incubated under ligation conditions. At the third doubling, the two fragments in the BamHI digest were not adequately separated, so the eluted band contained both fragments. In this case a two-fold excess of the BglII-PstI fragment was used in the ligation. An aliquot of the ligated DNA was used to transform E. coli HB101. Ampicillin resistant transformants were selected. Plasmid DNA was isolated from several transformants, digested with endonucleases BamHI and BglII, and analyzed by agarose gel electrophoresis. Plasmid containing insert of the expected size was identified.

By this procedure a series of plasmids was constructed containing 2, 4, 8, and 16 tandem repeats of the DNA monomer sequence 1 (SEQ ID NOs.:64, 65, 66), 2 (SEQ ID NOs.:67, 68, 69), 3 (SEQ ID NOs.:70, 71, 72), 4 (SEQ ID NOs.:73, 74, 75), encoding the series of DP-1B.16 analogs. These plasmids were designated pFP656 (2 repeats), pFP661 (4 repeats), pFP662 (8 repeats), and pFP665 (16 repeats), respectively.

Example 3

SYNTHETIC GENE DP-2A

Oligonucleotide Synthesis and Cloning:

Synthetic genes encoding DP-2A SEQ ID NO:61 were assembled from six double stranded synthetic oligonucleotides whose sequences are shown in FIGS. 7A–7F. The oligonucleotides were provided by the manufacturer (Midland Certified Reagents, Midland, Tex.) in double stranded form with 5'-OH groups not phosphorylated. The six double stranded oligonucleotides were separately cloned by inserting them into the plasmid vector pFP206.

DNA of plasmid pFP206 was digested with endonucleases BamHI and BglII and purified by the GENECLEAN® procedure (Bio101, Inc., P.O. Box 2284, La Jolla, Calif.). To approximately 0.1 pmole of the eluted plasmid DNA was added 10 pmoles of one of the double stranded oligonucleotides A (SEQ ID NOs.:41, 42, 43), B (SEQ ID NOs.:44, 45, 46), C (SEQ ID NOs.:47, 48, 49), D (SEQ ID NOs.:50, 51, 52), E (SEQ ID NOs.:53, 54, 55), or F (SEQ ID NOs.:56, 57, 58). The six plasmid-oligonucleotide mixtures were incubated under ligation conditions for 15 h at 4° C., then ligation was terminated by incubation for 3 min at 70° C. Ligated DNA was then digested with endonuclease HindIII to linearize any remaining parental pFP206. Aliquots of ligated DNA were used to transform E. coli HB101 and ampicillin resistant transformants were selected. Clones containing oligonucleotides A, B, C, D, E, or F were identified by screening plasmid DNA isolated from individual transformants with endonucleases BamHI and PstI. In plasmids with inserts in the desired orientation, the shorter of two BamHI-PstI fragments of pFP206 is lengthened by the length of the cloned oligonucleotide. Plasmid DNA from putative clones was further characterized by digestion with endonucleases BamHI and BglII and analysis by electrophoresis in 3% NUSIEVE agarose (FMC), 1% Agarose (Sigma Chemical Co.) to verify that the plasmid had acquired only a single copy of the oligonucleotide in the correct orientation. Correct clones were identified and their plasmids were designated pFP193 (oligonucleotide A), pFP194 (oligonucleotide B), pFP195 (oligonucleotide C), pFP196 (oligonucleotide D), pFP197 (oligonucleotide E), and pFP198 (oligonucleotide F).

Assembly of the Gene:

For assembly of subsequence AB, plasmid pFP193 (A) was digested with endonucleases PstI and PvuII, and plasmid pFP194 (B) was digested with endonucleases PstI and SmaI. Digested plasmid DNA was fractionated by electrophoresis in a 1.2% agarose (low melting, BioRad) gel. Ethidium bromide-stained bands containing the oligonucleotide sequences, identified by their relative sizes, were excised, the excised bands combined, and the DNA recovered from melted agarose by the GENECLEAN® procedure (Bio101, Inc., P.O. Box 2284, La Jolla, Calif.). The eluted combined DNA fragments were incubated under ligation conditions and an aliquot was used to transform $E.$ $coli$ HB101. Ampicillin resistant transformants were selected. Plasmid DNA was isolated from several transformants, digested with endonucleases BamHI and BglII, and analyzed by agarose gel electrophoresis. Plasmid containing insert of the expected size was identified and designated pFP300 (AB).

Assembly of subsequence CD was accomplished in the same manner, starting with plasmids pFPl95 (digested with PstI and SnaBI) and pFP196 (digested with PstI and SmaI). Plasmid containing the CD subsequence was identified and designated pFP578. Assembly of subsequence EF was accomplished in the same manner, starting with plasmids pFP197 (digested with PstI and SnaBI) and pFP198 (digested with PstI and SmaI). Plasmid containing the EF subsequence was identified and designated pFP583. The DNA inserts in plasmids pFP300, pFP578, and pFP583 were verified by direct DNA sequencing as described above.

Assembly of subsequence CDEF was accomplished similarly, starting with plasmids pFP578 (digested with PstI and PvuII) and pFP583 (digested with PstI and SmaI). Plasmid containing the CDEF subsequence was identified and designated pFP588.

For assembly of the DNA monomer (ABCDEF), plasmid pFP300 (AB) was digested with endonucleases PstI and PvuII, and plasmid pFP588 (CDEF) was digested with endonucleases PstI and SmaI. Digested plasmid DNA was fractionated by electrophoresis in a 1.2% low melting agarose gel. Ethidium bromide-stained bands containing the AB and CDEF sequences, respectively, identified by their relative sizes, were excised, the excised bands combined, and the DNA recovered from melted agarose by the GENECLEAN® procedure (Bio101, Inc., P.O. Box 2284, La Jolla, Calif.). The eluted combined DNA fragments were incubated under ligation conditions and an aliquot was used to transform $E.$ $coli$ HB101. Ampicillin resistant transformants were selected. Plasmid DNA was isolated from several transformants, digested with endonucleases BamHI and BglII, and analyzed by agarose gel electrophoresis. Plasmid containing insert of the expected size was identified and designated pFP303. The DNA insert in plasmid pFP303 was verified by direct DNA sequencing.

Polymerization of the Gene:

The synthetic gene was extended by sequential doubling, starting with the monomer sequence in pFP303. For doubling any insert sequence, an aliquot of plasmid DNA was digested with endonucleases PstI and PvuII, and a separate aliquot of the same plasmid was digested with endonucleases PstI and SmaI. Digests were fractionated by electrophoresis on low melting agarose, and ethidium bromide stained fragments containing insert sequences were identified by their relative sizes. The two insert-containing fragments, purified by electrophoresis and recovered by the GENECLEAN® procedure (Bio101, Inc., P.O. Box 2284, La Jolla, Calif.), were combined and incubated under ligation conditions. An aliquot of the ligated DNA was used to transform $E.$ $coli$ HB101. Ampicillin resistant transformants were selected. Plasmid DNA was isolated from several transformants, digested with endonucleases BamHI and BglII, and analyzed by agarose gel electrophoresis. Plasmid containing insert of the expected size was identified.

By this procedure a series of plasmids was constructed containing 2, 4, 8, and 16 tandem repeats of the DNA monomer sequence ABCDEF, encoding the series of DP-2A analogs. These plasmids were designated pFP304 (2 repeats), pFP596 (4 repeats), pFP597 (8 repeats), and pFP598 (16 repeats), respectively.

Example 4

EXPRESSION OF DP-1 AND DP-2 ANALOG GENES IN $E.$ $COLI$

Immunoassay

For detection of DP-1 analog amino acid sequences, polyclonal antisera were raised in rabbits by immunization with a synthetic peptide matching the most highly conserved segment of the consensus repeat sequence of the natural protein. The peptide (sequence CGAGQGGYGGLGSQGAGRG-NH$_2$) (SEQ ID NO:8) was synthesized by standard solid phase methods (Multiple Peptide Systems, San Diego, Calif.) and coupled through its terminal Cys thiol to Keyhole Lympet Hemocyanin via maleimidobenzoyl-N-hydroxysuccinimide ester. Similarly, for detection of DP-2 analog amino acid sequences, antisera were raised against a peptide of sequence CGPGQQGPGGYGPGQQGPS-NH$_2$ (SEQ ID NO:9), which reflects the consensus repeat sequence of the natural protein DP-2.

For the growth of cultures to assess production levels, 20 mL L broth (per liter: 10 g Bacto-Tryptone (Difco), 5 g Bacto-Yeast Extract (Difco), 5 g NaCl, pH adjusted to 7.0 with NaOH) containing 0.1 mg/mL ampicillin in a 125 mL baffled Erlenmeyer flask was inoculated at an absorption (A600 nm) of approximately 0.05 with cells eluted from an L-agar plate containing 0.1 mg/mL ampicillin, which had been grown overnight at 37° C. The culture was shaken at 37° C. until the $A_{600}$ nm reached approximately 1.0, at which time IPTG was added to a final concentration of 1 mM. Samples (0.5 mL) were taken immediately before IPTG addition and after an additional 3 h at 37° C. Cells were immediately recovered by centrifugation in a microfuge, supernatant was removed, and the cell pellet was frozen in dry ice and stored at −70° C.

For analysis by polyacrylamide gel electrophoresis, cell pellets were thawed, suspended in 0.2 mL sample preparation buffer (0.0625 M Tris-HCl, pH 6.8, 2% w/v Na-dodecyl sulfate, 0.0025% w/v bromphenol blue, 10% v/v glycerol, 2.5% v/v 2-mercaptoethanol), and incubated in a boiling water bath for 5 min. Aliquots (15 $\mu$l) were applied to a 4–12% gradient polyacrylamide gel (Novex) and subjected to electrophoresis until the dye front was less than 1-cm from the bottom of the gel. The gel was stained with Coomassie Brilliant Blue. A second gel (6% acrylamide) was run with similar samples, then protein bands were transferred electrophoretically to a sheet of nitrocellulose, using an apparatus manufactured by Idea Scientific, Inc. The buffer for transfer contained (per liter) 3.03-g Trishydroxymethyl aminomethane, 14.4-g glycine, 0.1% w/v SDS, 25% v/v methanol.

The nitrocellulose blot was stained immuno-chemically as follows. Protein binding sites on the sheet were blocked by incubation with "Blotto" (3% nonfat dry milk, 0.05% TWEEN 20, in Tris-saline (0.1 M Tris-HCl, pH 8.0, 0.9% w/v NaCl)) for 30 min at room temperature on a rocking platform. The blot was then incubated for 1 h with anti DP-1 serum or anti DP-2 serum, diluted 1:1000 in "Blotto", washed with Tris-saline, and incubated for 1 h with horseradish peroxidase-conjugated goat anti-rabbit IgG serum (Kierkegaard and Perry Laboratories, Gaithersburg, Md.), diluted 1:1000 in "Blotto". After again washing with Tris-saline, the blot was exposed to a solution of 18 mg 4-chloro-1-naphthol in 6 mL methanol, to which had been added 24 mL Tris-saline and 30 µl 30% $H_2O_2$.

For quantitation of DP-1 antigen production, cell extracts were prepared by either of two procedures.

Procedure 1: The cell pellet from 0.5 mL culture was resuspended in 0.084 mL 50 mM EDTA, pH 8.0, to which was then added 10 µl 10 mg/mL egg white lysozyme in the same buffer, 1 µl 2 mg/mL bovine pancreatic ribonuclease, and 5 µl 0.1 M phenyl methane sulfonyl fluoride in ethanol. After 15 min at 37° C., 1 µl 1 mg/mL DNase I was added, along with 3 µl 1 M $MgCl_2$, 1 M $MgSO_4$, and incubation was continued for 10 min at 37° C. The resulting lysate was clarified by centrifugation for 5 min in a microfuge, and the supernatant was diluted to 0.5 mL with Tris-saline.

Procedure 2: The cell pellet was resuspended in 0.5 mL of buffer 8.0G containing 6 M guanidine-HCl, 0.1 M $NaH2PO_4$, 0.01 M Tris-HCl, 5 mM 2-mercaptoethanol, pH adjusted to 8.0 with NaOH. After thorough mixing and incubation for 1 h at 23° C., cell debris was removed by centrifugation for 15 minutes in a microfuge.

Aliquots (1 µl) of serial dilutions in Tris saline (Procedure 1) or buffer 8.0G (Procedure 2) were spotted onto nitrocellulose, along with various concentrations of a standard solution of purified DP-1 8-mer (8 repeats of 101 amino acid residues). The nitrocellulose sheet was then treated as described above for the Western blot. The concentration of DP-1 antigen in each sample was estimated by matching the color intensity of one of the standard spots.

Figure 6:
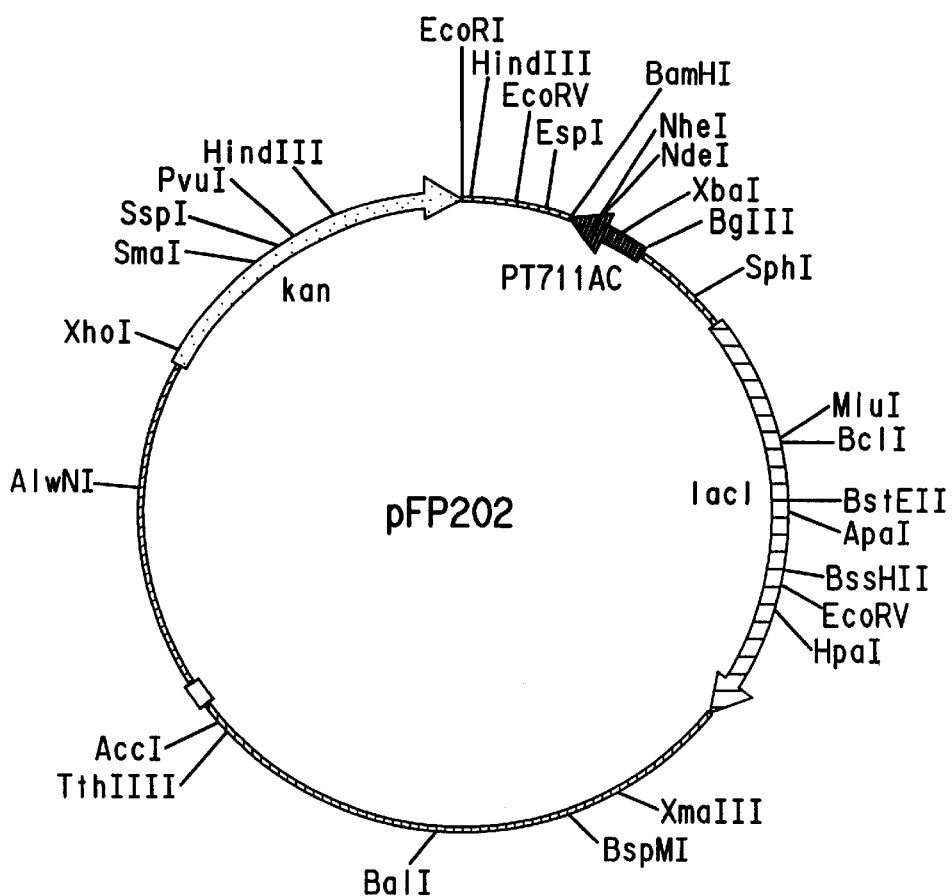
FIG. 6 is a plasmid map of plasmid pFP202 which is used to construct high level expression vectors.

Production Strains:

Vectors:

To construct bacterial strains for production of DP-1, cloned synthetic DP-1-coding DNA sequences were inserted into plasmid vector, pFP202 (FIG. 6) or pFP204, which were derived from plasmid pFP200, which was, in turn, derived from the plasmids pET11a and pET9a of Studier et al., *Methods in Enzymology*, 185, 60 (1990). Plasmids pET9a and pET11a and host strains BL21, BL21(DE3), HMS174, and HMS174(DE3) were obtained from Novagen, Madison, Wis.

To construct the plasmid pFP200, DNA of plasmids pET9a and pET11a were digested with endonucleases EcoRI and AlwNI and the digests fractionated separately by electrophoresis in low-melting agarose. The appropriate ethidium bromide-stained bands (from pET9a, the band carrying the gene that confers resistance to kanamycin, and from pET11a, the band carrying the T7 promoter) were identified by size, excised and recovered from melted gel slices by the GENECLEAN® procedure (Bio101, Inc., P.O. Box 2284, La Jolla, Calif.). Equivalent amounts of the purified DNA bands were combined and incubated under ligation conditions. An aliquot of the ligated DNA was used to transform *E. coli* BL21 and transformants were selected for resistance to kanamycin (50 µg/mL). Plasmid DNA from individual transformants was analyzed following digestion with endonuclease ClaI, and a correct one was identified and designated pFP200.

Next DNA sequences encoding six consecutive histidine residues were inserted into pFP200. Such sequences were carried on a synthetic double stranded oligonucleotide (SF25/26) with the following sequence:

```
        G   S   H   H   H   H   H   S   R
                                              (SEQ ID NO:10)
5'HO-GATCCCATCACCATCACCATCACTCTA
                                              (SEQ ID NO:11)
         GGTAGTGGTAGTGGTAGTGAGATCTAG-OH 5'
                                              (SEQ ID NO:12)
```

The amino acid sequence encoded by this oligonucleotide when it is inserted in the correct orientation into the BamHI site of pFP200 is shown in one-letter code above the DNA sequence. DNA of pFP200 was digested with endonuclease BamHI and recovered by the GENECLEAN® procedure (Bio101, Inc., P.O. Box 2284, La Jolla, Calif.). An aliquot of this digested DNA (approximately 0.02 pmoles) was mixed with oligonucleotide SF25/26 (10 pmoles), the 5' termini of which had not been phosphorylated. After incubation under ligation conditions for 5 h at 4° C. and 20 min at 23° C., an aliquot was used to transform *E. coli* BL21. Transformants were selected for kanamycin resistance and plasmid DNA of individual transformants was analyzed following digestion with endonucleases EcoRI and BamHI. A correct plasmid was identified by the presence in the digest of a DNA band indicative of restoration of the BamHI site at the promoter-proximal end of the oligonucleotide sequence, resulting from insertion in the desired orientation. This plasmid was designated pFP202. Correct insertion of the oligonucleotide was verified by direct DNA sequencing as described above.

The plasmid vector pFP204 was constructed in an analogous manner, by inserting into pFP200 a synthetic double stranded oligonucleotide (SF29/30) with the following sequence:

```
                                              (SEQ ID NO:13)
         G   S   H   H   H   H   H
                                              (SEQ ID NO: 14)
5'HO-GATCCCATCACCATCACCATCACTAAA
                                              (SEQ ID NO:15)
         GGTAGTGGTAGTGGTAGTGATTTCTAG-OH 5'
```

This oligonucleotide places a termination codon immediately following the six tandem His residues.

DP-1A.9 Strains:

Next sequences encoding DP-1A were inserted into pFP202 at the BamHI site located between the T7 promoter and sequences encoding the His6 oligomer. DNA of plasmids pFP534 (encoding 101 aa DP-1A), pFP538 (encoding 2 repeats of 101 aa DP-1A), and pFP541 (8 repeats of 101 aa DP-1A) were digested with endonucleases BamHI and BglII, and pFP546 (16 repeats of 101 aa DP-1) was digested with BamHI, BglII, and EcoRI. The digests were fractionated by electrophoresis in low-melting agarose, and the ethidium bromide-stained band carrying the DP-1-encoding sequences was identified by size and excised. The excised gel bands were melted, and to each was added an aliquot of pFP202 DNA that had been digested with endonuclease BamHI. DNA was recovered by the GENECLEAN® procedure (Bio101, Inc., P.O. Box 2284, La Jolla, Calif.) and incubated under ligation conditions for 2 h at 4° C., followed by 20 min at 23° C. An aliquot of ligated DNA was used to transform *E. coli* BL21(DE3), and transformants were selected for resistance to kanamycin.

Individual transformants were patched onto a sheet of cellulose acetate on the surface of LB agar containing kanamycin. After overnight growth, the cellulose acetate was transferred to a second plate on which a sheet of nitrocellulose had been placed on the surface of LB agar containing 1mM IPTG. After incubation for 3 h at 37° C., the nitrocellulose sheet was removed from under the cellulose acetate, blocked with "Blotto", and developed by immunochemical staining with anti-DP-1 serum as described below. Positive transformants, identified by blue color in this colony immunoassay, were picked from a replica master plate that had been inoculated at the same time as the immunoassay plate, with the same transformant colonies. The correct structure of plasmid DNA from positive transformants was verified following digestion with endonucleases BamHI and BglII. Transformants in which the DP-1-encoding insert was inserted backwards (as identified by the formation of appropriately sized bands in the digest) gave a positive reaction on colony immunoassay, but the color yield was markedly less intense than those in the correct orientation. Transformants containing plasmids with correctly oriented inserts were identified and designated FP3211 (1 repeat of 101 aa), FP3217 (2 repeats), FP3203 (8 repeats) and FP3206 (16 repeats).

DP-1 protein produced by strains FP3217, FP3203, and FP3206 was assayed by Western blot analysis as described below. All were shown to produce full-length protein of the expected size, detected by anti-DP-1 serum. In addition, a regular array of anti-DP-1-staining protein bands was observed, mainly at higher gel mobilities.

DP-1B.9 Strains:

*E. coli* strains for the production of DP-1B.9 were constructed in a similar fashion by transferring DNA fragments encoding DP-1B.9 (SEQ ID NO.:81) (derived by digestion with BamHI and BglII of plasmids pFP156 and pFP158, containing 8 and 16 repeats of the 303 bp DNA monomer, respectively) into plasmid pFP202. The resulting production strains were designated FP2121 (8repeats) and FP2123 (16 repeats). Both strains were shown by Western Blot analysis to produce full-length protein of the expected size.

DP-1B.16 Strains:

*E. coli* strains for the production of DP-1B.16 (SEQ ID NO.:82) were constructed in a similar fashion by transferring DNA fragments encoding DP-1B.16 (derived by digestion with BamHI and BglII of plasmids pFP662 and pFP665 containing 8 and 16 repeats of the 303 bp DNA monomer, respectively) into plasmid pFP204. The resulting production strains were designated FP3350 (8 repeats) and FP3356 (16 repeats). Both strains were shown by Western Blot analysis to produce full-length protein of the expected size. Host cell FP3350 has been deposited with the ATCC under the terms of the Budapest Treaty and is identified by the ATCC number ATCC 69328 (deposited Jun. 15, 1993).

DP-2A Strains:

*E. coli* strains for the production of DP-2A SEQ ID NO:61 were constructed in a similar fashion by transferring DNA fragments encoding DP-2A (derived by digestion with BamHI and BglII of plasmids pFP597 and pFP598, containing 8 and 16 repeats of the 357 bp DNA monomer, respectively) into plasmid pFP204. The resulting production strains were designated FP3276 (8 repeats) and FP3284 (16 repeats). Both strains were shown by Western Blot analysis to produce full-length protein of the expected size.

Example 5

LARGE SCALE PRODUCTION, PURIFICATION AND QUANTITATION OF RECOMBINANT SILK VARIANT PROTEINS

Purification of DP-1A.9 (SEO ID NO.:80):

Strain FP3203 was grown at 36° C. in a Fermgen fermenter (New Brunswick Scientific, New Brunswick, N.J.) in 10 l of a medium containing:

| | |
|---|---|
| $(NH_4)_2SO_4$ | 3.0 g |
| $MgSO_4$ | 4.5 g |
| Na citrate · $2H_2O$ | 0.47 g |
| $FeSO_4 \cdot 7H_2O$ | 0.25 g |
| $CaCl_2 \cdot 2H_2O$ | 0.26 g |
| Thiamine-HCl | 0.6 g |
| Casamino acids | 200 g |
| Biotin | 0.05 g |
| $K_2HPO_4$ | 19.5 g |
| $NaH_2PO_4$ | 9.0 g |
| Glycerol | 100 g |
| L-Alanine | 10.0 g |
| Glycine | 10.0 g |
| Glucose | 200 g |
| PPG | 5 mL |
| $ZnSO_4 \cdot 7H_2O$ | 0.08 g |
| $CuSO_4 \cdot 5H_2O$ | 0.03 g |
| $MnSO_4 \cdot H_2O$ | 0.025 g |
| $H_3BO_3$ | 0.0015 g |
| $(NH_4)_nMO_x$ | 0.001 g |
| $COCl_2 \cdot 6H_2O$ | 0.0006 g |

The fermenter was inoculated with 500 mL overnight culture of FP3203 in the same medium. The pH was maintained at 6.8 by addition of 5 N NaOH or 20% $H_3PO_4$. Dissolved $O_2$ was maintained at approximately 50%. When the absorption at 600 nm had reached 10–15, production of DP-1 was induced by adding 5-g IPTG. After 3 h, cells were harvested by centrifugation and frozen. The yield was 314 g cell paste. Thawed cells (100 g paste) were suspended in 1000 mL buffer 8.OG containing 6 M guanidine-HCl, 0.1 M $NaH_2PO_4$, 0.01 M Tris-HCl, 5 mM 2-mercaptoethanol, pH adjusted to 8.0 with NaOH. After stirring for 1 h at 23° C., the lysate was clarified by centrifugation at 10,000×g for 30 min, and the supernatant was filtered through Whatman No. 3 paper. To the filtrate was added 200 mL packed volume of Ni-nitrilotriacetic acid (NTA)-agarose (Qiagen, Inc.), which had been equilibrated with buffer 8.0 G, recovered by filtration, and drained. The lysate-resin slurry was stirred at 23° C. for 24 h, then the resin was recovered by filtration on Whatman No. 3 paper. The drained resin. was suspended in 500 mL buffer 8.0 G and packed into a chromatography column (5 cm diameter). The column was washed with 500 mL buffer 8.0 G, then with successive 320 mL volumes of buffers of the same composition as buffer 8.0 G, but with the pH adjusted with NaOH to the following values: pH 6.3, 6.1, 5.9, 5.7, and 5.5. Effluent fractions of 40 mL were collected. DP-1 protein was located by immunoassay, as described above. Positive fractions were pooled and the pH was adjusted to 8.0 with NaOH. Immunoassay and Western blot analysis revealed that approximately 50% of the material containing DP-1 sequences was adsorbed to the resin and recovered in the pooled fractions. The remaining material apparently lacks the C-terminal oligo-histidine affinity tail, presumably as a result of premature termination of protein synthesis.

The concentration of 2-mercaptoethanol was adjusted to 17 mM, and the pooled material was stirred for 5 h at 23° C. This material was reapplied to the same Ni-NTA-agarose column, which had been re-equilibrated with buffer 8.0 G. The column was then washed with 200 mL buffer 8.0 G and 400 mL of buffer with a similar composition, but with a pH of 6.5, followed by 400 mL of a buffer composed of 0.1 M acetic acid adjusted to pH 6.5 with triethylamine, plus 5 mM 2-mercaptoethanol. DP-1 protein was eluted with 800 mL of a buffer composed of 0.1 M acetic acid adjusted to pH 5.0 with triethylamine, while 40 mL eluant fractions were collected. DP-1 protein was located by immunoassay. Positive fractions were pooled and the buffer was removed by lyophilization. Yield of lyophilized material was 100 mg, representing approximately 1% of the total protein present in the 100 g cell paste from which it was derived.

Amino acid analysis of the purified DP-1 is shown in Table I and is consistent with the predicted amino acid sequence, with impurities (as proteins of amino acid composition reflecting the overall composition of *E. coli* (Schaechter, M. et al., in *Escherichia coli* and *Salmonella typhimurium*, Neidhardt, F. C. (ed) Washington D.C., American Association for Microbiology, p.5, (1987)) less than 7%.

TABLE I

Amino Acid Analysis DP1-A, 8-mer, Recovered from FP3203

| Amino Acid | Residues per Molecule | | n Moles |
|---|---|---|---|
| | Theoretical | Experimental | Experimental (Raw) |
| Gly | 383 | 367 | 10.91 |
| Ala | 235 | [235] | 6.98 |
| Glx | 92 | 98 | 2.91 |
| Leu | 40 | 40 | 1.32 |
| Ser | 37 | 37 | 1.09 |
| Tyr | 24 | 25 | 0.75 |
| Arg | 18 | 22 | 0.66 |
| Met | 3 | 3 | 0.09 |
| His | 6 | 8.7 | 0.26 |
| Asx | 0 | 6 | 0.18 |
| Thr | 1 | 4 | 0.13 |
| Val | 0 | 4 | 0.13 |
| Ile | 0 | 3 | 0.10 |
| Phe | 0 | 0 | |
| Lys | 0 | 3 | 0.10 |
| Pro | 0 | 0 | 0.00 |
| Purity: 93% | | | |

Purification of DP-1B.16 (SEQ ID NO.:82):

Strain FP3350 was grown in 5 liters under conditions noted above. Thawed cell paste (154 g) was suspended in 1000 mL buffer 8.0 G and stirred for 2 h at 23° C. The lysate was clarified by centrifugation for 30 min at 10,000×g. To the supernatant was added 300 mL (packed volume) of Ni-NTA agarose equilibrated with buffer 8.0 gG. The mixture was stirred at 23° C. for 18 h, then the resin was recovered by centrifugation at 1,000×g for 30 min. The resin was diluted to 800 mL with buffer 8.0 G, mixed, and allowed to settle. Supernatant was removed and the settling procedure was repeated. The settled resin was then diluted with an equal volume of buffer 8.0 G and packed into a chromatography column (5 cm diameter). The column was washed successively with (a) 1300 mL buffer 8.0 G, (b) 500 mL buffer 8.0 G containing 8 mM imidazole, (c) 100 mL buffer 8.0 G, and (d) 500 mL buffer 6.5 G (same composition as buffer 8.0 G, but with the pH adjusted to 6.5 with NaOH). DP-1B.16 protein was finally eluted with buffer 5.5 G (same composition as buffer 8.0 G, but with the pH adjusted to 5.5 with NaOH). Fractions containing DP-1B.16 were identified by spot immunoassay, pooled, and concentrated approximately 40-fold by ultrafiltration using Centriprep 30 centrifugal concentrators (Amicon). Protein was precipitated by the addition of 5 volumes of methanol, incubating 16 h at 4° C., recovered by centrifugation, washed twice with methanol and vacuum dried.

The yield of dried material was 287 mg, representing approximately 2% of the total protein present in the 154 g cell paste from which it was derived. Amino acid analysis is shown in Table II and is consistent with the predicted amino acid sequence, with impurities (as proteins of amino acid composition reflecting the overall composition of *E. coli*) representing approximately 21% of the total protein in the sample.

TABLE II

Amino Acid Analysis DP-1B16 8-mer Recovered from FP3350

| Amino Acid | Residues per Molecule | | n Moles |
|---|---|---|---|
| | Theoretical | Experimental | Experimental (Raw) |
| Gly | 383 | 338 | 26.27 |
| Ala | 235 | [235] | 18.25 |
| Glx | 92 | 105 | 8.13 |
| Leu | 40 | 54 | 4.22 |
| Ser | 37 | 32 | 2.44 |
| Tyr | 24 | 25 | 1.95 |
| Arg | 18 | 30 | 2.32 |
| Met | 3 | 4.2 | 0.32 |
| His | 6 | 24.2 | 1.88 |
| Asx | 0 | 19.2 | 1.49 |
| Thr | 1 | 9.4 | 0.73 |
| Val | 0 | 13.5 | 1.05 |
| Ile | 0 | 10.7 | 0.83 |
| Phe | 0 | 7.3 | 0.57 |
| Lys | 0 | 10.1 | 0.78 |
| Pro | 0 | 8.6 | 0.67 |
| Purity: 79% | | | |

Purification of DP-2A (SEQ ID NO.:83):

Strain FP3276 was grown in 5 liters under conditions noted above, except that the growth medium was supplements at inoculation with 0.375 g/l L-proline, and at induction with 0.1 g/l glycine and L-alanine and 0.0375 g/l L-proline. Thawed cell paste from two such fermentations (150 g and 140 g, respectively) was suspended in 1000 mL each buffer 8.0 G and stirred for 1 h at 23° C. The lysate was clarified by centrifugation for 30 min at 10,000×g. The supernatants were combined and mixed with 300 mL (packed volume) of Ni-NTA agarose equilibrated with buffer 8.0 G. The mixture was stirred at 23° C. for 18 h, then the resin was recovered by centrifugation at 1,000×g for 30 min. The resin was diluted to 800 mL with buffer 8.0 G, mixed, and allowed to settle. Supernatant was removed and the settling procedure was repeated twice. The settled resin was then diluted with an equal volume of buffer 8.0 G and packed into a chromatography column (5 cm diameter). The column was washed successively with (a) 1350 mL buffer 8.0 G, (b) 400 mL buffer 8.0 G containing 8 mM imidazole, (c) 100 mL buffer 8.0 G, and (d) 750 mL buffer 6.5 G. DP-2A SEQ ID NO:61 protein was finally eluted with buffer 5.5 G. Fractions containing DP-1B.16 were identified by spot immunoassay and pooled.

Of a total of 240 mL pooled fractions, 150 was removed and concentrated approximately 40-fold by ultrafiltration using Centriprep 30 centrifugal concentrators (Amicon). Protein was precipitated by the addition of 5 volumes of methanol, incubating 16 h at 4° C., recovered by centrifugation, washed twice with methanol and vacuum dried. The yield of dried material was 390 mg.

The remaining 90 mL pooled column fractions was concentrated 8-fold using Centriprep 30 concentrators, diluted to the original volume with water and concentrated again. This procedure was repeated three additional times in order to remove guanidine to less than 5 mM. The material was finally lyophilized. The weight of lyophilized material was 160 mg. Thus the total yield of purified DP-2A SEQ ID NO:61 was 550 mg, representing approximately 2% of the total protein present in the 290 g cell paste from which it was derived.

Amino acid analysis of a sample of the lyophilized material is shown in Table III and is consistent with the predicted amino acid sequence, with impurities (as proteins of amino acid composition reflecting the overall composition of E. coli) representing less than 4% of the total protein in the sample.

TABLE III

Amino Acid Analysis
DP-2A, 8-mer Recovered from Strain FP3276

| Amino Acid | Residues per Molecule | | n Moles |
|---|---|---|---|
| | Theoretical | Experimental | Experimental (Raw) |
| Gly | 373 | 351 | 16.98 |
| Ala | 185 | [185] | 8.95 |
| Pro | 169 | 158 | 7.64 |
| Glx | 130 | 93 | 4.51 |
| Ser | 51 | 48 | 2.35 |
| Tyr | 56 | 57 | 2.76 |
| Met | 3 | 2.0 | 0.10 |
| His | 6 | 9.2 | 0.45 |
| Leu | 1 | 1.8 | 0.09 |
| Asx | 0 | ND | ND |
| Thr | 1 | ND | ND |
| Val | 0 | 5.5 | 0.27 |
| Ile | 0 | 0 | 0.00 |
| Phe | 0 | 2.8 | 0.13 |
| Lys | 0 | 1.9 | 0.09 |
| Arg | 1 | 0 | 0.00 |

Purity: 96%

The present invention discloses the construction of several specific expression systems useful for the production of spider silk variant proteins. In order to leave no doubt that one of skill in the art might be able to use the elements of the instant invention to produce the myriad of other spider silk variant proteins not specifically discussed, E. coli bacteria transformed with an expression vector (pFP204) devoid of synthetic spider silk variant DNA has been deposited with the ATCC under the terms of the Budapest treaty and is identified by the ATCC number ATCC 69326. The expression pFP204 contained in the host cell E. coli HB101 comprises all the necessary restriction sites needed to clone synthetic spider silk DNA of the instant invention and may be used to express any spider silk variant protein. In addition, the expression host strain E. coli BL21 (DE3) transformed with a plasmid pFP674 carrying DP-1B.16 coding sequences (SEQ ID NO.:82), has been deposited with the ATCC under the terms of the Budapest treaty and is identified by the ATCC number ATCC 69328. This strain can be used to produce DP-1B according to this invention, or cured of plasmid by methods well known to those skilled in the art and transformed with other expression vectors derived from pFP204.

Example 6

SYNTHESIS AND EXPRESSION OF DP-1 ANALOG IN BACILLUS SUBTILIS

For expression in Bacillus subtilis, a DP-1 analog-encoding gene from plasmid pFP141 was placed in a plasmid vector capable of replication in B. subtilis. DP-1 coding sequences were operably linked to a promoter derived from the levansucrase (lvs) gene of Bacillus amyloliquefaciens in such a manner that the N-terminal amino acid sequence coded by the levansucrase gene, which comprises a secretion signal sequence, was fused to the DP-1 sequence at its N-terminus. Gene fusions of this type have been shown, in some cases, to promote the production and secretion into the extracellular medium of foreign proteins (Nagarajan et al. U.S. Pat. No. 4,801,537).

As illustrated in FIG. 15, to prepare the DP-1 analog gene for transfer into the appropriate vector for B. subtilis, the endonuclease BglII site at the proximal end of the DP-1 coding sequence in plasmid pFP541 was first converted to an EcoRV site by inserting a synthetic oligonucleotide. DNA of plasmid pFP541 was digested with endonuclease BglII. Approximately 0.1 pmole of the linearized plasmid DNA was then incubated under ligation conditions with 10 pmoles of a synthetic double stranded oligonucleotide (SI9/10) with the following sequence:

5'HO-GATCAGATATCG    (SEQ ID NO:16)

TCTATAGCCTAG-OH 5'    (SEQ ID NO:17)

Ampicillin resistant transformants of E. coli HMS174 were screened for plasmid DNA containing an EcoRV site provided by the synthetic oligonucleotide sequence. A plasmid containing an EcoRV site was identified and designated pFP169b (FIG. 15A). Next the DNA fragment carrying DP-1 coding sequences was isolated from pFP169b following digestion with endonucleases EcoRV and BamHI and separation of the resulting DNA fragments by agarose gel electrophoresis. A band of the appropriate size was excised from the ethidium bromide stained gel and DNA was recovered by the GENECLEAN® procedure (Bio101, Inc., P.O. Box 2284, La Jolla, Calif.).

The plasmid vector pBE346 contains replication origins that confer autonomous replication in both E. coli and B. subtilis, as well as antibiotic resistance markers selectable in E. coli (ampicillin) and B. subtilis (kanamycin). In addition, the plasmid contains the lvs promoter and secretion signal operably linked to a staphylococcal protein A gene. The protein A gene is bounded by an EcoRV site at its proximal end, separating it from the lvs signal sequence, and a BamHI site at its distal end. The complete DNA sequence of pBE346 (FIG. 14A) is shown in SEQ ID NO.:79 and in FIGS. 14A–14F. In order to remove the protein A gene and allow for its replacement by the DP-1 gene, DNA of plasmid pBE346 was digested with endonucleases EcoRV and BamHI and the appropriate sized fragment was isolated following agarose gel electrophoresis. DNA was recovered from the ethidium bromide stained gel band by the GENECLEAN® procedure (Bio101, Inc., P.O. Box 2284, La Jolla, Calif.).

Figure 15B:
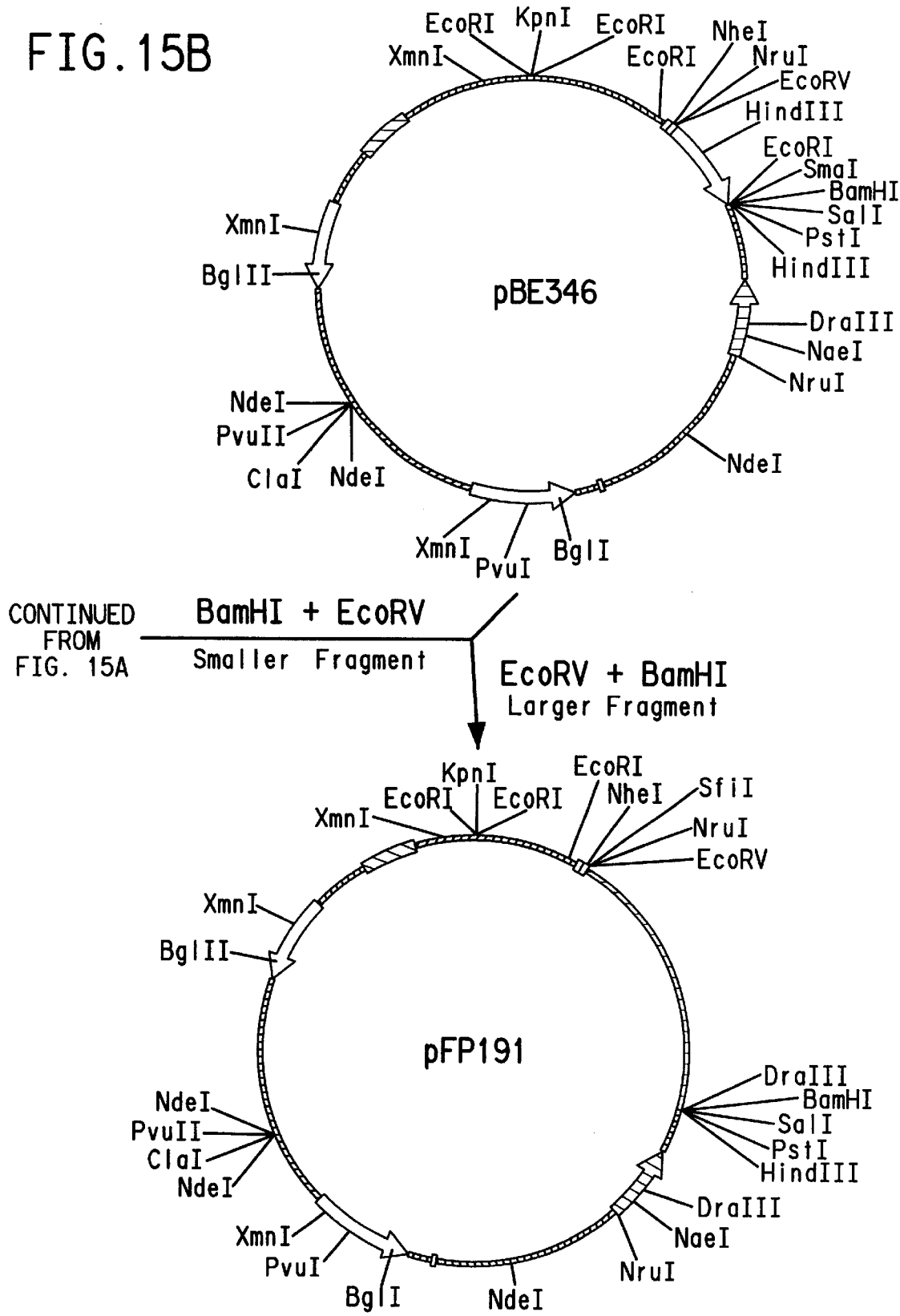
FIG. 15B illustrates the construction of plasmid pFP191 from pBE346.

DNA fragment purified from pFP169b (above) was mixed with the DNA fragment purified from pBE346 and incubated under ligation conditions. Ligated DNA was used to transform E. coli HMS174, and ampicillin resistant transformants were screened by examining plasmid DNA for the presence of appropriately sized fragments following digestion with endonucleases EcoRV and BamHI. A correct plasmid was identified and designated pFP191 (FIG. 15B).

DNA of plasmid pFP191 was used to transform competent cells of B. subtilis BE3010 (trp lys apr npr sacB). Transformants were selected for resistance to kanamycin. BE3010 was derived from B. subtilis BE1500, (trpC2, metB10, lys3, delta-aprE, delta-npr, sacB::ermC) which has been described by Nagarajan et al., Gene, 114, 121, (1992) by transforming competent BE1500 cells with DNA from B. subtilis 1S53 (Bacillus Genetic Stock Center, Ohio State University) and selecting for methionine prototrophs. Transformation of competent cells was carried out essentially as described by Nagarajan et al., U.S. Pat. No. 4,801,537.

Kanamycin resistant transformants of BE3010 were screened for the ability to produce DP-1 by colony immunoassay. Colonies were grown on a cellulose acetate disk placed on the surface of a plate containing TBAB agar plus 5 micrograms per mL kanamycin. After colonies had developed at 37° C., the cellulose acetate disk was transferred to a fresh plate containing the same medium plus 0.8% sucrose, and placed over a nitrocellulose disk which was placed on the surface of the agar. After incubation for 3 h at 37° C., the nitrocellulose disk was removed and stained with anti-DP-1 serum, peroxidase-conjugated goat anti-rabbit IgG, and 4-chloro-1-naphthol plus hydrogen peroxide as described above. Positively staining images of the colonies were observed, indicating the production and excretion of DP-1, compared to a negative control strain containing a plasmid with no DP-1 coding sequences. The positive strain was designated FP2193. FP2193 has been deposited with the ATCC under the terms of the Budapest Treaty and is identified by the ATCC number, ATCC 69327.

The production and excretion of DP-1 by FP2193 was assayed in liquid culture. Strain FP2193 was grown in Medium B, containing, per liter, 33 g Bacto-tryptone (Difco), 20 g yeast extract, 7.4 g NaCl, 12 mL 3N NaOH, 0.8 g $Na_2HPO_4$, 0.4 g $KH_2PO_4$, 0.2% casamino acids (Difco), 0.5% glycerol, 0.06 mM $MnCl_2$, 0.5 nM $FeCl_3$, pH 7.5. After growth for 3.5 h at 37° C., production of DP-1 was induced by the addition of sucrose to 0.8%. After 4 h additional incubation at 37° C., a sample of 0.5 mL was analyzed. Cells were removed by centrifugation. The upper 0.4 mL of supernatant was removed and phenylmethane sulfonyl fluoride (PMSF) was added to 2 mM. The residual supernatant was removed and discarded. The cell pellet was suspended in 0.32 mL 50 mM EDTA, pH8.0, and lysed by the addition of 0.08 mL 10 mg/mL egg white lysozyme in the same buffer, plus 2 mM PMSF. After incubation for 60 min at 37° C., 0.01 mL 2M $MgCl_2$ and 0.001 mL 1 mg/mL deoxyribonuclease I were added, and incubation continued for 5 min at 37° C. Aliquots (5 microliters) of each fraction, cell lysate and supernatant, were analyzed by SDS gel electrophoresis and electroblotting as described above. The blot was stained with anti-DP-1 serum. Several positively staining bands were observed in the supernatant fraction, and only a trace of positive band in the cell lysate. The host strain BE3010 containing no DP-1 coding DNA sequences produced no positively staining bands. Thus B. subtilis strain FP2193 was shown to produce DP-1 analog protein and to excrete it efficiently into the extracellular medium.

Example 7

DP-1B Production in Pichia pastoris

1. Synthetic Gene DP-1B.33

A set of genes encoding DP-LB, designated DP-1B.33, were designed to encode proteins of the same repeating sequence as DP-1B.9 and DP-1B.16, but to use predominantly codons favored in the highly expressed alcohol oxidase genes of Pichia pastoris.

a. Oligonucleotides

Synthetic genes encoding DP-1B.33 were assembled from four double stranded synthetic oligonucleotides whose sequences are shown in FIG. 16. The oligonucleotides were provided by the manufacturer (Midland Certified Reagents, Midland, Tex.) in single-stranded form with 5'-OH groups not phosphorylated. For annealing to the double-stranded form, complementary single stranded oligonucleotides (667 pmoles each) were mixed in 0.2 ml buffer containing 0.01 M Tris-HCl, 0.01 M $MgCl_2$, 0.05 M NaCl, 0.001 M dithiothreitol, pH 7.9. The mixture was heated in boiling water for 1 min, then allowed to cool slowly to 23° C. over approximately 3 h.

The four double-stranded oligonucleotides were separately cloned by inserting them into a plasmid vector pFP206. DNA of plasmid pFP206 was digested with endonucleases BamHI and BglII and purified by the GENECLEAN® procedure (Bio101, Inc., P.O. Box 2284, La Jolla, Calif.). To approximately 0.1 pmole of the eluted plasmid DNA was added 10 pmoles of one of the double-stranded oligonucleotides P1, P2, P3, or P4. The four plasmid-oligonucleotide mixtures were incubated under ligation conditions for 20 h at 4° C., then ligation was terminated by incubation for 2 min at 70° C. Ligated DNA was then digested with endonuclease HindIII to linearize any remaining parental pFP206. Aliquots of ligated DNA were used to transform E. coli HB101 and ampicillin resistant transformants were selected. Clones containing oligonucleotides P1, P2, P3, or P4 were identified by screening plasmid DNA isolated from individual transformants with endonucleases BamHI and PstI. In plasmids with inserts in the desired orientation, the shorter of two BamHI-PstI fragments of pFP206 is lengthened by the length of the cloned oligonucleotide. Plasmid DNA from putative clones was further characterized by digestion with endonucleases BamHI and BglII and analysis by electrophoresis in 3.8% MetaPhor agarose (FMC) to verify that the plasmid had acquired a single copy of the oligonucleotide in the correct orientation. Correct clones were identified and their plasmids were designated pFP685 (oligonucleotide P1, SEQ ID NOs.:84, 85, and 86), pFP690 (oligonucleotide P2, SEQ ID NOs.:87, 88, and 89), pFP701 (oligonucleotide P3, SEQ ID NOs.:90, 91, and 92), and pFP693 (oligonucleotide P4, SEQ ID NOs.:93, 94, and 95). Sequences of all four cloned oligonucleotides were verified by DNA sequencing.

b. Assembly of the Gene

For assembly of subsequence P1,P2, plasmid pFP685 (P1, SEQ ID NOs.:84, 85, and 86) was digested with endonucleases PstI and BamHI, and plasmid pFP690 (P2, SEQ ID NOs.:87, 88, and 89) was digested with endonucleases PstI and BglII. Digested plasmid DNA was fractionated by electrophoresis in a 1.2% agarose (low melting, BioRad, Hercules, Calif.) gel. Ethidium bromide-stained bands containing the oligonucleotide sequences, identified by their relative sizes, were excised, the excised bands combined, and the DNA recovered from melted agarose by the GENECLEAN® procedure (Bio101, Inc., P.O. Box 2284, La Jolla, Calif.). The eluted combined DNA fragments were incubated under ligation conditions and an aliquot was used to transform E. coli HB101. Ampicillin resistant transformants were selected. Plasmid DNA was isolated from several transformants, digested with endonucleases BamHI and BglII, and analyzed by agarose gel electrophoresis. Plasmid containing insert of the expected size was identified and designated pFP707.

Assembly of subsequence P3,P4 was accomplished in the same manner as the subsequence P1,P2, starting, however, with plasmids pFP701 (digested with PstI and BamHI) and pFP693 (digested with PstI and BglII). Plasmid containing the P3,P4 subsequence was identified and designated pFP709.

For assembly of the DNA monomer (P1,P2,P3,P4), plasmid pFP707 (P1, P2) was digested with endonucleases PstI and BamHI, and plasmid pFP709 (P3,P4) was digested with endonucleases PstI and BglII. Digested plasmid DNA was fractionated by electrophoresis in a 1.2% low melting agarose gel. Ethidium bromide-stained bands containing the P1,P2 and P3,P4 sequences, respectively, identified by their relative sizes, were excised, the excised bands combined, and the DNA recovered from melted agarose by the GENECLEAN® procedure (Bio101, Inc., P.O. Box 2284, La Jolla, CA). The eluted combined DNA fragments were incubated under ligation conditions and an aliquot was used to transform *E. coli* HB101. Ampicillin-resistant transformants were selected. Plasmid DNA was isolated from several transformants, digested with endonucleases BamHI and BglII, and analyzed by agarose gel electrophoresis. Plasmid containing an insert of the expected size was identified and designated pFP711. The DNA insert in plasmid pFP711 was verified by direct DNA sequencing.

c. Polymerization of the Gene

The synthetic gene was extended by sequential doubling, starting with the monomer sequence in pFP711. For doubling any insert sequence, an aliquot of plasmid DNA was digested with endonucleases PstI and BamHI, and a separate aliquot of the same plasmid was digested with endonucleases PstI and BglII. Digests were fractionated by electrophoresis on low melting agarose (BioRad, Calif.), and ethidium bromide stained fragments containing insert sequences were identified by their relative sizes. The two insert-containing fragments, purified by electrophoresis and recovered by the GENECLEAN® procedure (Bio101, Inc., P.O. Box 2284, La Jolla, CA), were combined and incubated under ligation conditions. At the third doubling, the two fragments in the BamHI digest were not adequately separated, so the eluted band contained both fragments. In this case a two-fold excess of the BglII-PstI fragment was used in the ligation. An aliquot of the ligated DNA was used to transform *E. coli* HB101. Ampicillin resistant transformants were selected. Plasmid DNA was isolated from several transformants, digested with endonucleases BamHI and BglII, and analyzed by agarose gel electrophoresis. Plasmid containing an insert of the expected size was identified.

By this procedure a series of plasmids was constructed containing 2, 4, 8, and 16 tandem repeats of the DNA monomer sequence P1,P2,P3,P4, encoding the series of DP-1B.16 analogs. These plasmids were designated pFP713 (2 repeats), pFP715 (4 repeats), pFP717 (8 repeats), and pFP719 (16 repeats), and p723 (16 repeats), respectively.

2. Expression of DP-1 and DP-2 Analog Genes in *Pichia pastoris* a. Growth and Assays

For the growth of cultures to assess production levels, 20 ml BMGY (per liter: 13.4 g yeast nitrogen base with ammonium sulfate (Difco), 10 g yeast extract, 20 g peptone, 0.4 mg biotin, 100 ml 1 M potassium phosphate buffer, pH 6.0, 10 ml glycerol) in a 125 ml baffled Erlenmeyer flask was inoculated at an absorption ($A_{600}$ nm) of approximately 0.1 with cells eluted from a YPD agar plate (containing per liter: 10 g yeast extract (Difco), 20 g peptone, 20 g Bacto agar (Difco), 20 g D-glucose), which had been grown 2 days at 30° C. The culture was shaken at 30° C. until the $A_{600}$ nm reached approximately 25 (2 days), at which time cells were harvested by centrifugation (5 min at 1500×g). Supernatant was discarded and the cells resuspended in 6 ml BMMY (same as BMGY, except with 5 ml methanol per liter in place of glycerol). The culture was shaken at 30° C., and 0.005 ml methanol per ml culture was added every 24 h. Samples (1 ml) were taken immediately after resuspension and at intervals. Cells were immediately recovered by centrifugation in a microfuge (2 min at 6000×g). Where secretion was to be assayed, the top 0.7 ml supernatant was removed and frozen in dry ice ("culture supernatant" fraction). The drained cell pellet was frozen in dry ice and stored at −70° C.

Cells were lysed by shaking with glass beads. The thawed pellet was washed with 1 ml cold breaking buffer (50 mM sodium phosphate, pH 7.4, 1 mM EDTA, 5% (v/v) glycerol, 1 mM phenyl methane sulfonyl flouride), and resuspended in 0.1 ml of the same buffer. Glass beads (acid washed, 425–600 microns; Sigma Chemical Co.) were added until only a meniscus was visible above the beads, and the tubes subjected to mixing on a vortex type mixer for two intervals of 4 min, cooling on ice between. Cell breakage was verified by microscopic examination. After complete breakage, 0.5 ml breaking buffer was added and mixed. Debris and beads were pelleted in the microfuge (10 min), and 0.5 ml supernatant (soluble cell extract) removed. The debris was then extracted twice with additional 0.5 ml portions of breaking buffer, and the 0.5 ml supernatants combined with the first extract ("soluble cell extract" fraction). The debris was then extracted three times with 0.5 ml portions of buffer 6.5 G, containing 0.1 M sodium phosphate, 0.01 M Tris-HCl, 6M guanidine-HCl, pH 6.5. The combined supernatants comprised the "insoluble cell extract" fraction.

For analysis by polyacrylamide gel electrophoresis, extracts were diluted approximately 1000-fold into sample preparation buffer (0.0625 M Tris-HCl, pH 6.8, 2% w/v Na-dodecyl sulfate, 0.0025% w/v bromphenol blue, 10% v/v glycerol, 2.5% v/v 2-mercaptoethanol), and incubated in a boiling water bath for 5 min. Aliquots (5–15 $\mu$l) were applied to an 8% polyacrylamide gel (Novex) and subjected to electrophoresis until the dye front was less than 1 cm from the bottom of the gel. Protein bands were transferred electrophoretically to a sheet of nitrocellulose, using an apparatus manufactured by Idea Scientific, Inc. The buffer for transfer contained (per liter) 3.03 g Trishydroxymethyl aminomethane, 14.4 g glycine, 0.1% w/v SDS, 25% v/v methanol.

The nitrocellulose blot was stained immuno-chemically as follows. Protein binding sites on the sheet were blocked by incubation with "Blotto" (3% nonfat dry milk, 0.05% Tween 20, in Tris-saline (0.1 M Tris-HCl, pH 8.0, 0.9% w/v NaCl)) for 30 min at room temperature on a rocking platform. The blot was then incubated for 1 h with anti DP-1 serum, diluted 1:1000 in "Blotto", washed with Tris saline, and incubated for 1 h with horseradish peroxidase-conjugated goat anti-rabbit IgG serum (Kierkegaard and Perry Laboratories, Gaithersburg, Md.), diluted 1:1000 in "Blotto". After again washing with Tris-saline, the blot was exposed to a solution of 18 mg 4-chloro-1-naphthol in 6 ml methanol, to which had been added 24 ml Tris-saline and 30 $\mu$l 30% $H_2O_2$.

For quantitation of DP-1 antigen levels in various fractions, aliquots (1 $\mu$l) of serial dilutions in buffer 6.5 G were spotted onto nitrocellulose, along with various concentrations of a standard solution of purified DP-1 8-mer (8 repeats of 101 amino acid residues). The nitrocellulose sheet was then treated as described above for the Western blot. The concentration of DP-1 antigen in each sample was estimated by matching the color intensity of one of the standard spots.

b. Production Strains (1) Vectors

To construct yeast strains for production of DP-1, cloned synthetic DP-1-coding DNA sequences were inserted into plasmid vectors which were derived from the plasmids pHIL-D4 (obtained from Phillips Petroleum Co.), or pPIC9 (obtained from Invitrogen Corp.). The structure of pHIL-D4 is illustrated in FIG. 17. The plasmid includes a replication origin active in *E. coli* (but not in yeast) and ampicillin and kanamycin resistance markers that are selectable in *E. coli*.

The kanamycin resistance marker also confers resistance to the antibiotic G418 in yeast. The plasmid includes regions homologous to both ends of the *Pichia pastoris* AOX1 gene. The upstream region includes the AOX1 promoter, expression from which is inducible by methanol. Sequences to be expressed are inserted adjacent to the AOX1 promoter. Downstream are sequences encoding the AOX1 polyadenylation site and transcription terminator, the kanamycin marker, and the *Pichia pastoris* HIS4 gene. In pHIL-D4 no translated sequences are provided upstream from the sequences to be expressed. The vector pPIC9 (FIG. 18) is similar to pHIL-D4, except it includes, adjacent to the AOX1 promoter, sequences encoding the signal sequence and pro- sequence of the *Saccharomyces cerevisiae* alpha-mating factor gene. Also, pPIC9 lacks the kanamycin resistance gene of pHIL-D4.

A BamHI site in pPIC9, located immediately upstream of the 5' end of the alpha-mating factor gene was removed, and the sequences restored to those resembling the natural AOX1 gene, by polymerase chain reaction (PCR) (Perkin Elmer Cetus, Calif.). Fragments of pPIC9 were amplified separately using the following primer pairs:

LB1:5'-CAACTAATTATTCGAAACGATGAGATTTCC-3' (SEQ ID NO.:98)

LB6:5'-CTGAGGAACAGTCATGTCTAAGG-3' (SEQ ID NO.:99)

and

LB2:5'-GGAAATCTCATCGTTTCGAATAATTAGTTG-3' (SEQ ID NO.:100)

LB5:5'-GAAACGCAAATGGGGAAACAACC-3' (SEQ ID NO.:101)

PCR reactions were carried out in a Perkin Elmer Cetus DNA Thermal Cycler, using the Perkin Elmer Cetus Gene-Amp kit with AmpliTaq® DNA polymerase. Instructions provided by the manufacturer were followed. The template DNA was approximately 0.2 ng pPIC9 DNA digested with endonucleases BglII and PvuII and subsequently recovered by the GENECLEAN® procedure (Bio101, Inc., P.O. Box 2284, La Jolla, Calif.). The PCR program included (a) 1 min at 94° C.; (b) 4 cycles consisting of 1 min at 94° C., 2 min at 45° C., 1 min at 72° C.; (c) 25 cycles consisting of 1 min at 94° C., 1 min at 60° C., 1 min at 72° C. (extended by 10 sec each cycle); and (d) 7 min at 72° C. Products were recovered from the two separate PCR reactions by the GENECLEAN® procedure (P.O. Box 2284, La Jolla, Calif.) and mixed in approximately equimolar amounts. This mixture was used as template for a second round of PCR using primers LB5 and LB6. For this reaction, the PCR program included (a) 1 min at 94° C.; (b) 25 cycles consisting of 1 min at 90° C., 1 min at 60° C., 1 min at 72° C. (extended 10 sec per cycle); and (d) 7 min at 72° C. The PCR product was recovered by the GENECLEAN® procedure (Bio101, Inc., P.O. Box 2284, La Jolla, Calif.), then digested with endonucleases NsiI and EcoRI and again recovered by the GENECLEAN® procedure (Bio101, Inc., P.O. Box 2284, La Jolla, Calif.). The fragment was purified by electrophoresis in 1.5% low melting agarose (BioRad). DNA was recovered from the excised gel band by the GENECLEAN® procedure (Bio101, Inc., P.O. Box 2284, La Jolla, Calif.). This fragment was substituted for the analogous fragment in pPIC9. For this purpose, pPIC9 was digested with endonucleases NsiI and EcoRI. The larger fragment was purified by electrophoresis in a 1.2% low melting agarose gel and recovered from the excised gel band by the GENECLEAN® procedure (Bio101, Inc., P.O. Box 2284, La Jolla, Calif.).

The PCR fragment and the large pPIC9 fragment were ligated under standard conditions, and the ligation was used to transform *E. coli* HB101. Ampicillin resistant transformants containing the correct plasmid were identified by screening plasmid DNA for the absence of the BamHI site. The correct plasmid was designated pFP734. The DNA sequence of pFP734 in the affected region, verified by DNA sequencing is shown in FIG. 19 (SEQ ID NOs.:96 and 97).

DNA sequences encoding six consecutive histidine residues were inserted into pHIL-D4. Such sequences were carried on a synthetic double stranded oligonucleotide (SF47/48) with the following sequence:

```
                                            SEQ ID NO.:102
         M  G  S  H  H  H  H  H End
                                            SEQ ID NO.:103
5'HO-AATTATGGGATCCCATCACCATCACCATCACT
                                            SEQ ID NO.:104
         TACCCTAGGGTAGTGGTAGTGGTAGTGATTAA-OH 5'
```

The amino acid sequence encoded by this oligonucleotide when it is inserted in the correct orientation into the EcoRI site of pHIL-D4 is shown in one-letter code above the DNA sequence. DNA of pHILD4 was digested with endonuclease EcoRI and recovered by the GENECLEAN® procedure (Bio101, Inc., P.O. Box 2284, La Jolla, Calif.). An aliquot of this digested DNA (approximately 0.02 pmoles) was mixed with oligonucleotide SF47/48 (10 pmoles), the 5' termini of which had not been phosphorylated. After incubation under ligation conditions for 19 h at 4° C., an aliquot was used to transform *E. coli* HB101. Transformants were selected for ampicillin resistance and plasmid DNA of individual transformants was analyzed following digestion with endonucleases PvuII and BamHI. A correct plasmid was identified by the presence in the digest of a DNA band indicative of the BamHI site at the promoter-proximal end of the oligonucleotide sequence, resulting from insertion in the desired orientation. This plasmid was designated pFP684. Correct insertion of the oligonucleotide was verified by direct DNA sequencing.

The plasmid vector pFP743 was constructed in an analogous manner, by substituting for sequences between NotI and EcoRI sites in pFP734 a synthetic double stranded oligonucleotide (SF55/56) with the following sequence:

```
                                            SEQ ID NO.:105
         F  G  S  Q  G  A End
                                            SEQ ID NO.:106
5'HO-AATTCGGATCCCAGGGTGCTTAA
                                            SEQ ID NO.:107
         GCCTAGGGTCCCACGAATTCCGG-OH 5'
```

DNA of pFP734 was digested with endonucleases NotI and EcoRI, then recovered by the GENECLEAN® procedure (Bio101, Inc., P.O. Box 2284, La Jolla, Calif.). Oligonucleotide SF55/56 was inserted by ligation as described above. A correct plasmid was identified by the presence of a new fragment upon digesting plasmid DNA with endonucleases BamHI and BglII, and designated pFP743. Correct oligonucleotide insertion was verified by direct DNA sequencing.

(2) DP-1B.33 Strains

Next, sequences encoding DP-1B were inserted into pFP684 and pFP743 at the respective unique BamHI sites located between the AOX1 promoter and sequences encoding the His6 oligomer. DNA (approximately 2 micrograms) of plasmids pFP717 (encoding 8 repeats of 101 aa DP-1B) and pFP719 (encoding 16 repeats of 101 aa DP-1B) were digested with endonuclease BamHI and BglII. The digests were fractionated by electrophoresis in low-melting agarose, and the ethidium bromide-stained band carrying the DP-1B-encoding sequences was identified by size and excised. The excised gel bands were melted, and to each was added an aliquot of pFP684 or pFP743 DNA that had been digested with endonuclease BamHI. DNA was recovered by the GENECLEAN® procedure (Bio101, Inc., P.O. Box 2284, La Jolla, Calif.) and incubated under ligation conditions for 3 h at 13° C. An aliquot of ligated DNA was used to transform E. coli HB101, and transformants were selected for resistance to ampicillin.

Individual transformants were screened by digesting plasmid DNA with endonucleases BamHI and BglII. Correct plasmids were identified by the presence of a fragment of the expected size containing the DP-1B.33 gene. Plasmids derived from the vector pFP684 were designated pFP728 (encoding 8 repeats of 101 amino acids DP-1B) and pFP732 (encoding 16 repeats of 101 amino acids DP-1B). Those derived from the vector pFP743 were designated pFP748 (encoding 8 repeats of 101 amino acids DP-1B) and pFP752 (encoding 16 repeats of 101 amino acids DP-1B).

Each of these plasmids was used to transfer the DP-1B gene to *Pichia pastoris* strain GS115 (his4) by spheroplast transformation essentially according to Cregg et al. (Mol. Cell. Biol. 5, 3376–3385 (1985)). The Pichia strain was grown in 200 ml YPD medium in a 500 ml baffled flask at 30° C. to $A_{600nm}$ of 0.3 to 0.4. Cells were harvested by centrifugation at 1500×g for 5 min at room temperature, then washed with 20 ml sterile water, followed by 20 ml fresh SED (1 M sorbitol, 25 mM EDTA, pH 8.0, 50 mM DTT), and 20 ml 1 M sorbitol. Cells were resuspended in 20 ml SCE (1 M sorbitol, 1 mM EDTA, 10 mM sodium citrate, pH 5.8), and zymolyase (15 ml stock solution containing 3 mg/ml Yeast Lytic Enzyme from Arthrobacter luteus (ICN Corp.; specific activity 100,000 u/g)) was added. Spheroplasting was monitored by diluting 0.2 ml aliquots into 0.8 ml 5% SDS and measuring $A_{600nm}$. Digestion was continued until 70–80% spheroplasting was obtained. Spheroplasts were then harvested by centrifugation at 750×g for 10 min at room temperature, washed once with 10 ml 1 M sorbitol and once with 10 ml CAS (1 M sorbitol, 10 mM Tris-HCl, pH 7.5, 10 mM $CaCl_2$), and finally resuspended in 0.6 ml CAS. To 0.1 ml spheroplast suspension was added 1–5 micrograms linear DNA fragments in CAS, prepared by digesting plasmid DNA with endonuclease BglII and recovering the fragments by the GENECLEAN® procedure (Bio101, Inc., P.O. Box 2284, La Jolla, Calif.). PEG solution (1 ml containing 20% w/v PEG 3350 (Fisher Scientific Co,) in 10 mM Tris-HCl, pH 7.5, 10 mM $CaCl_2$) was added, mixed gently, and incubated 10 min at room temperature. Spheroplasts were recovered by centrifugation as above. The drained pellet was resuspended in 0.15 ml SOS (1 M sorbitol, 0.3 vol/vol medium YPD, 10 mM $CaCl_2$, incubated at room temperature 20 min, and diluted with 0.85 ml 1 M sorbitol. Washed spheroplasts were mixed with 15 ml RD agarose (containing, per liter: 186 g sorbitol, 10 g agarose, 20 g D-glucose, 13.4 g yeast nitrogen base without amino acids (Difco), 0.4 mg biotin, 50 mg each L-glutamic acid, L-methionine, L-lysine, L-leucine, L-isoleucine, and 20 ml 50× His assay medium. The composition of 50× His assay medium was as follows (per liter): 50 g D-glucose, 40 g sodium acetate, 6 g ammonium chloride, 0.4 g D,L-alanine, 0.48 g L-arginine-HCl, 0.8 g L-asparagine monohydrate, 0.2 g L-aspartic acid, 0.6 g L-glutamic acid, 0.2 g glycine, 0.2 g D,L-phenylalanine, 0.2 g L-proline, 0.1 g D,L-serine, 0.4 g D,L-threonine, 0.5 g D,L-valine, 20 mg adenine sulfate, 20 mg guanine hydrochloride, 20 mg uracil, 20 mg xanthine, 1 mg thiamine-HCl, 0.6 mg pyridoxine-HCl, 0.6 mg pyridoxamine-HCl, 0.6 mg pyridoxal-HCl, 1 mg Ca pantothenate, 2 mg riboflavin, 2 mg nicotinic acid, 0.2 mg para-aminobenzoic acid, 0.002 mg biotin, 0.002 mg folic acid, 12 g monopotassium phosphate, 12 g dipotassium phosphate, 4 g magnesium sulfate, 20 mg ferrous sulfate, 4 mg manganese sulfate, 20 mg sodium chloride, 100 mg L-cystine, 80 mg D,L-tryptophane, 200 mg L-tyrosine. Spheroplasts in RD agarose (5 ml aliquots)were plated on RDB plates with the same composition as RD, but with 20 g agar (Difco) per liter in place of agarose.

Plates were incubated at 30° C. for 3–4 days. Histidine prototrophic transformants were picked and patched onto MGY plates containing (per liter) 15 g agar, 13.4 g yeast nitrogen base without amino acids, 0.4 mg biotin, 10 ml glycerol. Replicas were patched onto a sheet of cellulose acetate on the surface of MGY agar. After 2 days growth at 30° C., the cellulose acetate was transferred to a second plate on which a sheet of nitrocellulose had been placed on the surface of MM agar with the same composition as MGY except 0.5% v/v methanol instead of glycerol. After incubation for 1–3 days at 30° C., the nitrocellulose sheet was removed from under the cellulose acetate, blocked with "Blotto", and developed by immunochemical staining with anti-DP-1 serum as described above. Positive transformants, identified by blue color in this colony immunoassay, were picked from the MGY master plate. Transformants were also tested for growth on MM agar. DP-1 protein produced by immunoassay positive strains was assayed by Western blot analysis as described above. Several were shown to produce full-length protein of the expected size, detected by anti-DP-1 serum.

(2) DP-1B Production

Figure 20:
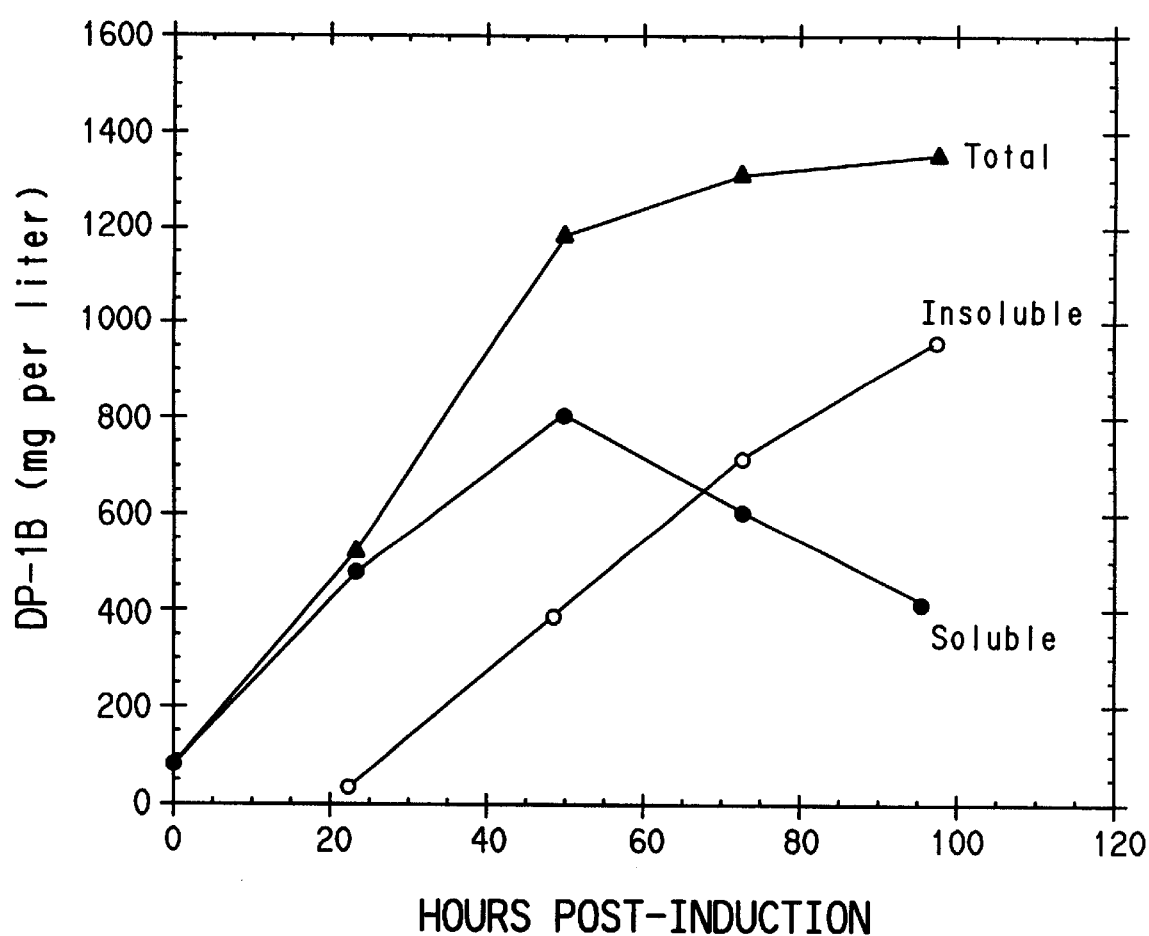
FIG. 20 illustrates DP-1B production by *P. pastoris* strain YFP5028.
Figure 21:
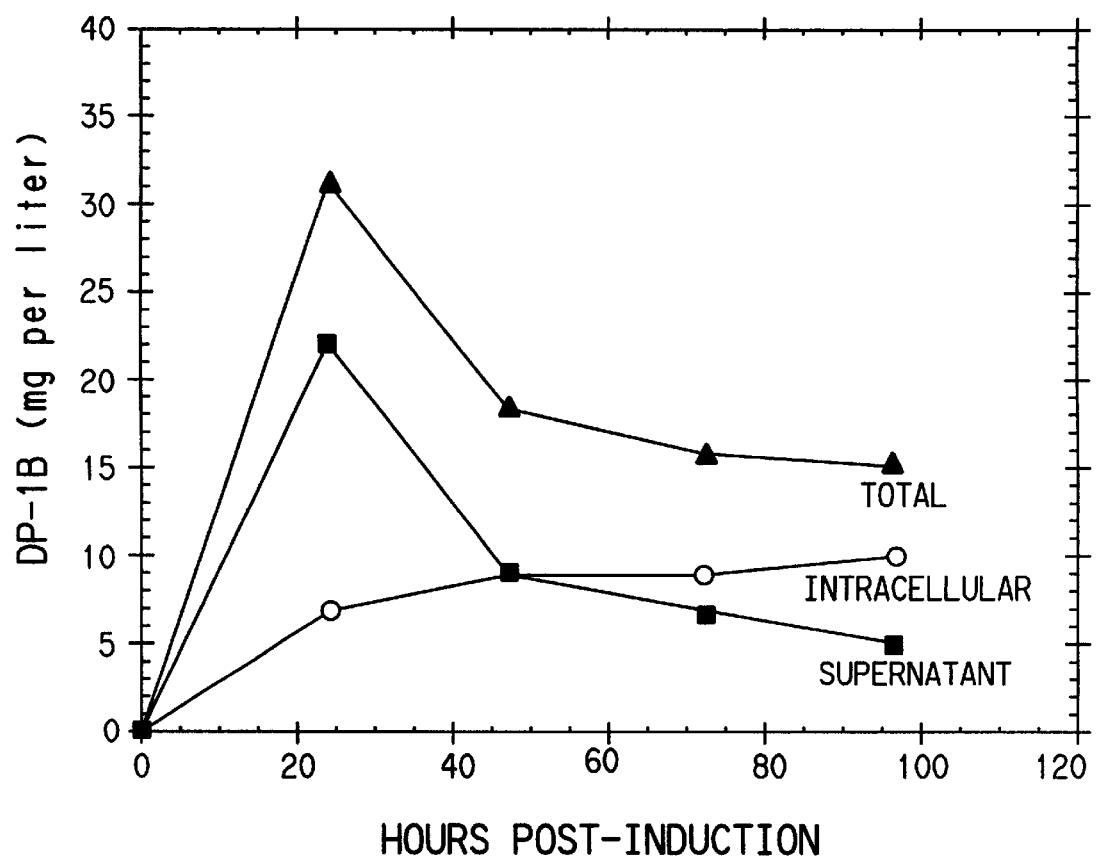
FIG. 21 illustrates DP-1B production by *P. pastoris* strain YFP5093.

DP-1B production by two such transformants is illustrated in FIGS. 20 and 21. FIG. 20 shows intracellular production, after various times of methanol induction, by strain YFP5028, which was derived by transforming *Pichia pastoris* GS115 with plasmid pFP728. This strain produces DP-1B species of 5 different sizes, as indicated by Western blot analysis, consisting of 8, 11, 13, 15 and greater than 20 repeats of the 101-amino acid residue monomer, respectively. It was identified among Pichia transformants by its ability to grow on YPD medium containing 0.5 mg/ml antibiotic G418, presumably indicative of the presence of multiple copies of the pFP728-derived insert. Total production of DP-1B was in excess of 1 g per liter culture. FIG. 21 shows the intracellular and extracellular production of DP-1B by strain YFP5093, which was derived by transformation of *Pichia pastoris* GS115 with plasmid pFP748. A significant fraction of the DP-LB produced was recovered from the extracellular culture supernatant.

Example 8

Demonstration of the Solutioning and Extrusion of Fibers from a Recombinantly Synthesized Analog to Spider Dragline Protein For fiber spinning, DP-1B was purified by ion exchange chromatography. Frozen cell paste of *E. coli* FP3350 was thawed, suspended in 0.02 M Tris-HCl buffer, pH 8.0 (Buffer A), and lysed by passage through a Mantin-Gaulin homogenizer (3–4 passes). Cell debris was removed by centrifugation, and the soluble extract was heated to 60° C. for 15-min. Insoluble material was again removed by centrufugation, and the soluble heat-treated extract was adjusted to pH 8.0 and diluted to conductivity less than 0.025M applied to a column of SP-Sepharose Fast Flow (Pharmacia, Piscataway, N.J.) equilibrated with Buffer A. The column was washed with Buffer A and eluted with a linear gradient from 0 to 0.5 M NaCl in Buffer A. DP-1B-containing fractions were identified by gel electrophoresis and immunoblotting as described above, pooled, and DP-LB was recovered by precipitation with 4 volumes of methanol at 0° C. and centrifugation. Pellets were washed three times with methanol and dried in vacuum. This material was found to be greater than 95% pure DP-1B as determined by amino acid analysis.

Briefly, the process of producing useful fibers from purified DP-1 protein involves the steps of dissolution in HFIP, followed by spinning of the solution through a spinneret orifice to obtain fibers. Physical properties such as tenacity, elongation, and initial modulus were measured using methods and instruments which conformed to ASTM Standard D 2101-82, except that the test specimen length was one inch. Five breaks per sample were made for each test.

Wet Spinning of Silk Fibers from HFIP Solution:

DP-1 was added to hexafluoroisopropanol (HFIP) in a polyethylene syringe to make a 20% solution of DP-1 in HFIP. The solution was mixed thoroughly, by pumping back and forth between two syringes and allowed to stand overnight.

The 20% solids solution of DP-1 in HFIP was transferred to a syringe fitted with a scintered stainless steel DYNAL-LOG® filter (X7). The syringe was capped and periodically vented to disengage air bubbles trapped in the solution. A syringe pump was then used to force the solution through the filter and out of the syringe through a 5 mil diameter by 4 mil length orifice in a stainless steel spinneret through a 3.5 inch air gap into the container of isopropanol at 20° C. The filament which formed as the solution was extruded into the isopropanol at 8.3 fpm and was wound on a bobbin at 11 fpm.

The spun filament was allowed to stand in isopropanol overnight. Then, the filament was drawn while still wet to 2× its length at 150° C. in a tube furnace. The drawn fiber was then allowed to dry in room air.

Physical testing of samples of the dry fiber showed them to be 16.7 denier, with tenacities of 1.22 gpd, elongations of 103.3%, and initial moduli of 40.1 gpd. These figures indicate that the tenacity and modulus of the spun DP-1 spider silk variant fiber compares favorably with those of commercial textile fibers and is therefore considered to be a useful fiber.

I claim:

1. A nucleic acid molecule having the sequence selected from the group consisting of: SEQ ID NO:80, SEQ ID NO:81 SEQ ID NO:82 and SEQ ID NO:83.

2. A nucleic acid moleclue encoding a fiber-forming spider silk variant protein comprising from 1 to 16 tandem repeats of the polypeptide selected from the group consisting of SEQ ID NO:20, SEQ ID NO:22, SEQ ID NO:60 and SEQ ID NO:62.

3. A plasmid comprising the nucleic acid molecule of claim 2 operably and expressibly linked to a suitable promoter.

4. A plasmid as recited in claim 3 wherein the nucleic acid molecule is flanked on either the 5' end or the 3' end by a DNA fragment encoding a series of between 4 and 20 histidine residues.

5. A transformed host cell comprising the plasmid of claim 3 wherein the nucleic acid molecule is flanked on either the 5' end or the 3' end by a DNA fragment encoding a series of between 4 and 20 histidine residues.

6. A host cell transformed with a plasmid comprising the nucleic acid molecule of claim 2, the host cell capable of secreting spider silk variant protein into the cell growth media.

7. A nucleic acid molecule comprising from 1 to 16 tandem repeats of the nucleic acid selected from the group consisting of SEQ ID NO:80, SEQ ID NO:81, SEQ ID NO:82, and SEQ ID NO:83.

8. The transformed E. coli host FP3350 identified by the ATCC number ATCC 69328.

9. The transformed Bacillus subtilis host FP2193, identified by the ATCC number ATCC 69327.

10. A universal expression vector pFP204, useful for the expression of spider silk variant proteins, identified by the ATCC number ATCC 69326.

11. A spider dragline variant protein wherein the full length variant protein is defined by the formula:

[A[C]GQGGYGGLGXQGAGRGGLGGQGAGAnGG]z wherein X=S, G or N; n=0–7 and z=1–75, and wherein the value of z determines the number of repeats in the variant protein and wherein the formula encompasses variations selected from the group consisting of:

(a) when n=0, the sequence encompassing AGRGGLG-GQGAGAnGG is deleted;

(b) deletions other than the poly-alanine sequence, limited by the value of n will encompass integral multiples of three consecutive residues;

(c) the deletion of GYG in any repeat is accompanied by deletion of GRG in the same repeat; and (d) where a first repeat where n=0 is deleted, the first repeat is preceded by a second repeat where n=6; and wherein the full-length protein is encoded by a gene or genes and wherein said gene or genes are not endogenous to the Nephila clavipes genome.

12. A spider dragline variant protein wherein the full length silk variant protein is defined by the formula:

[GPGGYGPGQQGPGGYGPGQQGPGGYGPGQQGPSGPGSAn]z wherein n=6–10 and z=1–75 and wherein, excluding the poly-alanine sequence, individual repeats differ from the consensus repeat sequence by deletions of integral multiples of five consecutive residues consisting of one or both of the pentapeptide sequences GPGGY or GPGQQ and wherein the full-length protein is encoded by a gene or genes and wherein the gene or genes are not endogenous to the Nephila clavipes genome.

13. A transformed host cell comprising:
A) a host cell selected from the group consisting of E. coli, Bacillus subtilis, Saccharomyces cerevisiae, Schizosaccharomyces pombe, Pichia pastoris, Aspergillus sp., and Streptomyces sp.; and
B) a plasmid comprising a nucleic acid molecule
  i) selected from the group consisting of
    a) a nucleic acid molecule encoding a fiber-forming spider silk variant protein comprising from 1 to 16 tandem repeats of DP-1A.9 (SEQ ID NO:20);
    b) a nucleic acid molecule encoding a fiber-forming spider silk variant protein comprising from 1 to 16 tandem repeats of DP-1B.9 (SEQ ID NO:22);
    c) a nucleic acid molecule encoding a fiber-forming spider silk variant protein comprising from 1 to 16 tandem repeats of DP-1B.16 (SEQ ID NO:62); and
    d) A nucleic acid molecule encoding a fiber-forming spider silk variant protein comprising from 1 to 16 tandem repeats of DP-2A (SEQ ID NO:60) operably and expressibly linked to a suitable promoter; and
  ii) optionally flanked on either the 5' end or the 3' end by a DNA fragment encoding a series of between 4 and 20 histidine residues,wherein the plasmid expresses a spider silk variant protein at levels between 1 mg and 300 mg of full-length protein per gram of dry cell mass.

14. A polypeptide selected from the group consisting of SEQ ID NO:20, SEQ ID NO:22, SEQ ID NO:60, SEQ ID NO:62.

15. A polypeptide selected from the group consisting of SEQ ID NO:21, SEQ ID NO:23, SEQ ID NO:61, and SEQ ID NO:63.

16. A spider silk variant protein comprised of from 1 to 16 tandem repeats of a polypeptide selected from the group consisting of SEQ ID NO:21, SEQ ID NO:23, SEQ ID NO:61, and SEQ ID NO:63.

* * * * *

SEQUENCE LISTING (1) GENERAL INFORMATION:

(iii) NUMBER OF SEQUENCES: 107

(2) INFORMATION FOR SEQ ID NO:1:

(i) SEQUENCE CHARACTERISTICS:
      (A) LENGTH: 34 amino acids
      (B) TYPE: amino acid
      (C) STRANDEDNESS: unknown
      (D) TOPOLOGY: unknown (ii) MOLECULE TYPE: peptide (xi) SEQUENCE DESCRIPTION: SEQ ID NO:1:

```
Ala Gly Gln Gly Gly Tyr Gly Gly Leu Gly Xaa Gln Gly Ala Gly Arg
1               5                   10                  15

Gly Gly Leu Gly Gly Gln Gly Ala Gly Ala Ala Ala Ala Ala Ala
            20                  25                  30

Gly Gly
```

(2) INFORMATION FOR SEQ ID NO:2:

(i) SEQUENCE CHARACTERISTICS:
      (A) LENGTH: 15 amino acids
      (B) TYPE: amino acid
      (C) STRANDEDNESS: unknown
      (D) TOPOLOGY: unknown (ii) MOLECULE TYPE: peptide (xi) SEQUENCE DESCRIPTION: SEQ ID NO:2:

```
Ala Gly Arg Gly Gly Leu Gly Gly Gln Gly Ala Gly Ala Gly Gly
1               5                   10                  15
```

(2) INFORMATION FOR SEQ ID NO:3:

(i) SEQUENCE CHARACTERISTICS:
      (A) LENGTH: 5 amino acids
      (B) TYPE: amino acid (C) STRANDEDNESS: unknown
                (D) TOPOLOGY: unknown (ii) MOLECULE TYPE: peptide (xi) SEQUENCE DESCRIPTION: SEQ ID NO:3:

Gly Pro Gly Gly Tyr
1               5

(2) INFORMATION FOR SEQ ID NO:4:

(i) SEQUENCE CHARACTERISTICS:
                (A) LENGTH: 5 amino acids
                (B) TYPE: amino acid
                (C) STRANDEDNESS: unknown
                (D) TOPOLOGY: unknown (ii) MOLECULE TYPE: peptide (xi) SEQUENCE DESCRIPTION: SEQ ID NO:4:

Gly Pro Gly Gln Gln
1               5

(2) INFORMATION FOR SEQ ID NO:5:

(i) SEQUENCE CHARACTERISTICS:
                (A) LENGTH: 14 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:5:

ACGACCTCAT CTAT                                                         14

(2) INFORMATION FOR SEQ ID NO:6:

(i) SEQUENCE CHARACTERISTICS:
                (A) LENGTH: 14 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:6:

CTGCCTCTGT CATC                                                         14

(2) INFORMATION FOR SEQ ID NO:7:

(i) SEQUENCE CHARACTERISTICS:
                (A) LENGTH: 14 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:7:

AATAGGCGTA TCAC                                                         14

(2) INFORMATION FOR SEQ ID NO:8:

(i) SEQUENCE CHARACTERISTICS:
                (A) LENGTH: 19 amino acids
                (B) TYPE: amino acid
                (C) STRANDEDNESS: unknown
                (D) TOPOLOGY: unknown (ii) MOLECULE TYPE: peptide (xi) SEQUENCE DESCRIPTION: SEQ ID NO:8:

Gly Arg Gly Ala Gly Gln Ser Gly Leu Gly Gly Tyr Gly Gly Gln Gly
1               5                   10                  15

Ala Gly Cys (2) INFORMATION FOR SEQ ID NO:9:

(i) SEQUENCE CHARACTERISTICS:
            (A) LENGTH: 19 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:9:

Cys Gly Pro Gly Gln Gln Gly Pro Gly Gly Tyr Gly Pro Gly Gln Gln
1               5                   10                  15

Gly Pro Ser (2) INFORMATION FOR SEQ ID NO:10:

(i) SEQUENCE CHARACTERISTICS:
            (A) LENGTH: 10 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:10:

Gly Ser His His His His His His Ser Arg
1               5                   10

(2) INFORMATION FOR SEQ ID NO:11:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

GATCCCATCA CCATCACCAT CACTCTA                                    27

(2) INFORMATION FOR SEQ ID NO:12:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

GATCTAGAGT GATGGTGATG GTGATGG                                    27

(2) INFORMATION FOR SEQ ID NO:13:

(i) SEQUENCE CHARACTERISTICS:
            (A) LENGTH: 8 amino acids (B) TYPE: amino acid
          (C) STRANDEDNESS: unknown
          (D) TOPOLOGY: unknown (ii) MOLECULE TYPE: peptide (xi) SEQUENCE DESCRIPTION: SEQ ID NO:13:

Gly Ser His His His His His His
1               5

(2) INFORMATION FOR SEQ ID NO:14:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:14:

GATCCCATCA CCATCACCAT CACTAAA                                       27

(2) INFORMATION FOR SEQ ID NO:15:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:15:

GATCTTTAGT GATGGTGATG GTGATGG                                       27

(2) INFORMATION FOR SEQ ID NO:16:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:16:

GATCAGATAT CG                                                       12

(2) INFORMATION FOR SEQ ID NO:17:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:17:

GATCCGATAT CT                                                       12

(2) INFORMATION FOR SEQ ID NO:18:

(i) SEQUENCE CHARACTERISTICS:
          (A) LENGTH: 47 amino acids
          (B) TYPE: amino acid
          (C) STRANDEDNESS: unknown
          (D) TOPOLOGY: unknown (ii) MOLECULE TYPE: peptide (xi) SEQUENCE DESCRIPTION: SEQ ID NO:18:

```
Gly Pro Gly Gly Tyr Gly Pro Gly Gln Gln Pro Gly Gly Tyr Gly
1               5                  10                  15

Pro Gly Gln Gln Gly Pro Gly Gly Tyr Gly Pro Gly Gln Gln Gly Pro
            20                  25                  30

Ser Gly Pro Gly Ser Ala Ala Ala Ala Ala Ala Ala Ala
        35                  40                  45
```

(2) INFORMATION FOR SEQ ID NO:19:

(i) SEQUENCE CHARACTERISTICS:
        (A) LENGTH: 651 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:19:

```
Gln Gly Ala Gly Ala Ala Ala Ala Ala Gly Gly Ala Gly Gln Gly
1               5                  10                  15

Gly Tyr Gly Gly Leu Gly Gly Gln Gly Ala Gly Gln Gly Tyr Gly
            20                  25                  30

Gly Leu Gly Gly Gln Gly Ala Gly Gln Gly Ala Gly Ala Ala Ala
            35                  40                  45

Ala Ala Ala Gly Gly Ala Gly Gln Gly Gly Tyr Gly Gly Leu Gly Ser
        50                  55                  60

Gln Gly Ala Gly Arg Gly Gly Gln Gly Ala Gly Ala Ala Ala Ala
65                  70                  75                  80

Ala Gly Gly Ala Gly Gln Gly Gly Tyr Gly Gly Leu Gly Ser Gln Gly
                85                  90                  95

Ala Gly Arg Gly Gly Leu Gly Gly Gln Gly Ala Gly Ala Ala Ala Ala
                100                 105                 110

Ala Ala Ala Gly Gly Ala Gly Gln Gly Gly Tyr Gly Gly Leu Gly Asn
                115                 120                 125

Gln Gly Ala Gly Arg Gly Gly Gln Gly Ala Ala Ala Ala Ala Ala Gly
    130                 135                 140

Gly Ala Gly Gln Gly Gly Tyr Gly Gly Leu Gly Ser Gln Gly Ala Gly
145                 150                 155                 160

Arg Gly Gly Leu Gly Gly Gln Gly Ala Gly Ala Ala Ala Ala Ala
                165                 170                 175

Gly Gly Ala Gly Gln Gly Gly Tyr Gly Gly Leu Gly Gly Gln Gly Ala
                180                 185                 190

Gly Gln Gly Gly Tyr Gly Gly Leu Gly Ser Gln Gly Ala Gly Arg Gly
            195                 200                 205

Gly Leu Gly Gly Gln Gly Ala Gly Ala Ala Ala Ala Ala Ala Gly
            210                 215                 220

Gly Ala Gly Gln Gly Gly Leu Gly Gly Gln Gly Ala Gly Gln Gly Ala
225                 230                 235                 240

Gly Ala Ser Ala Ala Ala Ala Gly Gly Ala Gly Gln Gly Gly Tyr Gly
                245                 250                 255

Gly Leu Gly Ser Gln Gly Ala Gly Arg Gly Gly Glu Gly Ala Gly Ala
            260                 265                 270

Ala Ala Ala Ala Ala Gly Gly Ala Gly Gln Gly Gly Tyr Gly Gly Leu
```

```
              275                 280                 285
Gly Gly Gln Gly Ala Gly Gln Gly Gly Tyr Gly Gly Leu Gly Ser Gln
            290                 295                 300
Gly Ala Gly Arg Gly Gly Leu Gly Gly Gln Gly Ala Gly Ala Ala Ala
305                 310                 315                 320
Ala Gly Gly Ala Gly Gln Gly Gly Leu Gly Gly Gln Gly Ala Gly Gln
                325                 330                 335
Gly Ala Gly Ala Ala Ala Ala Ala Gly Gly Ala Gly Gln Gly Gly
            340                 345                 350
Tyr Gly Gly Leu Gly Ser Gln Gly Ala Gly Arg Gly Gly Leu Gly Gly
            355                 360                 365
Gln Gly Ala Gly Ala Val Ala Ala Ala Ala Gly Gly Ala Gly Gln
370                 375                 380
Gly Gly Tyr Gly Gly Leu Gly Ser Gln Gly Ala Gly Arg Gly Gly Gln
385                 390                 395                 400
Gly Ala Gly Ala Ala Ala Ala Ala Gly Gly Ala Gly Gln Arg Gly
            405                 410                 415
Tyr Gly Gly Leu Gly Asn Gln Gly Ala Gly Arg Gly Gly Leu Gly Gly
            420                 425                 430
Gln Gly Ala Gly Ala Ala Ala Ala Ala Gly Gly Ala Gly Gln
            435                 440                 445
Gly Gly Tyr Gly Gly Leu Gly Asn Gln Gly Ala Gly Arg Gly Gly Gln
            450                 455                 460
Gly Ala Ala Ala Ala Ala Gly Gly Ala Gly Gln Gly Gly Tyr Gly Gly
465                 470                 475                 480
Leu Gly Ser Gln Gly Ala Gly Arg Gly Gly Gln Gly Ala Gly Ala Ala
                485                 490                 495
Ala Ala Ala Val Gly Ala Gly Gln Glu Gly Ile Arg Gly Gln Gly
            500                 505                 510
Ala Gly Gln Gly Gly Tyr Gly Gly Leu Gly Ser Gln Gly Ser Gly Arg
515                 520                 525
Gly Gly Leu Gly Gly Gln Gly Ala Gly Ala Ala Ala Ala Ala Gly
            530                 535                 540
Gly Ala Gly Gln Gly Gly Leu Gly Gly Gln Gly Ala Gly Gln Gly Ala
545                 550                 555                 560
Gly Ala Ala Ala Ala Ala Gly Gly Val Arg Gln Gly Gly Tyr Gly
                565                 570                 575
Gly Leu Gly Ser Gln Gly Ala Gly Arg Gly Gly Gln Gly Ala Gly Ala
            580                 585                 590
Ala Ala Ala Ala Gly Gly Ala Gly Gln Gly Gly Tyr Gly Gly Leu
            595                 600                 605
Gly Gly Gln Gly Val Gly Arg Gly Gly Leu Gly Gly Gln Gly Ala Gly
610                 615                 620
Ala Ala Ala Gly Gly Ala Gly Gln Gly Gly Tyr Gly Gly Val Gly
625                 630                 635                 640
Ser Gly Ala Ser Ala Ala Ser Ala Ala Ala Ala
                645                 650

(2) INFORMATION FOR SEQ ID NO:20:

(i) SEQUENCE CHARACTERISTICS:
        (A) LENGTH: 101 amino acids
        (B) TYPE: amino acid
        (C) STRANDEDNESS: unknown
        (D) TOPOLOGY: unknown
```

(ii) MOLECULE TYPE: protein (xi) SEQUENCE DESCRIPTION: SEQ ID NO:20:

```
Gly Ala Gly Arg Gly Gly Gln Gly Ala Gly Ala Ala Ala Ala Ala Ala
1               5                   10                  15
Gly Gly Ala Gly Gln Gly Gly Tyr Gly Gly Leu Gly Ser Gln Gly Ala
            20                  25                  30
Gly Arg Gly Gly Leu Gly Gly Gln Gly Ala Gly Ala Ala Ala Ala Ala
        35                  40                  45
Ala Ala Gly Gly Ala Gly Gln Gly Gly Leu Gly Ser Gln Gly Ala Gly
50                  55                  60
Gln Gly Ala Gly Ala Ala Ala Ala Ala Ala Gly Gly Ala Gly Gln Gly
65                  70                  75                  80
Gly Tyr Gly Gly Leu Gly Ser Gln Gly Ala Gly Gln Gly Gly Tyr Gly
                85                  90                  95
Gly Leu Gly Ser Gln
                100
```

(2) INFORMATION FOR SEQ ID NO:21:

(i) SEQUENCE CHARACTERISTICS:
        (A) LENGTH: 606 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:21:

```
Gly Ala Gly Arg Gly Gly Gln Gly Ala Gly Ala Ala Ala Ala Ala Ala
1               5                   10                  15
Gly Gly Ala Gly Gln Gly Gly Tyr Gly Gly Leu Gly Ser Gln Gly Ala
            20                  25                  30
Gly Arg Gly Gly Leu Gly Gly Gln Gly Ala Gly Ala Ala Ala Ala Ala
        35                  40                  45
Ala Ala Gly Gly Ala Gly Gln Gly Gly Leu Gly Ser Gln Gly Ala Gly
50                  55                  60
Gln Gly Ala Gly Ala Ala Ala Ala Ala Ala Gly Gly Ala Gly Gln Gly
65                  70                  75                  80
Gly Tyr Gly Gly Leu Gly Ser Gln Gly Ala Gly Gln Gly Gly Tyr Gly
                85                  90                  95
Gly Leu Gly Ser Gln Gly Ala Gly Arg Gly Gly Gln Gly Ala Gly Ala
                100                 105                 110
Ala Ala Ala Ala Gly Gly Ala Gly Gln Gly Gly Tyr Gly Gly Leu
        115                 120                 125
Gly Ser Gln Gly Ala Gly Arg Gly Gly Leu Gly Gly Gln Gly Ala Gly
    130                 135                 140
Ala Ala Ala Ala Ala Ala Gly Gly Ala Gly Gln Gly Gly Leu Gly
145                 150                 155                 160
Ser Gln Gly Ala Gly Gln Gly Ala Gly Ala Ala Ala Ala Ala Ala Gly
                165                 170                 175
Gly Ala Gly Gln Gly Gly Tyr Gly Gly Leu Gly Ser Gln Gly Ala Gly
            180                 185                 190
Gln Gly Gly Tyr Gly Gly Leu Gly Ser Gln Gly Ala Gly Arg Gly Gly
        195                 200                 205
Gln Gly Ala Gly Ala Ala Ala Ala Ala Ala Gly Gly Ala Gly Gln Gly
```

-continued

```
            210                 215                 220
Gly Tyr Gly Gly Leu Gly Ser Gln Gly Ala Gly Arg Gly Gly Leu Gly
225                 230                 235                 240
Gly Gln Gly Ala Gly Ala Ala Ala Ala Ala Ala Gly Gly Ala Gly
                245                 250                 255
Gln Gly Gly Leu Gly Ser Gln Gly Ala Gly Gln Gly Ala Gly Ala Ala
                260                 265                 270
Ala Ala Ala Ala Gly Gly Ala Gly Gln Gly Gly Tyr Gly Gly Leu Gly
            275                 280                 285
Ser Gln Gly Ala Gly Gln Gly Gly Tyr Gly Gly Leu Gly Ser Gln Gly
            290                 295                 300
Ala Gly Arg Gly Gly Gln Gly Ala Gly Ala Ala Ala Ala Ala Ala Gly
305                 310                 315                 320
Gly Ala Gly Gln Gly Gly Tyr Gly Gly Leu Gly Ser Gln Gly Ala Gly
                325                 330                 335
Arg Gly Gly Leu Gly Gly Gln Gly Ala Gly Ala Ala Ala Ala Ala Ala
                340                 345                 350
Ala Gly Gly Ala Gly Gln Gly Gly Leu Gly Ser Gln Gly Ala Gly Gln
            355                 360                 365
Gly Ala Gly Ala Ala Ala Ala Ala Gly Gly Ala Gly Gln Gly Gly
            370                 375                 380
Tyr Gly Gly Leu Gly Ser Gln Gly Ala Gly Gln Gly Gly Tyr Gly Gly
385                 390                 395                 400
Leu Gly Ser Gln Gly Ala Gly Arg Gly Gly Gln Gly Ala Gly Ala Ala
                405                 410                 415
Ala Ala Ala Ala Gly Gly Ala Gly Gln Gly Gly Tyr Gly Gly Leu Gly
            420                 425                 430
Ser Gln Gly Ala Gly Arg Gly Gly Leu Gly Gly Gln Gly Ala Gly Ala
            435                 440                 445
Ala Ala Ala Ala Ala Gly Gly Ala Gly Gln Gly Gly Leu Gly Ser
            450                 455                 460
Gln Gly Ala Gly Gln Gly Ala Gly Ala Ala Ala Ala Ala Ala Gly Gly
465                 470                 475                 480
Ala Gly Gln Gly Gly Tyr Gly Gly Leu Gly Ser Gln Gly Ala Gly Gln
                485                 490                 495
Gly Gly Tyr Gly Gly Leu Gly Ser Gln Gly Ala Gly Arg Gly Gly Gln
                500                 505                 510
Gly Ala Gly Ala Ala Ala Ala Ala Gly Gly Ala Gly Gln Gly Gly
            515                 520                 525
Tyr Gly Gly Leu Gly Ser Gln Gly Ala Gly Arg Gly Gly Leu Gly Gly
            530                 535                 540
Gln Gly Ala Gly Ala Ala Ala Ala Ala Ala Gly Gly Ala Gly Gln
545                 550                 555                 560
Gly Gly Leu Gly Ser Gln Gly Ala Gly Gln Gly Ala Gly Ala Ala Ala
                565                 570                 575
Ala Ala Ala Gly Gly Ala Gly Gln Gly Gly Tyr Gly Gly Leu Gly Ser
                580                 585                 590
Gln Gly Ala Gly Gln Gly Gly Tyr Gly Gly Leu Gly Ser Gln
            595                 600                 605
```

(2) INFORMATION FOR SEQ ID NO:22:

(i) SEQUENCE CHARACTERISTICS:
        (A) LENGTH: 101 amino acids (B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:22:

```
Gly Ala Gly Gln Gly Gly Tyr Gly Gly Leu Gly Ser Gln Gly Ala Gly
  1               5                  10                  15
Arg Gly Gly Leu Gly Gly Gln Gly Ala Gly Ala Ala Ala Ala Ala Ala
                 20                  25                  30
Ala Gly Gly Ala Gly Gln Gly Gly Leu Gly Ser Gln Gly Ala Gly Gln
             35                  40                  45
Gly Ala Gly Ala Ala Ala Ala Ala Ala Gly Gly Ala Gly Gln Gly Gly
     50                  55                  60
Tyr Gly Gly Leu Gly Ser Gln Gly Ala Gly Arg Gly Gly Gln Gly Ala
 65                  70                  75                  80
Gly Ala Ala Ala Ala Ala Ala Gly Gly Ala Gly Gln Gly Gly Tyr Gly
                 85                  90                  95
Gly Leu Gly Ser Gln
            100
```

(2) INFORMATION FOR SEQ ID NO:23:

(i) SEQUENCE CHARACTERISTICS:
       (A) LENGTH: 606 amino acids
       (B) TYPE: amino acid
       (C) STRANDEDNESS: unknown
       (D) TOPOLOGY: unknown (ii) MOLECULE TYPE: protein (xi) SEQUENCE DESCRIPTION: SEQ ID NO:23:

```
Gly Ala Gly Gln Gly Gly Tyr Gly Gly Leu Gly Ser Gln Gly Ala Gly
  1               5                  10                  15
Arg Gly Gly Leu Gly Gly Gln Gly Ala Gly Ala Ala Ala Ala Ala Ala
                 20                  25                  30
Ala Gly Gly Ala Gly Gln Gly Gly Leu Gly Ser Gln Gly Ala Gly Gln
             35                  40                  45
Gly Ala Gly Ala Ala Ala Ala Ala Ala Gly Gly Ala Gly Gln Gly Gly
     50                  55                  60
Tyr Gly Gly Leu Gly Ser Gln Gly Ala Gly Arg Gly Gly Gln Gly Ala
 65                  70                  75                  80
Gly Ala Ala Ala Ala Ala Ala Gly Gly Ala Gly Gln Gly Gly Tyr Gly
                 85                  90                  95
Gly Leu Gly Ser Gln Gly Ala Gly Gln Gly Gly Tyr Gly Gly Leu Gly
            100                 105                 110
Ser Gln Gly Ala Gly Arg Gly Gly Leu Gly Gly Gln Gly Ala Gly Ala
        115                 120                 125
Ala Ala Ala Ala Ala Gly Gly Ala Gly Gln Gly Gly Leu Gly Ser
    130                 135                 140
Gln Gly Ala Gly Gln Gly Ala Gly Ala Ala Ala Ala Ala Ala Gly Gly
145                 150                 155                 160
Ala Gly Gln Gly Gly Tyr Gly Gly Leu Gly Ser Gln Gly Ala Gly Arg
                165                 170                 175
Gly Gly Gln Gly Ala Gly Ala Ala Ala Ala Ala Ala Gly Gly Ala Gly
            180                 185                 190
Gln Gly Gly Tyr Gly Gly Leu Gly Ser Gln Gly Ala Gly Gln Gly Gly
```

```
                195                 200                     205
Tyr Gly Gly Leu Gly Ser Gln Gly Ala Gly Arg Gly Gly Leu Gly Gly
    210                 215                 220
Gln Gly Ala Gly Ala Ala Ala Ala Ala Ala Gly Gly Ala Gly Ala Gln
225                 230                     235                 240
Gly Gly Leu Gly Ser Gln Gly Ala Gly Gln Gly Ala Gly Ala Ala Ala
                245                 250                 255
Ala Ala Ala Gly Gly Ala Gly Gln Gly Gly Tyr Gly Gly Leu Gly Ser
                260                 265                 270
Gln Gly Ala Gly Arg Gly Gly Gln Gly Ala Gly Ala Ala Ala Ala Ala
            275                 280                 285
Ala Gly Gly Ala Gly Gln Gly Gly Tyr Gly Gly Leu Gly Ser Gln Gly
    290                 295                 300
Ala Gly Gln Gly Gly Tyr Gly Gly Leu Gly Ser Gln Gly Ala Gly Arg
305                 310                 315                 320
Gly Gly Leu Gly Gly Gln Gly Ala Gly Ala Ala Ala Ala Ala Ala Ala
                325                 330                 335
Gly Gly Ala Gly Gln Gly Gly Leu Gly Ser Gln Gly Ala Gly Gln Gly
            340                 345                 350
Ala Gly Ala Ala Ala Ala Ala Gly Gly Ala Gly Gln Gly Gly Tyr
    355                 360                 365
Gly Gly Leu Gly Ser Gln Gly Ala Gly Arg Gly Gly Gln Gly Ala Gly
    370                 375                 380
Ala Ala Ala Ala Ala Ala Gly Gly Ala Gly Gln Gly Gly Tyr Gly Gly
385                 390                 395                 400
Leu Gly Ser Gln Gly Ala Gly Gln Gly Gly Tyr Gly Gly Leu Gly Ser
                405                 410                 415
Gln Gly Ala Gly Arg Gly Gly Leu Gly Gly Gln Gly Ala Gly Ala Ala
            420                 425                 430
Ala Ala Ala Ala Ala Gly Gly Ala Gly Gln Gly Gly Leu Gly Ser Gln
            435                 440                 445
Gly Ala Gly Gln Gly Ala Gly Ala Ala Ala Ala Ala Gly Gly Ala
    450                 455                 460
Gly Gln Gly Gly Tyr Gly Gly Leu Gly Ser Gln Gly Ala Gly Arg Gly
465                 470                 475                 480
Gly Gln Gly Ala Gly Ala Ala Ala Ala Ala Gly Gly Ala Gly Gln
                485                 490                 495
Gly Gly Tyr Gly Gly Leu Gly Ser Gln Gly Ala Gly Gln Gly Gly Tyr
            500                 505                 510
Gly Gly Leu Gly Ser Gln Gly Ala Gly Arg Gly Gly Leu Gly Gly Gln
    515                 520                 525
Gly Ala Gly Ala Ala Ala Ala Ala Ala Gly Gly Ala Gly Gln Gly
    530                 535                 540
Gly Leu Gly Ser Gln Gly Ala Gly Gln Gly Ala Gly Ala Ala Ala Ala
545                 550                 555                 560
Ala Ala Gly Gly Ala Gly Gln Gly Gly Tyr Gly Gly Leu Gly Ser Gln
                565                 570                 575
Gly Ala Gly Arg Gly Gly Gln Gly Ala Gly Ala Ala Ala Ala Ala
            580                 585                 590
Gly Gly Ala Gly Gln Gly Gly Tyr Gly Gly Leu Gly Ser Gln
    595                 600                 605

(2) INFORMATION FOR SEQ ID NO:24:
```

(i) SEQUENCE CHARACTERISTICS:
            (A) LENGTH:  93 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:24:

GGGCCGGACG TGGTGGCCTT GGTGGTCAGG GTGCTGGCGC GGCAGCCGCT GCGGCAGCTG    60

GTGGTGCTGG TCAGGGCGGT CTTGGCTCAC AAG                                93

(2) INFORMATION FOR SEQ ID NO:25:

(i) SEQUENCE CHARACTERISTICS:
            (A) LENGTH:  93 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:25:

GTGAGCCAAG ACCGCCCTGA CCAGCACCAC CAGCTGCCGC AGCGGCTGCC GCGCCAGCAC    60

CCTGACCACC AAGGCCACCA CGTCCGGCCC CTT                                93

(2) INFORMATION FOR SEQ ID NO:26:

(i) SEQUENCE CHARACTERISTICS:
            (A) LENGTH:  31 amino acids
            (B) TYPE:  amino acid
            (C) STRANDEDNESS:  unknown
            (D) TOPOLOGY:  unknown (ii) MOLECULE TYPE:  peptide (xi) SEQUENCE DESCRIPTION:  SEQ ID NO:26:

Gly Ala Gly Arg Gly Gly Leu Gly Gly Gln Gly Ala Gly Ala Ala Ala
1               5                   10                  15

Ala Ala Ala Ala Gly Gly Ala Gly Gln Gly Gly Leu Gly Ser Gln
            20                  25                  30

(2) INFORMATION FOR SEQ ID NO:27:

(i) SEQUENCE CHARACTERISTICS:
            (A) LENGTH:  81 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:27:

GGGCCGGTCA AGGCGCTGGT GCAGCAGCAG CTGCCGCTGG CGGTGCAGGC CAAGGTGGAT    60

ATGGTGGCTT AGGGTCACAA G                                             81

(2) INFORMATION FOR SEQ ID NO:28:

(i) SEQUENCE CHARACTERISTICS:
            (A) LENGTH:  81 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION: SEQ ID NO:28:

GTGACCCTAA GCCACCATAT CCACCTTGGC CTGCACCGCC AGCGGCAGCT GCTGCTGCAC    60

CAGCGCCTTG ACCGGCCCCT T    81

(2) INFORMATION FOR SEQ ID NO:29:

(i) SEQUENCE CHARACTERISTICS:
        (A) LENGTH: 27 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:29:

Gly Ala Gly Gln Gly Ala Gly Ala Ala Ala Ala Ala Gly Gly Ala
1               5                   10                  15

Gly Gln Gly Gly Tyr Gly Gly Leu Gly Ser Gln
            20                  25

(2) INFORMATION FOR SEQ ID NO:30:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

GGGCCGGTCG AGGTGGACAA GGTGCAGGTG CAGCCGCTGC TGCTGCGGGC GGCGCAGGTC    60

AAGGTGGGTA TGGGGGTTTA GGTTCACAAG    90

(2) INFORMATION FOR SEQ ID NO:31:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

GTGAACCTAA ACCCCATAC CCACCTTGAC CTGCGCCGCC CGCAGCAGCA GCGGCTGCAC    60

CTGCACCTTG TCCACCTCGA CCGGCCCCTT    90

(2) INFORMATION FOR SEQ ID NO:32:

(i) SEQUENCE CHARACTERISTICS:
        (A) LENGTH: 30 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:32:

Gly Ala Gly Arg Gly Gly Gln Gly Ala Gly Ala Ala Ala Ala Ala
1               5                   10                  15

Gly Gly Ala Gly Gln Gly Gly Tyr Gly Gly Leu Gly Ser Gln
            20                  25                  30

(2) INFORMATION FOR SEQ ID NO:33:

(i) SEQUENCE CHARACTERISTICS:
        (A) LENGTH:  39 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:33:

```
GGGCCGGGCA AGGTGGTTAC GGCGGTCTCG GATCACAAG                39
```

(2) INFORMATION FOR SEQ ID NO:34:

(i) SEQUENCE CHARACTERISTICS:
        (A) LENGTH:  39 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:34:

```
GTGATCCGAG ACCGCCGTAA CCACCTTGCC CGGCCCCTT                39
```

(2) INFORMATION FOR SEQ ID NO:35:

(i) SEQUENCE CHARACTERISTICS:
        (A) LENGTH:  13 amino acids
        (B) TYPE:  amino acid
        (C) STRANDEDNESS:  unknown
        (D) TOPOLOGY:  unknown (ii) MOLECULE TYPE:  peptide (xi) SEQUENCE DESCRIPTION:  SEQ ID NO:35:

```
Gly Ala Gly Gln Gly Gly Tyr Gly Gly Leu Gly Ser Gln
1               5                   10
```

(2) INFORMATION FOR SEQ ID NO:36:

(i) SEQUENCE CHARACTERISTICS:
        (A) LENGTH:  32 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:36:

```
GATCTGCGGC CAAGGGGCC CACAAGGTGA GG                        32
```

(2) INFORMATION FOR SEQ ID NO:37:

(i) SEQUENCE CHARACTERISTICS:
        (A) LENGTH:  32 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:37:

```
ACGCCGGGTT CCCCGGGTGT TCCACTCCCT AG                       32
```

(2) INFORMATION FOR SEQ ID NO:38:

(i) SEQUENCE CHARACTERISTICS:

(A) LENGTH: 9 amino acids
    (B) TYPE: amino acid
    (C) STRANDEDNESS: unknown
    (D) TOPOLOGY: unknown (ii) MOLECULE TYPE: peptide (xi) SEQUENCE DESCRIPTION: SEQ ID NO:38:

Ser Ala Ala Gln Gly Ala His Lys Val
1               5

(2) INFORMATION FOR SEQ ID NO:39:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

GGATCCCATC ACCATCACCA TCACTCTAGA TCCGGCTGCT AA                           42

(2) INFORMATION FOR SEQ ID NO:40:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:40:

Gly Ser His His His His His His Ser Arg Ser Gly Cys
1               5                   10

(2) INFORMATION FOR SEQ ID NO:41:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

GATCTCCCGG GCCATCCGGC CCAGGTTCTG CGGCAGCGGC AGCAGCGGGC CCAGGGCAGC        60

AGCTGG                                                                  66

(2) INFORMATION FOR SEQ ID NO:42:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

GATCCCAGCT GCTGCCCTGG GCCCGCTGCT GCCGCTGCCG CAGAACCTGG GCCGGATGGC        60

CCGGGA                                                                  66

(2) INFORMATION FOR SEQ ID NO:43:

(i) SEQUENCE CHARACTERISTICS:
      (A) LENGTH: 21 amino acids
      (B) TYPE: amino acid
      (C) STRANDEDNESS: unknown
      (D) TOPOLOGY: unknown (ii) MOLECULE TYPE: peptide (xi) SEQUENCE DESCRIPTION: SEQ ID NO:43:

```
Ser Pro Gly Pro Ser Gly Pro Gly Ser Ala Ala Ala Ala Ala Gly
1               5                   10                  15

Pro Gly Gln Gln Leu
            20
```

(2) INFORMATION FOR SEQ ID NO:44:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

GATCTCCCGG GCCGGGCGGT TACGGTCCGG GTCAGCAAGG CCCAGGTGGC TACGGCCCAG      60

GCCAACAGCT GG      72

(2) INFORMATION FOR SEQ ID NO:45:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

GATCCCAGCT GTTGGCCTGG GCCGTAGCCA CCTGGGCCTT GCTGACCCGG ACCGTAACCG      60

CCCGGCCCGG GA      72

(2) INFORMATION FOR SEQ ID NO:46:

(i) SEQUENCE CHARACTERISTICS:
        (A) LENGTH: 23 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:46:

```
Ser Pro Gly Pro Gly Gly Tyr Gly Pro Gly Gln Gln Gly Pro Gly Gly
1               5                   10                  15

Tyr Gly Pro Gly Gln Gln Leu
            20
```

(2) INFORMATION FOR SEQ ID NO:47:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

GATCTCCCGG GCCATCTGGT CCGGGTAGCG CTGCGGCTGC TGCTGCTGCG GCAGGTCCAG    60

GCGGCTACGT AG    72

(2) INFORMATION FOR SEQ ID NO:48:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

GATCCTACGT AGCCGCCTGG ACCTGCCGCA GCAGCAGCAG CCGCAGCGCT ACCCGGACCA    60

GATGGCCCGG GA    72

(2) INFORMATION FOR SEQ ID NO:49:

(i) SEQUENCE CHARACTERISTICS:
        (A) LENGTH: 23 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:49:

Ser Pro Gly Pro Ser Gly Pro Gly Ser Ala Ala Ala Ala Ala Ala Ala
1               5                    10                 15

Ala Gly Pro Gly Gly Tyr Val
        20

(2) INFORMATION FOR SEQ ID NO:50:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

GATCTCCCGG GCCGGGCCAA CAAGGTCCGG GCGGCTATGG TCCAGGTCAA CAGCTGG    57

(2) INFORMATION FOR SEQ ID NO:51:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

GATCCCAGCT GTTGACCTGG ACCATAGCCG CCCGGACCTT GTTGGCCCGG CCCGGGA    57

(2) INFORMATION FOR SEQ ID NO:52:

(i) SEQUENCE CHARACTERISTICS:
        (A) LENGTH: 18 amino acids
        (B) TYPE: amino acid (C) STRANDEDNESS: unknown
            (D) TOPOLOGY: unknown (ii) MOLECULE TYPE: peptide (xi) SEQUENCE DESCRIPTION: SEQ ID NO:52:

Ser Pro Gly Pro Gly Gln Gln Gly Pro Gly Gly Tyr Gly Pro Gly Gln
1               5                  10                  15

Gln Leu (2) INFORMATION FOR SEQ ID NO:53:

(i) SEQUENCE CHARACTERISTICS:
            (A) LENGTH: 75 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:53:

GATCTCCCGG GCCGAGCGGT CCAGGTTCCG CAGCAGCAGC GGCTGCGGCG GCAGCGGGTC        60

CAGGTGGTTA CGTAG                                                         75

(2) INFORMATION FOR SEQ ID NO:54:

(i) SEQUENCE CHARACTERISTICS:
            (A) LENGTH: 75 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:54:

GATCCTACGT AACCACCTGG ACCCGCTGCC GCCGCAGCCG CTGCTGCTGC GGAACCTGGA        60

CCGCTCGGCC CGGGA                                                         75

(2) INFORMATION FOR SEQ ID NO:55:

(i) SEQUENCE CHARACTERISTICS:
            (A) LENGTH: 24 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:55:

Ser Pro Gly Pro Ser Gly Pro Gly Ser Ala Ala Ala Ala Ala Ala Ala
1               5                  10                  15

Ala Ala Gly Pro Gly Gly Tyr Val
                20

(2) INFORMATION FOR SEQ ID NO:56:

(i) SEQUENCE CHARACTERISTICS:
            (A) LENGTH: 87 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:56:

GATCTCCCGG GCCAGGCCAG CAGGGTCCGG GTGGCTATGG CCCAGGCCAG CAAGGTCCGG        60

```
GTGGTTACGG TCCAGGTCAG CAGCTGG                                                    87

(2) INFORMATION FOR SEQ ID NO:57:

(i) SEQUENCE CHARACTERISTICS:
        (A) LENGTH:  87 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:57:

GATCCCAGCT GCTGACCTGG ACCGTAACCA CCCGGACCTT GCTGGCCTGG GCCATAGCCA      60

CCCGGACCCT GCTGGCCTGG CCCGGGA                                         87

(2) INFORMATION FOR SEQ ID NO:58:

(i) SEQUENCE CHARACTERISTICS:
        (A) LENGTH:  28 amino acids
        (B) TYPE:  amino acid
        (C) STRANDEDNESS:  unknown
        (D) TOPOLOGY:  unknown (ii) MOLECULE TYPE:  peptide (xi) SEQUENCE DESCRIPTION:  SEQ ID NO:58:

Ser Pro Gly Pro Gly Gln Gln Gly Pro Gly Gly Tyr Gly Pro Gly Gln
  1               5                  10                  15

Gln Gly Pro Gly Gly Tyr Gly Pro Gly Gln Gln Leu
                 20                  25

(2) INFORMATION FOR SEQ ID NO:59:

(i) SEQUENCE CHARACTERISTICS:
        (A) LENGTH:  493 amino acids
        (B) TYPE:  amino acid
        (C) STRANDEDNESS:  unknown
        (D) TOPOLOGY:  unknown (ii) MOLECULE TYPE:  protein (xi) SEQUENCE DESCRIPTION:  SEQ ID NO:59:

Gly Pro Gly Gly Tyr Gly Pro Gly Gln Gln Gly Pro Gly Gly Tyr Gly
  1               5                  10                  15

Pro Gly Gln Gln Gly Pro Gly Arg Tyr Gly Pro Gly Gln Gln Gly Pro
                 20                  25                  30

Ser Gly Pro Gly Ser Ala Ala Ala Ala Ala Gly Ser Gly Gln Gln
             35                  40                  45

Gly Pro Gly Gly Tyr Gly Pro Arg Gln Gln Gly Pro Gly Gly Tyr Gly
             50                  55                  60

Gln Gly Gln Gln Gly Pro Ser Gly Pro Gly Ser Ala Ala Ala Ala Ser
 65                  70                  75                  80

Ala Ala Ala Ser Ala Glu Ser Gly Gly Pro Gly Gly Tyr Gly Pro Gly
                 85                  90                  95

Gln Gln Gly Pro Gly Gly Tyr Gly Pro Gly Gln Gln Gly Pro Gly Gly
                100                 105                 110

Tyr Gly Pro Gly Gln Gln Gly Pro Ser Gly Pro Gly Ser Ala Ala Ala
                115                 120                 125

Ala Ala Ala Ala Ala Ser Gly Pro Gly Gln Gln Gly Pro Gly Gly Tyr
            130                 135                 140
```

```
Gly Pro Gly Gln Gln Gly Pro Gly Tyr Gly Pro Gly Gln Gln Gly
145                 150                 155                 160

Pro Ser Gly Pro Gly Ser Ala Ala Ala Ala Ala Ala Ala Ser Gly
            165                 170                 175

Pro Gly Gln Gln Gly Pro Gly Gly Tyr Gly Pro Gly Gln Gln Gly Pro
        180                 185                 190

Gly Gly Tyr Gly Pro Gly Gln Gln Gly Thr Ser Gly Pro Gly Ser Ala
        195                 200                 205

Ala Ala Ala Ala Ala Ala Gly Pro Gly Gln Gln Gly Pro Gly Gly Tyr
210                 215                 220

Gly Pro Gly Gln Gln Gly Pro Ser Gly Pro Gly Ser Ala Ala Ala
225                 230                 235                 240

Ala Ala Ala Ala Gly Pro Gly Gly Tyr Gly Pro Gly Gln Gln Gly
                245                 250                 255

Pro Gly Gly Tyr Gly Pro Gly Gln Gln Gly Pro Ser Gly Pro Gly Ser
            260                 265                 270

Ala Ala Ala Ala Ala Ala Gly Pro Gly Gln Gln Gly Leu Gly Gly
                275                 280                 285

Tyr Gly Pro Gly Gln Gln Gly Pro Gly Gly Tyr Gly Pro Gly Gln Gln
290                 295                 300

Gly Pro Gly Gly Tyr Gly Pro Gly Ser Ala Ser Ala Ala Ala Ala
305                 310                 315                 320

Ala Gly Pro Gly Gln Gln Gly Pro Gly Gly Tyr Gly Pro Gly Gln Gln
            325                 330                 335

Gly Pro Ser Gly Pro Gly Ser Ala Ser Ala Ala Ala Ala Ala Ala
            340                 345                 350

Ala Gly Pro Gly Gly Tyr Gly Pro Gly Gln Gln Gly Pro Gly Gly Tyr
            355                 360                 365

Ala Pro Gly Gln Gln Gly Pro Ser Gly Pro Gly Ser Ala Ser Ala Ala
            370                 375                 380

Ala Ala Ala Ala Ala Ala Gly Pro Gly Gly Tyr Gly Pro Gly Gln Gln
385                 390                 395                 400

Gly Pro Gly Gly Tyr Ala Pro Gly Gln Gln Gly Pro Ser Gly Pro Gly
            405                 410                 415

Ser Ala Ala Ala Ala Ala Ala Ser Ala Gly Pro Gly Gly Tyr Gly
            420                 425                 430

Pro Ala Gln Gln Gly Pro Ser Gly Pro Gly Ile Ala Ala Ser Ala Ala
            435                 440                 445

Ser Ala Gly Pro Gly Gly Tyr Gly Pro Ala Gln Gln Gly Pro Ala Gly
450                 455                 460

Tyr Gly Pro Gly Ser Ala Val Ala Ala Ser Ala Gly Ala Gly Ser Ala
465                 470                 475                 480

Gly Tyr Gly Pro Gly Ser Gln Ala Ser Ala Ala Ala Ser
            485                 490

(2) INFORMATION FOR SEQ ID NO:60:

(i) SEQUENCE CHARACTERISTICS:
        (A) LENGTH:   119 amino acids
        (B) TYPE:  amino acid
        (C) STRANDEDNESS:  unknown
        (D) TOPOLOGY:  unknown (ii) MOLECULE TYPE:  peptide (xi) SEQUENCE DESCRIPTION: SEQ ID NO:60:
Gly Pro Ser Gly Pro Gly Ser Ala Ala Ala Ala Ala Ala Gly Pro Gly
```

```
1               5                    10                   15
Gln Gln Gly Pro Gly Gly Tyr Gly Pro Gly Gln Gln Gly Pro Gly Gly
                20                   25                   30

Tyr Gly Pro Gly Gln Gln Gly Pro Ser Gly Pro Gly Ser Ala Ala Ala
            35                   40                  45

Ala Ala Ala Ala Ala Gly Pro Gly Gly Tyr Gly Pro Gly Gln Gln Gly
        50                  55                   60

Pro Gly Gly Tyr Gly Pro Gly Gln Gln Gly Pro Ser Gly Pro Gly Ser
65                  70                   75                   80

Ala Ala Ala Ala Ala Ala Ala Ala Gly Pro Gly Gly Tyr Gly Pro
                85                   90                   95

Gly Gln Gln Gly Pro Gly Gly Tyr Gly Pro Gly Gln Gln Gly Pro Gly
100                 105                  110

Gly Tyr Gly Pro Gly Gln Gln
                115
```

(2) INFORMATION FOR SEQ ID NO:61:

(i) SEQUENCE CHARACTERISTICS:
        (A) LENGTH: 714 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:61:

```
Gly Pro Ser Gly Pro Gly Ser Ala Ala Ala Ala Ala Ala Gly Pro Gly
1               5                    10                   15

Gln Gln Gly Pro Gly Gly Tyr Gly Pro Gly Gln Gln Gly Pro Gly Gly
                20                   25                   30

Tyr Gly Pro Gly Gln Gln Gly Pro Ser Gly Pro Gly Ser Ala Ala Ala
            35                   40                  45

Ala Ala Ala Ala Ala Gly Pro Gly Gly Tyr Gly Pro Gly Gln Gln Gly
        50                  55                   60

Pro Gly Gly Tyr Gly Pro Gly Gln Gln Gly Pro Ser Gly Pro Gly Ser
65                  70                   75                   80

Ala Ala Ala Ala Ala Ala Ala Ala Gly Pro Gly Gly Tyr Gly Pro
                85                   90                   95

Gly Gln Gln Gly Pro Gly Gly Tyr Gly Pro Gly Gln Gln Gly Pro Gly
                100                  105                  110

Gly Tyr Gly Pro Gly Gln Gln Gly Pro Ser Gly Pro Gly Ser Ala Ala
            115                  120                 125

Ala Ala Ala Ala Gly Pro Gly Gln Gln Gly Pro Gly Gly Tyr Gly Pro
        130                 135                  140

Gly Gln Gln Gly Pro Gly Gly Tyr Gly Pro Gly Gln Gln Gly Pro Ser
145                 150                  155                 160

Gly Pro Gly Ser Ala Ala Ala Ala Ala Ala Ala Gly Pro Gly Gly
            165                  170                  175

Tyr Gly Pro Gly Gln Gln Gly Pro Gly Gly Tyr Gly Pro Gly Gln Gln
            180                  185                  190

Gly Pro Ser Gly Pro Gly Ser Ala Ala Ala Ala Ala Ala Ala Ala
            195                 200                  205

Gly Pro Gly Gly Tyr Gly Pro Gly Gln Gln Gly Pro Gly Gly Tyr Gly
    210                  215                  220

Pro Gly Gln Gln Gly Pro Gly Gly Tyr Gly Pro Gly Gln Gln Gly Pro
```

```
                225                 230                 235                 240
    Ser Gly Pro Gly Ser Ala Ala Ala Ala Ala Gly Pro Gly Gln Gln
                    245                 250                 255
    Gly Pro Gly Gly Tyr Gly Pro Gly Gln Gln Gly Pro Gly Gly Tyr Gly
                        260                 265                 270
    Pro Gly Gln Gln Gly Pro Ser Gly Pro Gly Ser Ala Ala Ala Ala
                275                 280                 285
    Ala Ala Ala Gly Pro Gly Gly Tyr Gly Pro Gly Gln Gln Gly Pro Gly
            290                 295                 300
    Gly Tyr Gly Pro Gly Gln Gln Gly Pro Ser Gly Pro Gly Ser Ala Ala
    305                 310                 315                 320
    Ala Ala Ala Ala Ala Ala Gly Pro Gly Gly Tyr Gly Pro Gly Gln
                    325                 330                 335
    Gln Gly Pro Gly Gly Tyr Gly Pro Gly Gln Gln Gly Pro Gly Gly Tyr
                        340                 345                 350
    Gly Pro Gly Gln Gln Gly Pro Ser Gly Pro Gly Ser Ala Ala Ala Ala
                355                 360                 365
    Ala Ala Gly Pro Gly Gln Gln Gly Pro Gly Gly Tyr Gly Pro Gly Gln
            370                 375                 380
    Gln Gly Pro Gly Gly Tyr Gly Pro Gly Gln Gln Gly Pro Ser Gly Pro
    385                 390                 395                 400
    Gly Ser Ala Ala Ala Ala Ala Ala Ala Gly Pro Gly Gly Tyr Gly
                    405                 410                 415
    Pro Gly Gln Gln Gly Pro Gly Gly Tyr Gly Pro Gly Gln Gln Gly Pro
                        420                 425                 430
    Ser Gly Pro Gly Ser Ala Ala Ala Ala Ala Ala Ala Ala Gly Pro
                435                 440                 445
    Gly Gly Tyr Gly Pro Gly Gln Gln Gly Pro Gly Gly Tyr Gly Pro Gly
            450                 455                 460
    Gln Gln Gly Pro Gly Gly Tyr Gly Pro Gly Gln Gln Gly Pro Ser Gly
    465                 470                 475                 480
    Pro Gly Ser Ala Ala Ala Ala Ala Ala Gly Pro Gly Gln Gln Gly Pro
                    485                 490                 495
    Gly Gly Tyr Gly Pro Gly Gln Gln Gly Pro Gly Gly Tyr Gly Pro Gly
                        500                 505                 510
    Gln Gln Gly Pro Ser Gly Pro Gly Ser Ala Ala Ala Ala Ala Ala
                515                 520                 525
    Ala Gly Pro Gly Gly Tyr Gly Pro Gly Gln Gln Gly Pro Gly Gly Tyr
            530                 535                 540
    Gly Pro Gly Gln Gln Gly Pro Ser Gly Pro Gly Ser Ala Ala Ala Ala
    545                 550                 555                 560
    Ala Ala Ala Ala Gly Pro Gly Gly Tyr Gly Pro Gly Gln Gln Gly
                    565                 570                 575
    Pro Gly Gly Tyr Gly Pro Gly Gln Gln Gly Pro Gly Gly Tyr Gly Pro
                        580                 585                 590
    Gly Gln Gln Gly Pro Ser Gly Pro Gly Ser Ala Ala Ala Ala Ala Ala
                595                 600                 605
    Gly Pro Gly Gln Gln Gly Pro Gly Gly Tyr Gly Pro Gly Gln Gln Gly
            610                 615                 620
    Pro Gly Gly Tyr Gly Pro Gly Gln Gln Gly Pro Ser Gly Pro Gly Ser
    625                 630                 635                 640
    Ala Ala Ala Ala Ala Ala Ala Gly Pro Gly Gly Tyr Gly Pro Gly
                    645                 650                 655
```

-continued

```
Gln Gln Gly Pro Gly Gly Tyr Gly Pro Gly Gln Gly Pro Ser Gly
            660                 665                 670

Pro Gly Ser Ala Ala Ala Ala Ala Ala Ala Gly Pro Gly Gly
            675                 680                 685

Tyr Gly Pro Gly Gln Gln Gly Pro Gly Gly Tyr Gly Pro Gly Gln Gln
            690                 695                 700

Gly Pro Gly Gly Tyr Gly Pro Gly Gln Gln
705                 710
```

(2) INFORMATION FOR SEQ ID NO:62:

(i) SEQUENCE CHARACTERISTICS:
        (A) LENGTH:  101 amino acids
        (B) TYPE:  amino acid
        (C) STRANDEDNESS:  unknown
        (D) TOPOLOGY:  unknown (ii) MOLECULE TYPE:  peptide (xi) SEQUENCE DESCRIPTION: SEQ ID NO:62:

```
Ser Gln Gly Ala Gly Gln Gly Gly Tyr Gly Gly Leu Gly Ser Gln Gly
1               5                   10                  15

Ala Gly Arg Gly Gly Leu Gly Gly Gln Gly Ala Gly Ala Ala Ala
            20                  25                  30

Ala Ala Ala Gly Gly Ala Gly Gln Gly Gly Leu Gly Ser Gln Gly Ala
            35                  40                  45

Gly Gln Gly Ala Gly Ala Ala Ala Ala Ala Gly Gly Ala Gly Gln
        50                  55                  60

Gly Gly Tyr Gly Gly Leu Gly Ser Gln Gly Ala Gly Arg Gly Gly Gln
65                  70                  75                  80

Gly Ala Gly Ala Ala Ala Ala Ala Gly Gly Ala Gly Gln Gly Gly
            85                  90                  95

Tyr Gly Gly Leu Gly
            100
```

(2) INFORMATION FOR SEQ ID NO:63:

(i) SEQUENCE CHARACTERISTICS:
        (A) LENGTH:  604 amino acids
        (B) TYPE:  amino acid
        (C) STRANDEDNESS:  unknown
        (D) TOPOLOGY:  unknown (ii) MOLECULE TYPE:  protein (xi) SEQUENCE DESCRIPTION: SEQ ID NO:63:

```
Ser Gln Gly Ala Gly Gln Gly Gly Tyr Gly Gly Leu Gly Ser Gln Gly
1               5                   10                  15

Ala Gly Arg Gly Gly Leu Gly Gly Gln Gly Ala Gly Ala Ala Ala
            20                  25                  30

Ala Ala Ala Gly Gly Ala Gly Gln Gly Gly Leu Gly Ser Gln Gly Ala
            35                  40                  45

Gly Gln Gly Ala Gly Ala Ala Ala Ala Ala Gly Gly Ala Gly Gln
        50                  55                  60

Gly Gly Tyr Gly Gly Leu Gly Ser Gln Gly Ala Gly Arg Gly Gly Gln
65                  70                  75                  80

Gly Ala Gly Ala Ala Ala Ala Ala Gly Gly Ala Gly Gln Gly Gly
            85                  90                  95

Tyr Gly Gly Leu Gly Ser Gln Gly Ala Gly Gln Gly Gly Tyr Gly Gly
```

-continued

```
                100                 105                 110
Leu Gly Ser Gln Gly Ala Gly Arg Gly Gly Leu Gly Gly Gln Gly Ala
            115                 120                 125
Gly Ala Ala Ala Ala Ala Ala Gly Gly Ala Gly Gln Gly Gly Leu
130                 135                 140
Gly Ser Gln Gly Ala Gly Gln Gly Ala Gly Ala Ala Ala Ala Ala
145                 150                 155                 160
Gly Gly Ala Gly Gln Gly Gly Tyr Gly Gly Leu Gly Ser Gln Gly Ala
            165                 170                 175
Gly Arg Gly Gly Gln Gly Ala Gly Ala Ala Ala Ala Ala Gly Gly
            180                 185                 190
Ala Gly Gln Gly Gly Tyr Gly Gly Leu Gly Ser Gln Gly Ala Gly Gln
            195                 200                 205
Gly Gly Tyr Gly Gly Leu Gly Ser Gln Gly Ala Gly Arg Gly Gly Leu
    210                 215                 220
Gly Gly Gln Gly Ala Gly Ala Ala Ala Ala Ala Ala Gly Gly Ala
225                 230                 235                 240
Gly Gln Gly Gly Leu Gly Ser Gln Gly Ala Gly Gln Gly Ala Gly Ala
            245                 250                 255
Ala Ala Ala Ala Gly Gly Ala Gly Gln Gly Gly Tyr Gly Gly Leu
            260                 265                 270
Gly Ser Gln Gly Ala Gly Arg Gly Gly Gln Gly Ala Gly Ala Ala Ala
            275                 280                 285
Ala Ala Ala Gly Gly Ala Gly Gly Tyr Gly Gly Leu Gly Ser Gly
            290                 295                 300
Ala Gly Gln Gly Gly Tyr Gly Gly Leu Gly Ser Gln Gly Ala Gly Arg
305                 310                 315                 320
Gly Gly Leu Gly Gly Gln Gly Ala Gly Ala Ala Ala Ala Ala Ala
            325                 330                 335
Gly Gly Ala Gly Gln Gly Gly Leu Gly Ser Gln Gly Ala Gly Gln Gly
            340                 345                 350
Ala Gly Ala Ala Ala Ala Ala Gly Gly Ala Gly Gln Gly Gly Tyr
            355                 360                 365
Gly Gly Leu Gly Ser Gln Gly Ala Gly Arg Gly Gly Gln Gly Ala Gly
    370                 375                 380
Ala Ala Ala Ala Ala Gly Gly Ala Gly Gln Gly Gly Tyr Gly Gly
385                 390                 395                 400
Leu Gly Ser Gln Gly Ala Gly Gln Gly Gly Tyr Gly Gly Leu Gly Ser
            405                 410                 415
Gln Gly Ala Gly Arg Gly Gly Leu Gly Gly Gln Gly Ala Gly Ala Ala
            420                 425                 430
Ala Ala Ala Ala Gly Gly Ala Gly Gln Gly Gly Leu Gly Ser Gln
            435                 440                 445
Gly Ala Gly Gln Gly Ala Gly Ala Ala Ala Ala Ala Gly Gly Ala
    450                 455                 460
Gly Gln Gly Gly Tyr Gly Gly Leu Gly Ser Gln Gly Ala Gly Arg Gly
465                 470                 475                 480
Gly Gln Gly Ala Gly Ala Ala Ala Ala Ala Gly Gly Ala Gly Gln
            485                 490                 495
Gly Gly Tyr Gly Gly Leu Gly Ser Gln Gly Ala Gly Gln Gly Gly Tyr
            500                 505                 510
Gly Gly Leu Gly Ser Gln Gly Ala Gly Arg Gly Gly Leu Gly Gly Gln
    515                 520                 525
```

```
Gly Ala Gly Ala Ala Ala Ala Ala Gly Ala Gly Gln Gly
    530             535             540

Gly Leu Gly Ser Gln Gly Ala Gln Gly Ala Gly Ala Ala Ala Ala
545             550             555             560

Ala Ala Gly Gly Ala Gly Gln Gly Gly Tyr Gly Gly Leu Gly Ser Gln
            565             570             575

Gly Ala Gly Arg Gly Gly Gln Gly Ala Gly Ala Ala Ala Ala Ala
            580             585             590

Gly Gly Ala Gly Gln Gly Gly Tyr Gly Gly Leu Gly
            595             600
```

(2) INFORMATION FOR SEQ ID NO:64:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:64:

GATCTCAGGG TGCTGGCCAG GGTGGCTATG GTGGCCTGG           39

(2) INFORMATION FOR SEQ ID NO:65:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

GATCCCAGGC CACCATAGCC ACCCTGGCCA GCACCCTGA           39

(2) INFORMATION FOR SEQ ID NO:66:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:66:

```
Ser Gln Gly Ala Gly Gln Gly Gly Tyr Gly Gly Leu Gly
1               5                   10
```

(2) INFORMATION FOR SEQ ID NO:67:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

GATCTCAAGG CGCTGGTCGC GGTGGCCTGG GTGCCAGGG TGCAGGTGCT GCTGCTGCTG    60
CGGCTGCTGG TGGTGCAGGT CAGGGTGGTC TGG                                93

(2) INFORMATION FOR SEQ ID NO:68:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:68:

```
GATCCCAGAC CACCCTGACC TGCACCACCA GCAGCCGCAG CAGCAGCAGC ACCTGCACCC      60

TGGCCACCCA GGCCACCGCG ACCAGCGCCT TGA                                  93
```

(2) INFORMATION FOR SEQ ID NO:69:

(i) SEQUENCE CHARACTERISTICS:
        (A) LENGTH: 31 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:69:

```
Ser Gln Gly Ala Gly Arg Gly Gly Leu Gly Gly Gln Gly Ala Gly Ala
 1               5                  10                  15

Ala Ala Ala Ala Ala Ala Gly Gly Ala Gly Gln Gly Gly Leu Gly
            20                  25                  30
```

(2) INFORMATION FOR SEQ ID NO:70:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:70:

```
GATCTCAGGG CGCAGGTCAA GGTGCTGGTG CAGCTGCGGC GGCAGCTGGT GGCGCGGGTC      60

AAGGTGGCTA CGGCGGTTTA G                                               81
```

(2) INFORMATION FOR SEQ ID NO:71:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:71:

```
GATCCTAAAC CGCCGTAGCC ACCTTGACCC GCGCCACCAG CTGCCGCCGC AGCTGCACCA      60

GCACCTTGAC CTGCGCCCTG A                                               81
```

(2) INFORMATION FOR SEQ ID NO:72:

(i) SEQUENCE CHARACTERISTICS:
        (A) LENGTH: 28 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:72:

Ser Gln Gly Ala Gly Gln Gly Ala Gly Ala Ala Ala Ala Ala Gly
1               5                   10                  15

Gly Gly Ala Gly Gln Gly Gly Tyr Gly Gly Leu Gly
            20                  25

(2) INFORMATION FOR SEQ ID NO:73:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:73:

```
GATCTCAAGG TGCGGGTCGC GGTGGTCAGG GCGCTGGTGC AGCAGCGGCA GCAGCAGGTG    60

GCGCTGGCCA AGGTGGTTAC GGTGGTCTTG                                    90
```

(2) INFORMATION FOR SEQ ID NO:74:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:74:

```
GATCCAAGAC CACCGTAACC ACCTTGGCCA GCGCCACCTG CTGCTGCCGC TGCTGCACCA    60

GCGCCCTGAC CACCGCGACC CGCACCTTGA                                    90
```

(2) INFORMATION FOR SEQ ID NO:75:

(i) SEQUENCE CHARACTERISTICS:
        (A) LENGTH: 30 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:75:

Ser Gln Gly Ala Gly Arg Gly Gly Gln Gly Ala Gly Ala Ala Ala
1               5                   10                  15

Ala Ala Gly Gly Ala Gly Gln Gly Gly Tyr Gly Gly Leu Gly
            20                  25                  30

(2) INFORMATION FOR SEQ ID NO:76:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:76:

```
AATTCAGATC TAAGCTTG                                                 18
```

(2) INFORMATION FOR SEQ ID NO:77:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:77:

```
GATCCAAGCT TAGATCTG                                                   18
```

(2) INFORMATION FOR SEQ ID NO:78:

(i) SEQUENCE CHARACTERISTICS:
        (A) LENGTH: 4909 base pairs
        (B) TYPE: nucleic acid
        (C) STRANDEDNESS: single
        (D) TOPOLOGY: circular (ii) MOLECULE TYPE: DNA (genomic)

(xi) SEQUENCE DESCRIPTION: SEQ ID NO:78:

```
GAATTCCGGG GGATTATGCG TTAAGCATAA AGTGTAAAGC CTGGGGTGCC TAATGAGTGA      60
GCTAACTCAC ATTAATTGCG TTGCGCTCAC TGCCCGCTTT CCAGTCGGGA AACCTGTCGT     120
GCCAGCTGCA TTAATGAATC GGCCAACGCG CGGGGAGAGG CGGTTTGCGT ATTGGGCGCC     180
AGGGTGGTTT TCTTTTCAC CAGTGAGACG GGCAACAGCT GATTGCCCTT CACCGCCTGG      240
CCCTGAGAGA GTTGCAGCAA GCGGTCCACG CTGGTTTGCC CCAGCAGGCG AAAATCCTGT     300
TTGATGGTGG TTGACGGCGG GATATAACAT GAGCTGTCTT CGGTATCGTC GTATCCCACT     360
ACCGAGATAT CCGCACCAAC GCGCAGCCCG GACTCGGTAA TGGCGCGCAT TGCGCCCAGC     420
GCCATCTGAT CGTTGGCAAC CAGCATCGCA GTGGGAACGA TGCCCTCATT CAGCATTTGC     480
ATGGTTTGTT GAAAACCGGA CATGGCACTC CAGTCGCCTT CCCGTTCCGC TATCGGCTGA     540
ATTTGATTGC GAGTGAGATA TTTATGCCAG CCAGCCAGAC GCAGACGCGC CGAGACAGAA     600
CTTAATGGGC CCGCTAACAG CGCGATTTGC TGGTGACCCA ATGCGACCAG ATGCTCCACG     660
CCCAGTCGCG TACCGTCTTC ATGGGAGAAA ATAATACTGT TGATGGGTGT CTGGTCAGAG     720
ACATCAAGAA ATAACGCCGG AACATTAGTG CAGGCAGCTT CCACAGCAAT GGCATCCTGG     780
TCATCCAGCG GATAGTTAAT GATCAGCCCA CTGACGCGTT GCGCGAGAAG ATTGTGCACC     840
GCCGCTTTAC AGGCTTCGAC GCCGCTTCGT TCTACCATCG ACACCACCAC GCTGGCACCC     900
AGTTGATCGG CGCGAGATTT AATCGCCGCG ACAATTTGCG ACGGCGCGTG CAGGGCCAGA     960
CTGGAGGTGG CAACGCCAAT CAGCAACGAC TGTTTGCCCG CCAGTTGTTG TGCCACGCGG    1020
TTGGGAATGT AATTCAGCTC CGCCATCGCC GCTTCCACTT TTTCCCGCGT TTTCGCAGAA    1080
ACGTGGCTGG CCTGGTTCAC CACGCGGGAA ACGGTCTGAT AAGAGACACC GGCATACTCT    1140
GCGACATCGT ATAACGTTAC TGGTTTCACA TTCACCACCC TGAATTGACT CTCTTCCGGG    1200
CGCTATCATG CCATACCGCG AAAGGTTTTG CGCCATTCGA TGGTGTCAAC CTTGCAGAGC    1260
TGCGCCTTTA TTATTATCCG CCGGGAGAAA ATATTCCGTG GATCTAACGG GATGCGTTAT    1320
GTTGAAGTGA GACCGGTCGA CGCATGCCAG GACAACTTCT GGTCCGGTAA CGTGCTGAGC    1380
CCGGCCAAGC TTACTCCCCA TCCCCCTGTT GACAATTAAT CATCGGCTCG TATAATGTGT    1440
GGAATTGTGA GCGGATAACA ATTTCACACA GGAAACAGGA TCACTAAGGA GGTTTAAATA    1500
TGGCTACTGT TATAGATCCG TCTGTCGCGA CGGCCGTTTC GTCGAATGGC TCGGTTGCCA    1560
```

-continued

```
ATATCAATGC GATCAAGTCG GGCGCTCTGG AGTCCGGCTT TACGCAGTCA GACGTTGCCT    1620

ATTGGGCCTA TAACGGCACC GGCCTTTATG ATGGCAAGGG CAAGGTGGAA GATTTGCGCC    1680

TTCTGGCGAC GCTTTACCCG GAAACGATCC ATATCGTTGC GCGTAAGGAT GCAAACATCA    1740

AATCGGTCGC AGACCTGAAA GGCAAGCGCG TTTCGCTGGA TGAGCCGGGT TCTGGCACCA    1800

TCGTCGATGC GCGTATCGTT CTTGAAGCCT ACGGCCTCAC GGAAGACGAT ATCAAGGCTG    1860

AACACCTGAA GCCGGGACCG GCAGGCGAGA GGCTGAAAGA TGGTGCGCTG GACGCCTATT    1920

TCTTTGTGGG CGGCTATCCG ACGGGCGCAA TCTCGGAACT GGCCATCTCG AACGGTATTT    1980

CGCTCGTTCC GATCTCCGGG CCGGAAGCGG ACAAGATTCT GGAGAAATAT TCCTTCTTCT    2040

CGAAGGATGT GGTTCCTGCC GGAGCCTATA AGGACGTGGC GGAAACACCG ACCCTTGCCG    2100

TTGCCGCACA GTGGGTGACG AGCGCCAAGC AGCCGGACGA CCTCATCTAT AACATCACCA    2160

AGGCTGGTTC TCCGAAACCG GGTGCTGGTA GATCTAAGCT TCCCGGGGAT CCTAGCTAGC    2220

TAGCCATGGC ATCACAGTAT CGTGATGACA GAGGCAGGGA GTGGACAAA ATTGAAATCA     2280

AATAATGATT TTATTTTGAC TGATAGTGAC CTGTTCGTTG CAACAAATTG ATAAGCAATG    2340

CTTTTTTATA ATGCCAACTT AGTATAAAAA AGCTGAACGA GAAACGTAAA ATGATATAAA    2400

TATCAATATA TTAAATTAGA TTTTGCATAA AAAACAGACT ACATAATACT GTAAAACACA    2460

ACATATGCAG TCACTATGAA TCAACTACTT AGATGGTATT AGTGACCTGT AACAGAGCAT    2520

TAGCGCAAGG TGATTTTTGT CTTCTTGCGC TAATTTTTTG TCATCAAACC TGTCGCACTC    2580

CAGAGAAGCA CAAAGCCTCG CAATCCAGTG CAAAGCTCTG CCTCGCGCGT TTCGGTGATG    2640

ACGGTGAAAA CCTCTGACAC ATGCAGCTCC CGGAGACGGT CACAGCTTGT CTGTAAGCGG    2700

ATGCCGGGAG CAGACAAGCC CGTCAGGGCG CGTCAGCGGG TGTTGGCGGG TGTCGGGGCG    2760

CAGCCATGAC CCAGTCACGT AGCGATAGCG GAGTGTATAC TGGCTTAACT ATGCGGCATC    2820

AGAGCAGATT GTACTGAGAG TGCACCATAT GCGGTGTGAA ATACCGCACA GATGCGTAAG    2880

GAGAAAATAC CGCATCAGGC GCTCTTCCGC TTCCTCGCTC ACTGACTCGC TGCGCTCGGT    2940

CGTTCGGCTG CGGCGAGCGG TATCAGCTCA CTCAAAGGCG GTAATACGGT TATCCACAGA    3000

ATCAGGGGAT AACGCAGGAA AGAACATGTG AGCAAAAGGC CAGCAAAAGG CCAGGAACCG    3060

TAAAAAGGCC GCGTTGCTGG CGTTTTTCCA TAGGCTCCGC CCCCCTGACG AGCATCACAA    3120

AAATCGACGC TCAAGTCAGA GGTGGCGAAA CCCGACAGGA CTATAAAGAT ACCAGGCGTT    3180

TCCCCCTGGA AGCTCCCTCG TGCGCTCTCC TGTTCCGACC CTGCCGCTTA CCGGATACCT    3240

GTCCGCCTTT CTCCCTTCGG GAAGCGTGGC GCTTTCTCAT AGCTCACGCT GTAGGTATCT    3300

CAGTTCGGTG TAGGTCGTTC GCTCCAAGCT GGGCTGTGTG CACGAACCCC CCGTTCAGCC    3360

CGACCGCTGC GCCTTATCCG GTAACTATCG TCTTGAGTCC AACCCGGTAA GACACGACTT    3420

ATCGCCACTG GCAGCAGCCA CTGGTAACAG GATTAGCAGA GCGAGGTATG TAGGCGGTGC    3480

TACAGAGTTC TTGAAGTGGT GGCCTAACTA CGGCTACACT AGAAGGACAG TATTTGGTAT    3540

CTGCGCTCTG CTGAAGCCAG TTACCTTCGG AAAAAGAGTT GGTAGCTCTT GATCCGGCAA    3600

ACAAACCACC GCTGGTAGCG GTGGTTTTTT TGTTTGCAAG CAGCAGATTA CGCGCAGAAA    3660

AAAAGGATCT CAAGAAGATC CTTTGATCTT TTCTACGGGG TCTGACGCTC AGTGGAACGA    3720

AAACTCACGT TAAGGGATTT TGGTCATGAG ATTATCAAAA AGGATCTTCA CCTAGATCCT    3780

TTTAAATTAA AAATGAAGTT TTAAATCAAT CTAAAGTATA TATGAGTAAA CTTGGTCTGA    3840

CAGTTACCAA TGCTTAATCA GTGAGGCACC TATCTCAGCG ATCTGTCTAT TTCGTTCATC    3900

CATAGTTGCC TGACTCCCCG TCGTGTAGAT AACTACGATA CGGGAGGGCT TACCATCTGG    3960
```

-continued

```
CCCCAGTGCT GCAATGATAC CGCGAGACCC ACGCTCACCG GCTCCAGATT TATCAGCAAT      4020

AAACCAGCCA GCCGGAAGGG CCGAGCGCAG AAGTGGTCCT GCAACTTTAT CCGCCTCCAT      4080

CCAGTCTATT AATTGTTGCC GGGAAGCTAG AGTAAGTAGT TCGCCAGTTA ATAGTTTGCG      4140

CAACGTTGTT GCCATTGCTG CAGGCATCGT GGTGTCACGC TCGTCGTTTG GTATGGCTTC      4200

ATTCAGCTCC GGTTCCCAAC GATCAAGGCG AGTTACATGA TCCCCCATGT TGTGCAAAAA      4260

AGCGGTTAGC TCCTTCGGTC CTCCGATCGT TGTCAGAAGT AAGTTGGCCG CAGTGTTATC      4320

ACTCATGGTT ATGGCAGCAC TGCATAATTC TCTTACTGTC ATGCCATCCG TAAGATGCTT      4380

TTCTGTGACT GGTGAGTACT CAACCAAGTC ATTCTGAGAA TAGTGTATGC GGCGACCGAG      4440

TTGCTCTTGC CCGGCGTCAA CACGGGATAA TACCGCGCCA CATAGCAGAA CTTTAAAAGT      4500

GCTCATCATT GGAAAACGTT CTTCGGGGCG AAAACTCTCA AGGATCTTAC CGCTGTTGAG      4560

ATCCAGTTCG ATGTAACCCA CTCGTGCACC CAACTGATCT TCAGCATCTT TTACTTTCAC      4620

CAGCGTTTCT GGGTGAGCAA AAACAGGAAG GCAAAATGCC GCAAAAAAGG GAATAAGGGC      4680

GACACGGAAA TGTTGAATAC TCATACTCTT CCTTTTTCAA TATTATTGAA GCATTTATCA      4740

GGGTTATTGT CTCATGAGCG GATACATATT TGAATGTATT TAGAAAAATA AACAAATAGG      4800

GGTTCCGCGC ACATTTCCCC GAAAAGTGCC ACCTGACGTC TAAGAAACCA TTATTATCAT      4860

GACATTAACC TATAAAAATA GGCGTATCAC GAGGCCCTTT CGTCTTCAA                 4909
```

(2) INFORMATION FOR SEQ ID NO:79:

(i) SEQUENCE CHARACTERISTICS:
        (A) LENGTH: 9144 base pairs
        (B) TYPE: nucleic acid
        (C) STRANDEDNESS: single
        (D) TOPOLOGY: circular (ii) MOLECULE TYPE: DNA (genomic)

(xi) SEQUENCE DESCRIPTION: SEQ ID NO:79:

```
AATTCGAGCT CGGTACCCAT CGAATTCCTT CAGGAAAAGA ACGATGGCTG TCTTATTAGC        60

GGTTGCAGGC ACATTTATTT TGGTCACACA CGGGAATGTC GGCAGCCTGT CTATATCCGG       120

TCTGGCTGTT TTTTGGGGCA TCAGCTCGGC ATTTGCGCTG GCGTTTTACA CCCTCCAGCC       180

GCATCGGCTT TTGAAGAAAT GGGGCTCCGC CATTATTGTC GGATGGGCA TGCTGATGCG        240

GAGCCGTTCT CAGCCTGATT CAGCCGCCTT GGAAGTTTGA AGGCCAATGG TCGTTGTCCG       300

CATATGCCGC GATCGTGTTT ATCATCATTT TCGGAACGCT CATCGCTTTT TATTGCTATT       360

TGGAAAGCCT GAAATATCTG AGTGCCTCTG AAACCAGCCT CCTCGCCTGT GCAGAGCCGC       420

TGTCAGCAGC TTTTTTAGCG GTGATCTGGC TGCATGTTCC CTTCGGAATA TCAGAATGGC       480

TGGGTACTTT ACTGATTTTA GCCACCATCG CTTATTATCT ATCAAGAAAA AATAACCTCT       540

CTTTTTTTAG AGAGGTTTTT CCCTAGGCCT GAAGCACCCT TTAGTCTCAA TTACCCATAA       600

ATTAAAAGGC CTTTTTTCGT TTTACTATCA TTCAAAAGAG GAAAATAGAC CAGTTGTCAA       660

TAGAATCAGA GTCTAATAGA ATGAGGTCGA AAAGTAAATC ACGCAGGATT GTTACTGATA       720

AAGCAGGCAA GACCTAAAAT GTGTTAAGGG CAAAGTGTAT TCTTTGGCGT CATCCCTTAC       780

ATATTTGGG TCTTTTTTTC TGTAACAAAC CTGCCATCCA TGAATTCGGG AGGATCGAAA        840

CGGCAGATCG CAAAAACAGT ACATACAGAA GGAGACATGA ACATGAACAT CAAAAAAATT       900

GTAAAACAAG CCACAGTACT GACTTTTACG ACTGCACTGC TAGCAGGAGG AGCGACTCAA       960

GCCTTCGCGA AAGAAGATAT CGATCAACGC AATGGTTTTA TCCAAAGCCT TAAAGATGAT      1020
```

```
CCAAGCCAAA GTGCTAACGT TTTAGGTGAA GCTCAAAAAC TTAATGACTC TCAAGCTCCA    1080

AAAGCTGATG CGCAACAAAA TAACTTCAAC AAAGATCAAC AAAGCGCCTT CTATGAAATC    1140

TTGAACATGC CTAACTTAAA CGAAGCGCAA CGTAACGGCT TCATTCAAAG TCTTAAAGAC    1200

GACCCAAGCC AAAGCACTAA CGTTTTAGGT GAAGCTAAAA AATTAAACGA ATCTCAAGCA    1260

CCGAAAGCTG ATAACAATTT CAACAAAGAA CAACAAAATG CTTTCTATGA AATCTTGAAT    1320

ATGCCTAACT TAAACGAAGA ACAACGCAAT GGTTTCATCC AAAGCTTAAA AGATGACCCA    1380

AGCCAAAGTG CTAACCTATT GTCAGAAGCT AAAAAGTTAA ATGAATCTCA AGCACCGAAA    1440

GCGGATAACA AATTCAACAA AGAACAACAA AATGCTTTCT ATGAAATCTT ACATTTACCT    1500

AACTTAAACG AAGAACAACG CAATGGTTTC ATCCAAAGCC TAAAAGATGA CCCAAGCCAA    1560

AGCGCTAACC TTTTAGCAGA AGCTAAAAAG CTAAATGATG CTCAAGCACC AAAAGCTGAC    1620

AACAAATTCA ACAAAGAACA ACAAAATGCT TTCTATGAAA TTTTACATTT ACCTAACTTA    1680

ACTGAAGAAC AACGTAACGG CTTCATCCAA AGCCTTAAAG ACGATCCGGG GAATTCCCGG    1740

GGATCCGTCG ACCTGCAGGC ATGCAAGCTT ACTCCCCATC CCCTCCAGTA ATGACCTCAG    1800

AACTCCATCT GGATTTGTTC AGAACGCTCG GTTGCCGCCG GGCGTTTTTT ATTGGTGAGA    1860

ATCGCAGCAA CTTGTCGCGC CAATCGAGCC ATGTCGTCGT CAACGACCCC CCATTCAAGA    1920

ACAGCAAGCA GCATTGAGAA CTTTGGAATC CAGTCCCTCT TCCACCTGCT GAGGGCAATA    1980

AGGGCTGCAC GCGCACTTTT ATCCGCCTCT GCTGCGCTCC GCCACCGTAG TTAAATTTAT    2040

GGTTGGTTAT GAAATGCTGG CAGAGACCCA GCGAGACCTG ACCGCAGAAC AGGCAGCAGA    2100

GCGTTTGCGC GCAGTCAGCG ATACCCCGGT TGATAATCAG AAAAGCCCCA AAACAGGAA    2160

GATTGTATAA GCAAATATTT AAATTGTAAA CGTTAATATT TTGTTAAAAT TCGCGTTAAA    2220

TTTTTGTTAA ATCAGCTCAT TTTTTAACCA ATAGGCCGAA ATCGGCAAAA TCCCTTATAA    2280

ATCAAAAGAA TAGCCCGAGA TAGGGTTGAG TGTTGTTCCA GTTTGGAACA AGAGTCCACT    2340

ATTAAAGAAC GTGGACTCCA ACGTCAAAGG GCGAAAAACC GTCTATCAGG GCGATGGCCC    2400

ACTACGTGAA CCATCACCCA AATCAAGTTT TTTGGGGTCG AGGTGCCGTA AAGCACTAAA    2460

TCGGAACCCT AAAGGGAGCC CCCGATTTAG AGCTTGACGG GGAAAGCCGG CGAACGTGGC    2520

GAGAAAGGAA GGGAAGAAAG CGAAAGGAGC GGGCGCTAGG GCGCGAGCAA GTGTAGCGGT    2580

CACGCGCGCG TAACCACCAC ACCCGCCGCG CTTAATGCGC CGCTACAGGG CGCGTATCCA    2640

TTTTCGCGAA TCCGGAGTGT AAGAAATGAG TCTGAAAGAA AAAACACAAT CTCTGTTTGC    2700

CAACGCATTT GGCTACCCTG CCACTCACAC CATTCAGGTG CGTCATATAC TGACTGAAAA    2760

CGCCCGCACC GTTGAAGCTG CCAGCGCGCT GGAGCAAGGC GACCTGAAAC GTATGGGCGA    2820

GTTGATGGCG GAGTCTCATG CCTCTATGCG CGATGATTTC GAAATCACCG TGCCGCAAAT    2880

TGACACTCTG GTAGAAATCG TCAAAGCTGT GATTGGCGAC AAAGGTGGCG TACGCATGAC    2940

CGGCGGCGGA TTTGGCGGCT GTATCGTCGC GCGTATCCCG AAGAGCTGG TGCCTGCCGC    3000

ACAGCAAGCT GTCGCTGAAC AATATGAAGC AAAAACAGGT ATTAAAGAGA CTTTTTACGT    3060

TTGTAAACCA TCACAAGGAG CAGGACAGTG CTGAACGAAA CTCCCGCACT GGCACCCGAT    3120

GGCAGCCGTA CCGACTGTTC TGCCTCGCGC GTTTCGGTGA TGACGGTGAA AACCTCTGAC    3180

ACATGCAGCT CCCGGAGACG GTCACAGCTT GTCTGTAAGC GGATGCCGGG AGCAGACAAG    3240

CCCGTCAGGG CGCGTCAGCG GGTGTTGGCG GGTGTCGGGG CGCAGCCATG ACCCAGTCAC    3300

GTAGCGATAG CGGAGTGTAT ACTGGCTTAA CTATGCGGCA TCAGAGCAGA TTGTACTGAG    3360
```

-continued

```
AGTGCACCAT ATGCGGTGTG AAATACCGCA CAGATGCGTA AGGAGAAAAT ACCGCATCAG   3420

GCGCTCTTCC GCTTCCTCGC TCACTGACTC GCTGCGCTCG GTCGTTCGGC TGCGGCGAGC   3480

GGTATCAGCT CACTCAAAGG CGGTAATACG GTTATCCACA GAATCAGGGG ATAACGCAGG   3540

AAAGAACATG TGAGCAAAAG GCCAGCAAAA GGCCAGGAAC CGTAAAAAGG CCGCGTTGCT   3600

GGCGTTTTTC CATAGGCTCC GCCCCCCTGA CGAGCATCAC AAAAATCGAC GCTCAAGTCA   3660

GAGGTGGCGA AACCCGACAG GACTATAAAG ATACCAGGCG TTTCCCCCTG GAAGCTCCCT   3720

CGTGCGCTCT CCTGTTCCGA CCCTGCCGCT TACCGGATAC CTGTCCGCCT TTCTCCCTTC   3780

GGGAAGCGTG GCGCTTTCTC ATAGCTCACG CTGTAGGTAT CTCAGTTCGG TGTAGGTCGT   3840

TCGCTCCAAG CTGGGCTGTG TGCACGAACC CCCCGTTCAG CCCGACCGCT GCGCCTTATC   3900

CGGTAACTAT CGTCTTGAGT CCAACCCGGT AAGACACGAC TTATCGCCAC TGGCAGCAGC   3960

CACTGGTAAC AGGATTAGCA GAGCGAGGTA TGTAGGCGGT GCTACAGAGT TCTTGAAGTG   4020

GTGGCCTAAC TACGGCTACA CTAGAAGGAC AGTATTTGGT ATCTGCGCTC TGCTGAAGCC   4080

AGTTACCTTC GGAAAAAGAG TTGGTAGCTC TTGATCCGGC AAACAAACCA CCGCTGGTAG   4140

CGGTGGTTTT TTTGTTTGCA AGCAGCAGAT TACGCGCAGA AAAAAAGGAT CTCAAGAAGA   4200

TCCTTTGATC TTTTCTACGG GGTCTGACGC TCAGTGGAAC GAAAACTCAC GTTAAGGGAT   4260

TTTGGTCATG AGATTATCAA AAAGGATCTT CACCTAGATC CTTTTAAATT AAAAATGAAG   4320

TTTTAAATCA ATCTAAAGTA TATATGAGTA AACTTGGTCT GACAGTTACC AATGCTTAAT   4380

CAGTGAGGCA CCTATCTCAG CGATCTGTCT ATTTCGTTCA TCCATAGTTG CCTGACTCCC   4440

CGTCGTGTAG ATAACTACGA TACGGGAGGG CTTACCATCT GGCCCCAGTG CTGCAATGAT   4500

ACCGCGAGAC CCACGCTCAC CGGCTCCAGA TTTATCAGCA ATAAACCAGC CAGCCGGAAG   4560

GGCCGAGCGC AGAAGTGGTC CTGCAACTTT ATCCGCCTCC ATCCAGTCTA TTAATTGTTG   4620

CCGGGAAGCT AGAGTAAGTA GTTCGCCAGT TAATAGTTTG CGCAACGTTG TTGCCATTGC   4680

TACAGGCATC GTGGTGTCAC GCTCGTCGTT TGGTATGGCT TCATTCAGCT CCGGTTCCCA   4740

ACGATCAAGG CGAGTTACAT GATCCCCCAT GTTGTGCAAA AAAGCGGTTA GCTCCTTCGG   4800

TCCTCCGATC GTTGTCAGAA GTAAGTTGGC CGCAGTGTTA TCACTCATGG TTATGGCAGC   4860

ACTGCATAAT TCTCTTACTG TCATGCCATC CGTAAGATGC TTTTCTGTGA CTGGTGAGTA   4920

CTCAACCAAG TCATTCTGAG AATAGTGTAT GCGGCGACCG AGTTGCTCTT GCCCGGCGTC   4980

AACACGGGAT AATACCGCGC CACATAGCAG AACTTTAAAA GTGCTCATCA TTGGAAAACG   5040

TTCTTCGGGG CGAAAACTCT CAAGGATCTT ACCGCTGTTG AGATCCAGTT CGATGTAACC   5100

CACTCGTGCA CCCAACTGAT CTTCAGCATC TTTTACTTTC ACCAGCGTTT CTGGGTGAGC   5160

AAAAACAGGA AGGCAAAATG CCGCAAAAAA GGGAATAAGG GCGACACGGA AATGTTGAAT   5220

ACTCATACTC TTCCTTTTTC AATATTATTG AAGCATTTAT CAGGGTTATT GTCTCATGAG   5280

CGGATACATA TTTGAATGTA TTTAGAAAAA TAAACAAATA GGGGTTCCGC GCACATTTCC   5340

CCGAAAAGTG CCACCTGACG TCTAAGAAAC CATTATTATC ATGACATTAA CCTATAAAAA   5400

TAGGCGTATC ACGAGGCCCT TTCGTCTTCA AGCCCGAGGT AACAAAAAAA CAACAGCATA   5460

AATAACCCCG CTCTTACACA TTCCAGCCCT GAAAAGGGC ATCAAATTAA ACCACACCTA   5520

TGGTGTATGC ATTTATTTGC ATACATTCAA TCAATTGTTA TCTAAGGAAA TACTTACATA   5580

TGGTTCGTGC AAACAAACGC AACGAGGCTC TACGAATCGA TGCATGCAGC TGATTTCACT   5640

TTTTGCATTC TACAAACTGC ATAACTCATA TGTAAATCGC TCCTTTTTAG GTGGCACAAA   5700

TGTGAGGCAT TTCGCTCTT TCCGGCAACC ACTTCCAAGT AAAGTATAAC ACACTATACT   5760
```

-continued

```
TTATATTCAT AAAGTGTGTG CTCTGCGAGG CTGTCGGCAG TGCCGACCAA AACCATAAAA     5820

CCTTTAAGAC CTTTCTTTTT TTTACGAGAA AAAAGAAACA AAAAAACCTG CCCTCTGCCA     5880

CCTCAGCAAA GGGGGGTTTT GCTCTCGTGC TCGTTTAAAA ATCAGCAAGG GACAGGTAGT     5940

ATTTTTTGAG AAGATCACTC AAAAAATCTC CACCTTTAAA CCCTTGCCAA TTTTTATTTT     6000

GTCCGTTTTG TCTAGCTTAC CGAAAGCCAG ACTCAGCAAG AATAAAATTT TTATTGTCTT     6060

TCGGTTTTCT AGTGTAACGG ACAAAACCAC TCAAAATAAA AAAGATACAA GAGAGGTCTC     6120

TCGTATCTTT TATTCAGCAA TCGCGCCCGA TTGCTGAACA GATTAATAAT AGATTTTAGC     6180

TTTTTATTTG TTGAAAAAAG CTAATCAAAT TGTTGTCGGG ATCAATTACT GCAAAGTCTC     6240

GTTCATCCCA CCACTGATCT TTTAATGATG TATTGGGGTG CAAAATGCCC AAAGGCTTAA     6300

TATGTTGATA TAATTCATCA ATTCCCTCTA CTTCAATGCG GCAACTAGCA GTACCAGCAA     6360

TAAACGACTC CGCACCTGTA CAAACCGGTG AATCATTACT ACGAGAGCGC CAGCCTTCAT     6420

CACTTGCCTC CCATAGATGA ATCCGAACCT CATTACACAT TAGAACTGCG AATCCATCTT     6480

CATGGTGAAC CAAAGTGAAA CCTAGTTTAT CGCAATAAAA ACCTATACTC TTTTTAATAT     6540

CCCCGACTGG CAATGCCGGG ATAGACTGTA ACATTCTCAC GCATAAAATC CCCTTTCATT     6600

TTCTAATGTA AATCTATTAC CTTATTATTA ATTCAATTCG CTCATAATTA ATCCTTTTTC     6660

TTATTACGCA AAATGGCCCG ATTTAAGCAC ACCCTTTATT CCGTTAATGC GCCATGACAG     6720

CCATGATAAT TACTAATACT AGGAGAAGTT AATAAATACG TAACCAACAT GATTAACAAT     6780

TATTAGAGGT CATCGTTCAA AATGGTATGC GTTTTGACAC ATCCACTATA TATCCGTGTC     6840

GTTCTGTCCA CTCCTGAATC CCATTCCAGA AATTCTCTAG CGATTCCAGA AGTTTCTCAG     6900

AGTCGGAAAG TTGACCAGAC ATTACGAACT GGCACAGATG GTCATAACCT GAAGGAAGAT     6960

CTGATTGCTT AACTGCTTCA GTTAAGACCG AAGCGCTCGT CGTATAACAG ATGCGATGAT     7020

GCAGACCAAT CAACATGGCA CCTGCCATTG CTACCTGTAC AGTCAAGGAT GGTAGAAATG     7080

TTGTCGGTCC TTGCACACGA ATATTACGCC ATTTGCCTGC ATATTCAAAC AGCTCTTCTA     7140

CGATAAGGGC ACAAATCGCA TCGTGGAACG TTTGGGCTTC TACCGATTTA GCAGTTTGAT     7200

ACACTTTCTC TAAGTATCCA CCTGAATCAT AAATCGGCAA AATAGAGAAA AATTGACCAT     7260

GTGTAAGCGG CCAATCTGAT TCCACCTGAG ATGCATAATC TAGTAGAATC TCTTCGCTAT     7320

CAAAATTCAC TTCCACCTTC CACTCACCGG TTGTCCATTC ATGGCTGAAC TCTGCTTCCT     7380

CTGTTGACAT GACACACATC ATCTCAATAT CCGAATAGGG CCCATCAGTC TGACGACCAA     7440

GAGAGCCATA AACACCAATA GCCTTAACAT CATCCCCATA TTTATCCAAT ATTCGTTCCT     7500

TAATTTCATG AACAATCTTC ATTCTTTCTT CTCTAGTCAT TATTATTGGT CCATTCACTA     7560

TTCTCATTCC CTTTTCAGAT AATTTTAGAT TTGCTTTTCT AAATAAGAAT ATTTGGAGAG     7620

CACCGTTCTT ATTCAGCTAT TAATAACTCG TCTTCCTAAG CATCCTTCAA TCCTTTTAAT     7680

AACAATTATA GCATCTAATC TTCAACAAAC TGGCCCGTTT GTTGAACTAC TCTTTAATAA     7740

AATAATTTTT CCGTTCCCAA TTCCACATTG CAATAATAGA AAATCCATCT TCATCGGCTT     7800

TTTCGTCATC ATCTGTATGA ATCAAATCGC CTTCTTCTGT GTCATCAAGG TTTAATTTTT     7860

TATGTATTTC TTTTAACAAA CCACCATAGG AGATTAACCT TTTACGGTGT AAACCTTCCT     7920

CCAAATCAGA CAAACGTTTC AAATTCTTTT CTTCATCATC GGTCATAAAA TCCGTATCCT     7980

TTACAGGATA TTTTGCAGTT TCGTCAATTG CCGATTGTAT ATCCGATTTA TATTTATTTT     8040

TCGGTCGAAT CATTTGAACT TTTACATTTG GATCATAGTC TAATTTCATT GCCTTTTTCC     8100
```

-continued

```
AAAATTGAAT CCATTGTTTT TGATTCACGT AGTTTTCTGT ATTCTTAAAA TAAGTTGGTT      8160

CCACACATAC CAATACATGC ATGTGCTGAT TATAAGAATT ATCTTTATTA TTTATTGTCA      8220

CTTCCGTTGC ACGCATAAAA CCAACAAGAT TTTTATTAAT TTTTTTATAT TGCATCATTC      8280

GGCGAAATCC TTGAGCCATA TCTGACAAAC TCTTATTTAA TTCTTCGCCA TCATAAACAT      8340

TTTTAACTGT TAATGTGAGA ACAACCAAC GAACTGTTGG CTTTTGTTTA ATAACTTCAG       8400

CAACAACCTT TTGTGACTGA ATGCCATGTT TCATTGCTCT CCTCCAGTTG CACATTGGAC      8460

AAAGCCTGGA TTTACAAAAC CACACTCGAT ACAACTTTCT TTCGCCTGTT TCACGATTTT      8520

GTTTATACTC TAATATTTCA GCACAATCTT TTACTCTTTC AGCCTTTTTA AATTCAAGAA      8580

TATGCAGAAG TTCAAAGTAA TCAACATTAG CGATTTTCTT TTCTCTCCAT GGTCTCACTT      8640

TTCCACTTTT TGTCTTGTCC ACTAAAACCC TTGATTTTTC ATCTGAATAA ATGCTACTAT      8700

TAGGACACAT AATATTAAAA GAAACCCCCA TCTATTTAGT TATTTGTTTA GTCACTTATA      8760

ACTTTAACAG ATGGGGTTTT TCTGTGCAAC CAATTTTAAG GGTTTTCAAT ACTTTAAAAC      8820

ACATACATAC CAACACTTCA ACGCACCTTT CAGCAACTAA AATAAAAATG ACGTTATTTC      8880

TATATGTATC AAGATAAGAA AGAACAAGTT CAAAACCATC AAAAAAAGAC ACCTTTTCAG      8940

GTGCTTTTTT TATTTTATAA ACTCATTCCC TGATCTCGAC TTCGTTCTTT TTTTACCTCT      9000

CGGTTATGAG TTAGTTCAAA TTCGTTCTTT TTAGGTTCTA AATCGTGTTT TTCTTGGAAT      9060

TGTGCTGTTT TATCCTTTAC CTTGTCTACA AACCCCTTAA AAACGTTTTT AAAGGCTTTT      9120

AAGCCGTCTG TACGTTCCTT AAGG                                             9144
```

(2) INFORMATION FOR SEQ ID NO:80:

(i) SEQUENCE CHARACTERISTICS:
        (A) LENGTH: 303 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:80:

```
GGGCCGGTCG AGGTGGACAA GGTGCAGGTG CAGCCGCTGC TGCTGCGGGC GGCGCAGGTC        60

AAGGTGGGTA TGGGGGTTTA GGTTCACAAG GGGCCGGACG TGGTGGCCTT GGTGGTCAGG       120

GTGCTGGCGC GGCAGCCGCT GCGGCAGCTG GTGGTGCTGG TCAGGGCGGT CTTGGCTCAC       180

AAGGGGCCGG TCAAGGCGCT GGTGCAGCAG CAGCTGCCGC TGGCGGTGCA GGCCAAGGTG       240

GATATGGTGG CTTAGGGTCA CAAGGGGCCG GGCAAGGTGG TTACGGCGGT CTCGGATCAC       300

AAG                                                                    303
```

(2) INFORMATION FOR SEQ ID NO:81:

(i) SEQUENCE CHARACTERISTICS:
        (A) LENGTH: 303 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:81:

```
GGGCCGGGCA AGGTGGTTAC GGCGGTCTCG GATCACAAGG GGCCGGACGT GGTGGCCTTG        60

GTGGTCAGGG TGCTGGCGCG GCAGCCGCTG CGGCAGCTGG TGGTGCTGGT CAGGGCGGTC       120

TTGGCTCACA AGGGGCCGGT CAAGGCGCTG GTGCAGCAGC AGCTGCCGCT GGCGGTGCAG       180
```

```
GCCAAGGTGG ATATGGTGGC TTAGGGTCAC AAGGGGCCGG TCGAGGTGGA CAAGGTGCAG      240

GTGCAGCCGC TGCTGCTGCG GGCGGCGCAG GTCAAGGTGG GTATGGGGGT TTAGGTTCAC      300

AAG                                                                   303
```

(2) INFORMATION FOR SEQ ID NO:82:

(i) SEQUENCE CHARACTERISTICS:
        (A) LENGTH: 303 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:82:

```
TCTCAGGGTG CTGGCCAGGG TGGCTATGGT GGCCTGGGAT CTCAAGGCGC TGGTCGCGGT       60

GGCCTGGGTG CCAGGGTGC AGGTGCTGCT GCTGCTGCGG CTGCTGGTGG TGCAGGTCAG       120

GGTGGTCTGG GATCTCAGGG CGCAGGTCAA GGTGCTGGTG CAGCTGCGGC GGCAGCTGGT      180

GGCGCGGGTC AAGGTGGCTA CGGCGGTTTA GGATCTCAAG GTGCGGGTCG CGGTGGTCAG      240

GGCGCTGGTG CAGCAGCGGC AGCAGCAGGT GGCGCTGGCC AAGGTGGTTA CGGTGGTCTT      300

GGA                                                                   303
```

(2) INFORMATION FOR SEQ ID NO:83:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:83:

```
GGGCCATCCG GCCCAGGTTC TGCGGCAGCG GCAGCAGCGG GCCCAGGGCA GCAGGGGCCG       60

GGCGGTTACG GTCCGGGTCA GCAAGGCCCA GGTGGCTACG GCCCAGGCCA ACAGGGGCCA      120

TCTGGTCCGG GTAGCGCTGC GGCTGCTGCT GCTGCGGCAG GTCCAGGCGG CTACGGGCCG      180

GGCCAACAAG GTCCGGGCGG CTATGGTCCA GGTCAACAGG GGCCGAGCGG TCCAGGTTCC      240

GCAGCAGCAG CGGCTGCGGC GGCAGCGGGT CCAGGTGGTT ACGGGCCAGG CCAGCAGGGT      300

CCGGGTGGCT ATGGCCCAGG CCAGCAAGGT CCGGGTGGTT ACGGTCCAGG TCAGCAG         357
```

(2) INFORMATION FOR SEQ ID NO: 84:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 84:

```
GATCTCAAGG AGCCGGTCAA GGTGGTTACG GAGGTCTGG                              39
```

(2) INFORMATION FOR SEQ ID NO: 85:

(i) SEQUENCE CHARACTERISTICS:
        (A) LENGTH: 39 base pairs
        (B) TYPE: nucleic acid
        (C) STRANDEDNESS: single

```
            (D) TOPOLOGY: linear (ii) MOLECULE TYPE: DNA (genomic)

(xi) SEQUENCE DESCRIPTION: SEQ ID NO: 85:

GATCCCAGAC CTCCGTAACC ACCTTGACCG GCTCCTTGA                      39

(2) INFORMATION FOR SEQ ID NO: 86:

(i) SEQUENCE CHARACTERISTICS:
            (A) LENGTH: 13 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO: 86:

Ser Gln Gly Ala Gly Gln Gly Gly Tyr Gly Gly Leu Gly
1               5                  10

(2) INFORMATION FOR SEQ ID NO: 87:

(i) SEQUENCE CHARACTERISTICS:
            (A) LENGTH: 93 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 87:

GATCTCAAGG TGCTGGACGT GGTGGTCTTG GTGGTCAGGG TGCCGGTGCC GCCGCTGCCG    60

CCGCCGCTGG TGGTGCTGGA CAAGGTGGTT TGG                                93

(2) INFORMATION FOR SEQ ID NO: 88:

(i) SEQUENCE CHARACTERISTICS:
            (A) LENGTH: 93 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 88:

GATCCCAAAC CACCTTGTCC AGCACCACCA GCGGCGGCGG CAGCGGCGGC ACCGGCACCC    60

TGACCACCAA GACCACCACG TCCAGCACCT TGA                                93

(2) INFORMATION FOR SEQ ID NO: 89:

(i) SEQUENCE CHARACTERISTICS:
            (A) LENGTH: 31 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO: 89:

Ser Gln Gly Ala Gly Arg Gly Gly Leu Gly Gly Gln Gly Ala Gly Ala
1               5                  10                  15

Ala Ala Ala Ala Ala Ala Gly Gly Ala Gly Gln Gly Gly Leu Gly
                20                  25                  30

(2) INFORMATION FOR SEQ ID NO: 90:
```

(i) SEQUENCE CHARACTERISTICS:
            (A) LENGTH: 81 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 90:

GATCTCAGGG AGCTGGTCAA GGTGCCGGTG CTGCTGCCGC TGCTGCCGGA GGTGCCGGTC        60

AGGGTGGATA CGGTGGACTT G        81

(2) INFORMATION FOR SEQ ID NO: 91:

(i) SEQUENCE CHARACTERISTICS:
            (A) LENGTH: 81 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 91:

GATCCAAGTC CACCGTATCC ACCCTGACCG GCACCTCCGG CAGCAGCGGC AGCAGCACCG        60

GCACCTTGAC CAGCTCCCTG A        81

(2) INFORMATION FOR SEQ ID NO: 92:

(i) SEQUENCE CHARACTERISTICS:
            (A) LENGTH: 27 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO: 92:

Ser Gln Gly Ala Gly Gln Gly Ala Gly Ala Ala Ala Ala Ala Gly
1               5                   10                  15

Gly Ala Gly Gln Gly Gly Tyr Gly Gly Leu Gly
            20                  25

(2) INFORMATION FOR SEQ ID NO: 93:

(i) SEQUENCE CHARACTERISTICS:
            (A) LENGTH: 90 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 93:

GATCTCAGGG TGCTGGTAGA GGTGGACAAG GTGCCGGAGC TGCCGCTGCC GCTGCCGGTG        60

GTGCTGGTCA AGGAGGTTAC GGTGGTCTTG        90

(2) INFORMATION FOR SEQ ID NO: 94:

(i) SEQUENCE CHARACTERISTICS:
            (A) LENGTH: 90 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 94:

GATCCAAGAC CACCGTAACC TCCTTGACCA GCACCACCGG CAGCGGCAGC GGCAGCTCCG    60

GCACCTTGTC CACCTCTACC AGCACCCTGA    90

(2) INFORMATION FOR SEQ ID NO: 95:

(i) SEQUENCE CHARACTERISTICS:
      (A) LENGTH: 30 amino acids
      (B) TYPE: amino acid
      (C) STRANDEDNESS: unknown
      (D) TOPOLOGY: unknown (ii) MOLECULE TYPE: peptide (xi) SEQUENCE DESCRIPTION: SEQ ID NO: 95:

Ser Gln Gly Ala Gly Arg Gly Gly Gln Gly Ala Gly Ala Ala Ala
1               5                  10                  15

Ala Ala Gly Gly Ala Gly Gln Gly Gly Tyr Gly Gly Leu Gly
                20                  25                  30

(2) INFORMATION FOR SEQ ID NO: 96:

(i) SEQUENCE CHARACTERISTICS:
      (A) LENGTH: 588 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 96:

ATGCATTGTC TCCACATTGT ATGCTTCCAA GATTCTGGTG GGAATACTGC TGATAGCCTA    60

ACGTTCATGA TCAAAATTTA ACTGTTCTAA CCCCTACTTG ACAGCAATAT ATAAACAGAA   120

GGAAGCTGCC CTGTCTTAAA CCTTTTTTTT TATCATCATT ATTAGCTTAC TTTCATAATT   180

GCGACTGGTT CCAATTGACA AGCTTTTGAT TTTAACGACT TTTAACGACA ACTTGAGAAG   240

ATCAAAAAAC AACTAATTAT TCGAAACGAT GAGATTTCCT TCAATTTTTA CTGCAGTTTT   300

ATTCGCAGCA TCCTCCGCAT TAGCTGCTCC AGTCAACACT ACAACAGAAG ATGAAACGGC   360

ACAAATTCCG GCTGAAGCTG TCATCGGTTA CTCAGATTTA GAAGGGGATT TCGATGTTGC   420

TGTTTTGCCA TTTTCCAACA GCACAAATAA CGGGTTATTG TTTATAAATA CTACTATTGC   480

CAGCATTGCT GCTAAAGAAG AAGGGGTATC TCTCGAGAAA AGAGAGGCTG AAGCTTACGT   540

AGAATTCCCT AGGGCGGCCG CGAATTAATT CGCCTTAGAC ATGACTGT                588

(2) INFORMATION FOR SEQ ID NO: 97:

(i) SEQUENCE CHARACTERISTICS:
      (A) LENGTH: 93 amino acids
      (B) TYPE: amino acid
      (C) STRANDEDNESS: unknown
      (D) TOPOLOGY: unknown (ii) MOLECULE TYPE: peptide (xi) SEQUENCE DESCRIPTION: SEQ ID NO: 97:

Met Arg Phe Pro Ser Ile Phe Thr Ala Val Leu Phe Ala Ala Ser Ser
1               5                  10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
                35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Tyr Val Glu Phe
                85                  90

(2) INFORMATION FOR SEQ ID NO: 98:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 98:

CAACTAATTA TTCGAAACGA TGAGATTTCC                                      30

(2) INFORMATION FOR SEQ ID NO: 99:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 99:

CTGAGGAACA GTCATGTCTA AGG                                             23

(2) INFORMATION FOR SEQ ID NO: 100:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 100:

GGAAATCTCA TCGTTTCGAA TAATTAGTTG                                      30

(2) INFORMATION FOR SEQ ID NO: 101:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 101:

GAAACGCAAA TGGGGAAACA ACC                                             23

(2) INFORMATION FOR SEQ ID NO: 102:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE:  peptide (xi) SEQUENCE DESCRIPTION:  SEQ ID NO: 102:

Met Gly Ser His His His His His
1               5

(2) INFORMATION FOR SEQ ID NO: 103:

(i) SEQUENCE CHARACTERISTICS:
            (A) LENGTH:  32 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO: 103:

AATTATGGGA TCCCATCACC ATCACCATCA CT                                32

(2) INFORMATION FOR SEQ ID NO: 104:

(i) SEQUENCE CHARACTERISTICS:
            (A) LENGTH:  32 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO: 104:

AATTAGTGAT GGTGATGGTG ATGGGATCCC AT                                32

(2) INFORMATION FOR SEQ ID NO: 105:

(i) SEQUENCE CHARACTERISTICS:
            (A) LENGTH:  6 amino acids
            (B) TYPE:  amino acid
            (C) STRANDEDNESS:  unknown
            (D) TOPOLOGY:  unknown (ii) MOLECULE TYPE:  peptide (xi) SEQUENCE DESCRIPTION:  SEQ ID NO: 105:

Phe Gly Ser Gln Gly Ala
1               5

(2) INFORMATION FOR SEQ ID NO: 106:

(i) SEQUENCE CHARACTERISTICS:
            (A) LENGTH:  23 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO: 106:

AATTCGGATC CCAGGGTGCT TAA                                          23

(2) INFORMATION FOR SEQ ID NO: 107:

(i) SEQUENCE CHARACTERISTICS:
            (A) LENGTH:  23 base pairs
            (B) TYPE:  nucleic acid
            (C) STRANDEDNESS:  single
            (D) TOPOLOGY:  linear (ii) MOLECULE TYPE:  DNA (genomic)

-continued (xi) SEQUENCE DESCRIPTION: SEQ ID NO: 107:

GGCCTTAAGC ACCCTGGGAT CCG                                                                                        23